United States Patent [19]

Epenetos et al.

[11] Patent Number: 5,973,116
[45] Date of Patent: Oct. 26, 1999

[54] COMPOUNDS FOR TARGETING

[75] Inventors: Agamemnon Antoniou Epenetos; Robert Anthony Spooner, both of London; Mahendra Deonarain, Wallington, all of United Kingdom

[73] Assignee: Imperial Cancer Research Technology Limited, London, United Kingdom

[21] Appl. No.: 08/491,988

[22] PCT Filed: Jan. 17, 1994

[86] PCT No.: PCT/GB94/00087

§ 371 Date: Dec. 18, 1995

§ 102(e) Date: Dec. 18, 1995

[87] PCT Pub. No.: WO94/15644

PCT Pub. Date: Jul. 21, 1994

[30] Foreign Application Priority Data

Jan. 15, 1993 [GB] United Kingdom .................. 9300686

[51] Int. Cl.[6] .............................. C07K 1/00; C07K 16/00
[52] U.S. Cl. .................... 530/350; 530/391.1; 530/391.7
[58] Field of Search .............................. 424/130.1, 277.1, 424/178.1; 530/350, 391.1, 391.7

[56] References Cited

FOREIGN PATENT DOCUMENTS 8903422  4/1989  WIPO .
9219273  11/1992  WIPO .
9317715  9/1993  WIPO .

OTHER PUBLICATIONS

Hollinger et al, "Diabodies": Small Bivalent and Bispecific Antibody Fragments Proc. Natl. Acad. Scie USA vol. 90, pp.
Rybak et al, "Cytotoxic Potential of Ribonuclease and Ribonuclease Hybrid" J. of Biological Chemistry, vol. 266, pp. 21202–21207.
Worrall et al (JBC, 265: 21889–21895) 1990.
Lazar et al (Mol & Cell Bio, 8: 1247–1252) 1988.
Burgess et al (J. Cell Bio, 111:2129–2138) 1990.
Tao et al. (J. Immunol, 143:2595–2601 1989.
Hird et al (Genes & Cancer, Carney et al Ed, John Wiley & Sons, 1990, pp. 83–89.
Kimmel et al (J. Neurosurg, 66:161–171, 1987).

*Primary Examiner*—Paula K. Hutzell
*Assistant Examiner*—Susan Ungar
*Attorney, Agent, or Firm*—McAulay Nissen Goldberg Kiel & Hand, LLP

[57] ABSTRACT

Fusion compounds comprising a target cell-specific portion fused to an oligomeric rival nuclease are disclosed. The inventive compounds are useful as anti-cancer agents. Methods of preparation and use of the inventive compounds are disclosed.

10 Claims, 38 Drawing Sheets

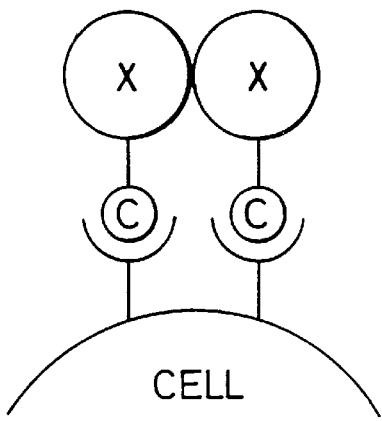
Fig. 1(a)
Fig. 1(b)
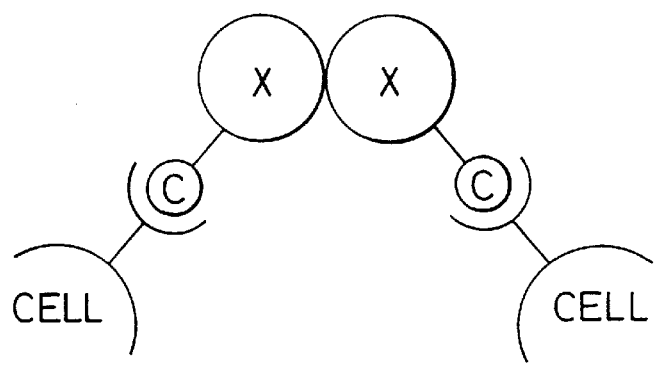
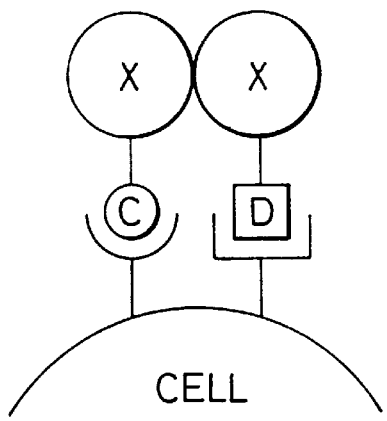
Fig. 1(c)
Fig. 1(d)
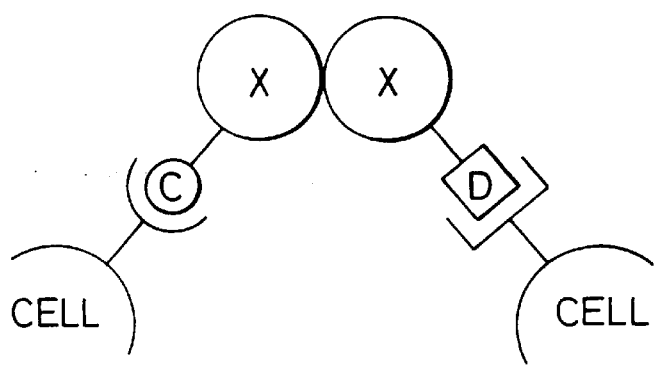

```
              L   Q   E   S   G   P
VHBACK2      CAGGTGCAGCTGCAGGAGTCAGGACC   VHBACK2
                      PstI

G   S
BAMLINKERFOR GGATCCGACATCGAGCTCACTCAGTCTCCA
             BamHI

G   S   Q   A   E   L   T   Q   E   S
BAMVλBACK    AAGCTTGGATCCCAGGCTGTTGTGACTCAGGAATCT
                    BamHI

K   L   T   V   L   G   R   S   *   *
ECOVλFOR     CCAAACTGACTGTCCTAGGTCTCGAGTAATAAGAATTCATGC
                                    XhoI           EcoRI

L   Q   Q   P   G
VHBACK3      CAGGTCCAACTGCAGCAGCCTGG
                       PstI

G   Q   G   T   T   L   T
VH1FOR-2     GGGGCCAAGGGACCACGGTCACCGTCTCCTCA
                                 BstEII
```

FIGURE 3

```
                    10              20              30              40              50
                                                                             M  K  Y  L  L  P
AAGCTTGCATGCAAATTCTATTTCAAGGAGACAGTCATAATGAAATACCTATTGCCT
HindIIISphI                      SD                    /----------------
```

```
         60              70              80              90             100             110
    T  A  A  A  G  L  L  L  L  A  A  Q  P  A  M  A  Q  V  Q
ACGGCAGCCGCTGGATTGTTATTACTCGCTGCCCAACCAGCGATGGCCCAGGTGCAG
------pelB leader---------------------------------/VH$_{NP}$
```

```
        120             130             140             150             160             170
    L  Q  Q  P  G  A  E  L  V  K  P  G  A  S  V  K  L  S  C
CTGCAGCAGCCTGGGGCTGAGCTTGTGAAGCCTGGGGCTTCAGTGAAGCTGTCCTGC
PstI
```

```
             180             190             200             210             220          2
    K  A  S  G  Y  T  F  T  S  Y  W  M  H  W  V  K  Q  R  P
AAGGCTTCTGGCTACACCTTCACCAGCTACTGGATGCACTGGGTGAAGCAGAGGCCT
                                 CDR1
```

```
   30              240             250             260             270             280
    G  R  G  L  E  W  I  G  R  I  D  P  N  S  G  G  T  R  Y
GGACGAGGCCTTGAGTGGATTGGAAGGATTGATCCTAATAGTGGTGGTACTAAGTAC
                             CDR2
```

```
        290             300             310             320             330             340
    N  E  K  F  L  S  K  A  T  L  T  V  D  K  P  S  S  T  A
AATGAGAAGTTCAAGAGCAAGGCCACACTGACTGTAGACAAACCCTCCAGCACAGCC
```

```
         350             360             370             380             390             40
    Y  M  Q  L  S  S  L  T  S  E  D  S  A  V  Y  Y  C  A  R
TACATGCAGCTCAGCAGCCTGACATCTGAGGACTCTGCGGTCTATTATTGTGCAAGA
```

```
  0             410             420             430             440             450
    Y  D  Y  Y  G  S  S  Y  F  D  Y  W  G  Q  G  T  T  L  T
TACGATTACTACGGTAGTAGCTACTTTGACTACTGGGGCCAAGGGACCACGGTCACC
          CDR3                                              BstEII
```

```
    460             470             480             490             500             510
  V  S  S  G  G  G  G  S  G  G  G  G  S  G  G  G  G  S  Q
GTCTCCTCAGGTGGAGGCGGTTCAGGCGGAGGTGGCTCTGGCGGTGGCGGATCCCAG
         /-----------(G$_4$S)$_3$ linker------------BamHI-/V$\lambda$
```

```
        520             530             540             550             560             570
    V  V  L  T  Q  E  S  A  L  T  T  S  P  G  E  T  V  T  L
GCTGTTGTGACTCAGGAATCTGCACTCACCACATCACCTGGTGAAACAGTCACACTC
```

```
        580             590             600             610             620
    T  C  R  S  S  T  G  A  V  T  T  S  N  Y  A  N  W  V  Q
ACTTGTCGCTCAAGTACTGGGGCTGTTACAACTAGTAACTATGCCAACTGGGTCCAA
                 CDR1
```

FIGURE 4A

```
        630         640         650         660         670         680
     E   K   P   D   H   L   F   T   G   L   I   G   G   T   N   N   R   A   P
    GAAAAACCAGATCATTTATTCACTGGTCTAATAGGTGGTACCAACAACCGAGCTCCA
                                       KpnI   CDR2      SstI 690         700         710         720         730         740
     G   V   P   A   R   F   S   G   S   L   I   G   D   K   A   A   L   T   I
    GGTGTTCCTGCCAGATTCTCAGGCTCCCTGATTGGAGACAAGGCTGCCCTCACCATC 750         760         770         780         790         8
     T   G   A   Q   T   E   D   E   A   I   Y   F   C   A   L   W   Y   S   N
    ACAGGGGCACAGACTGAGGATGAGGCAATATATTTCTGTGCTCTATGGTACAGCAAC
                                                 CDR3

00          810         820         830         840         850
     H   W   V   F   G   G   G   T   K   L   T   V   L   G   L   E   *   *
    CACTGGGTGTTCGGTGGAGGAACCAAACTGACTGTCCTAGGTCTCGAGTAATAAGAA
                                                 XhoI          Eco

TTC
    RI
```

FIGURE 4B

```
              10           20           30           40           50           60
                                                                M  K  Y  L  L  P  T
AAGCTTGCATGCAAATTCTATTTCAAGGAGACAGTCATAATGAAATACCTATTGCCTACG
HindIIISphI                  SD        /--------------------
```

```
              70           80           90          100          110          120
 A  A  A  G  L  L  L  L  A  A  Q  P  A  M  A  Q  V  Q  L  Q
GCAGCCGCTGGATTGTTATTACTCGCTGCCCAACCAGCGATGGCCCAGGTGCAGCTGCAG
------pelB leader--------------------------------/VH_NP  PstI
```

```
             130          140          150          160          170          180
 Q  P  G  A  E  L  V  K  P  G  A  S  V  K  L  S  C  K  A  S
CAGCCTGGGGCTGAGCTTGTGAAGCCTGGGGCTTCAGTGAAGCTGTCCTGCAAGGCTTCT
```

```
             190          200          210          220          230          240
 G  Y  T  F  T  S  Y  W  M  H  W  V  K  Q  R  P  G  R  G  L
GGCTACACCTTCACCAGCTACTGGATGCACTGGGTGAAGCAGAGGCCTGGACGAGGCCTT
                 CDR1
```

```
             250          260          270          280          290          300
 E  W  I  G  R  I  D  P  N  S  G  G  T  R  Y  N  E  K  F  L
GAGTGGATTGGAAGGATTGATCCTAATAGTGGTGGTACTAAGTACAATGAGAAGTTCAAG
                                CDR2
```

```
             310          320          330          340          350          360
 S  K  A  T  L  T  V  D  K  P  S  S  T  A  Y  M  Q  L  S  S
AGCAAGGCCACACTGACTGTAGACAAACCCTCCAGCACAGCCTACATGCAGCTCAGCAGC
```

```
             370          380          390          400          410          420
 L  T  S  E  D  S  A  V  Y  Y  C  A  R  Y  D  Y  Y  G  S  S
CTGACATCTGAGGACTCTGCGGTCTATTATTGTGCAAGATACGATTACTACGGTAGTAGC
```

```
             430          440          450          460          470          480
 Y  F  D  Y  W  G  Q  G  T  T  L  T  V  S  S  G  G  G  G  S
TACTTTGACTACTGGGGCCAAGGGACCACGGTCACCGTCTCCTCAGGTGGAGGCGGTTCA
CDR3                             BstEII              /---(G4S)3-----
```

```
             490          500          510          520          530          540
 G  G  G  G  S  G  G  G  G  S  Q  V  V  L  T  Q  E  S  A  L
GGCGGAGGTGGCTCTGGCGGTGGCGGATCCCAGGCTGTTGTGACTCAGGAATCTGCACTC
-------------------------BamHI-/Vλ_J558L
```

```
             550          560          570          580          590          600
 T  T  S  P  G  E  T  V  T  L  T  C  R  S  S  T  G  A  V  T
ACCACATCACCTGGTGAAACAGTCACACTCACTTGTCGCTCAAGTACTGGGGCTGTTACA
                                                           CDR1
```

```
             610          620          630          640          650          660
 T  S  N  Y  A  N  W  V  Q  E  K  P  D  H  L  F  T  G  L  I
ACTAGTAACTATGCCAACTGGGTCCAAGAAAAACCAGATCATTTATTCACTGGTCTAATA
```

```
             670          680          690          700          710          720
 G  G  T  N  N  R  A  P  G  V  P  A  R  F  S  G  S  L  I  G
GGTGGTACCAACAACCGAGCTCCAGGTGTTCCTGCCAGATTCTCAGGCTCCCTGATTGGA
    KpnI    CDR2   SstI
```

```
             730          740          750          760          770          780
 D  K  A  A  L  T  I  T  G  A  Q  T  E  D  E  A  I  Y  F  C
GACAAGGCTGCCCTCACCATCACAGGGGCACAGACTGAGGATGAGGCAATATATTTCTGT
```

FIGURE 9A

```
          790         800         810         820         830         840
  A    L    W    Y    S    N    H    W    V    F    G    G    G    T    K    L    T    V    L    G
GCTCTATGGTACAGCAACCACTGGGTGTTCGGTGGAGGAACCAAACTGACTGTCCTAGGT
        CDR3

850         860         870         880         890         900
  L    E    A    P    A    A    A    P    A    D    P    S    K    D    S    K    A    Q    V    S
CTCGAGGCACCTGCTGCCGCACCTGCAGACCCGTCCAAGGACTCCAAAGCTCAGGTTTCT
XhoI    /-Ala.Pro linker-----/Streptavidin                              Ps 910         920         930         940         950         960
  A    A    E    A    G    I    T    G    T    W    Y    N    Q    L    G    S    T    F    I    V
GCAGCCGAAGCTGGTATCACTGGCACCTGGTATAACCAACTGGGGTCGACTTTCATTGTG
tI                                                   SalI 970         980         990        1000        1010        1020
  T    A    G    A    D    G    A    L    T    G    T    Y    E    S    A    V    G    N    A    E
ACCGCTGGTGCGGACGGAGCTCTGACTGGCACCTACGAATCTGCGGTTGGTAACGCAGAA 1030        1040        1050        1060        1070        1080
  S    R    Y    V    L    T    G    R    Y    D    S    A    P    A    T    D    G    S    G    T
TCCCGCTACGTACTGACTGGCCGTTATGACTCTGCACCTGCCACCGATGGCTCTGGTACC
                                                              KpnI 1090        1100        1110        1120        1130        1140
  A    L    G    W    T    V    A    W    K    N    N    Y    R    N    A    H    S    A    T    T
GCTCTGGGCTGGACTGTGGCTTGGAAAAACAACTATCGTAATGCGCACAGCGCCACTACG 1150        1160        1170        1180        1190        1200
  W    S    G    Q    Y    V    G    G    A    E    A    R    I    N    T    Q    W    L    L    T
TGGTCTGGCCAATACGTTGGCGGTGCTGAGGCTCGTATCAACACTCAGTGGCTGTTAACA 1210        1220        1230        1240        1250        1260
  S    G    T    T    E    A    N    A    W    K    S    T    L    V    G    H    D    T    F    T
TCCGGCACTACCGAAGCGAATGCATGGAAATCGACACTAGTAGGTCATGACACCTTTACC 1270        1280        1290        1300        1310        1320
  K    V    K    P    S    A    A    S    I    D    A    A    K    K    A    G    V    N    N    G
AAAGTTAAGCCTTCTGCTGCTAGCATTGATGCTGCCAAGAAAGCAGGCGTAAACAACGGT
                                                                    Bst 1330        1340        1350        1360
  N    P    L    D    A    V    Q    Q    *    *
AACCCTCTAGACGCTGTTCAGCAATAATAAGAATTC
EII    XbaI                           EcoRI
```

FIGURE 9B

```
              10         20         30         40         50         60
                                                  M   K   Y   L   L   P   T
AAGCTTGCATGCAAATTCTATTTCAAGGAGACAGTCATAATGAAATACCTATTGCCTACG
HindIIISphI              SD        /------------------

70         80         90        100        110        120
  A   A   A   G   L   L   L   L   A   A   Q   P   A   M   A   Q   V   Q   L   Q
GCAGCCGCTGGATTGTTATTACTCGCTGCCCAACCAGCGATGGCCCAGGTGCAGCTGCAG
------pelB leader--------------------------/VH_NP  PstI 130        140        150        160        170        180
  Q   P   G   A   E   L   V   K   P   G   A   S   V   K   L   S   C   K   A   S
CAGCCTGGGGCTGAGCTTGTGAAGCCTGGGGCTTCAGTGAAGCTGTCCTGCAAGGCTTCT 190        200        210        220        230        240
  G   Y   T   F   T   S   Y   W   M   H   W   V   K   Q   R   P   G   R   G   L
GGCTACACCTTCACCAGCTACTGGATGCACTGGGTGAAGCAGAGGCCTGGACGAGGCCTT
                   CDR1

250        260        270        280        290        300
  E   W   I   G   R   I   D   P   N   S   G   G   T   R   Y   N   E   K   F   L
GAGTGGATTGGAAGGATTGATCCTAATAGTGGTGGTACTAAGTACAATGAGAAGTTCAAG
                        CDR2

310        320        330        340        350        360
  S   K   A   T   L   T   V   D   K   P   S   S   T   A   Y   M   Q   L   S   S
AGCAAGGCCACACTGACTGTAGACAAACCCTCCAGCACAGCCTACATGCAGCTCAGCAGC 370        380        390        400        410        420
  L   T   S   E   D   S   A   V   Y   Y   C   A   R   Y   D   Y   Y   G   S   S
CTGACATCTGAGGACTCTGCGGTCTATTATTGTGCAAGATACGATTACTACGGTAGTAGC 430        440        450        460        470        480
  Y   F   D   Y   W   G   Q   G   T   T   L   T   V   S   S   G   G   G   G   S
TACTTTGACTACTGGGGCCAAGGGACCACGGTCACCGTCTCCTCAGGTGGAGGCGGTTCA
CDR3                              BstEII       /---(G_4S)_3-----

490        500        510        520        530        540
  G   G   G   G   S   G   G   G   G   S   Q   V   V   L   T   Q   E   S   A   L
GGCGGAGGTGGCTCTGGCGGTGGCGGATCCCAGGCTGTTGTGACTCAGGAATCTGCACTC
-----------------------BamHI-/Vλ_J558L 550        560        570        580        590        600
  T   T   S   P   G   E   T   V   T   L   T   C   R   S   S   T   G   A   V   T
ACCACATCACCTGGTGAAACAGTCACACTCACTTGTCGCTCAAGTACTGGGGCTGTTACA
                                             CDR1

610        620        630        640        650        660
  T   S   N   Y   A   N   W   V   Q   E   K   P   D   H   L   F   T   G   L   I
ACTAGTAACTATGCCAACTGGGTCCAAGAAAAACCAGATCATTTATTCACTGGTCTAATA 670        680        690        700        710        720
  G   G   T   N   N   R   A   P   G   V   P   A   R   F   S   G   S   L   I   G
GGTGGTACCAACAACCGAGCTCCAGGTGTTCCTGCCAGATTCTCAGGCTCCCTGATTGGA
     KpnI    CDR2  SstI 730        740        750        760        770        780
  D   K   A   A   L   T   I   T   G   A   Q   T   E   D   E   A   I   Y   F   C
GACAAGGCTGCCCTCACCATCACAGGGGCACAGACTGAGGATGAGGCAATATATTTCTGT
```

FIGURE 10A

```
           790       800       810       820       830       840
     A  L  W  Y  S  N  H  W  V  F  G  G  G  T  K  L  T  V  L  G
   GCTCTATGGTACAGCAACCACTGGGTGTTCGGTGGAGGAACCAAACTGACTGTCCTAGGT
       CDR3

850       860       870       880       890       900
     L  E  A  P  A  A  A  P  A  D  P  S  K  D  S  K  A  Q  V  S
   CTCGAGGCACCTGCTGCCGCACCTGCAGACCCGTCCAAGGACTCCAAAGCTCAGGTTTCT
   XhoI  /-Ala.Pro linker-----/Streptavidin                  Ps 910       920       930       940       950       960
     A  A  E  A  G  I  T  G  T  W  Y  N  Q  L  G  S  T  F  I  V
   GCAGCCGAAGCTGGTATCACTGGCACCTGGTATAACCAACTGGGGTCGACTTTCATTGTG
   tI                                              SalI 970       980       990      1000      1010      1020
     T  A  G  A  D  G  A  L  T  G  T  Y  E  S  A  V  G  N  A  E
   ACCGCTGGTGCGGACGGAGCTCTGACTGGCACCTACGAATCTGCGGTTGGTAACGCAGAA 1030      1040      1050      1060      1070      1080
     S  R  Y  V  L  T  G  R  Y  D  S  A  P  A  T  D  G  S  G  T
   TCCCGCTACGTACTGACTGGCCGTTATGACTCTGCACCTGCCACCGATGGCTCTGGTACC
                                                          KpnI 1090      1100      1110      1120      1130      1140
     A  L  G  W  T  V  A  W  K  N  N  Y  R  N  A  H  S  A  T  T
   GCTCTGGGCTGGACTGTGGCTTGGAAAAACAACTATCGTAATGCGCACAGCGCCACTACG 1150      1160      1170      1180      1190      1200
     W  S  G  Q  Y  V  G  G  A  E  A  R  I  N  T  Q  W  L  L  T
   TGGTCTGGCCAATACGTTGGCGGTGCTGAGGCTCGTATCAACACTCAGTGGCTGTTAACA 1210      1220      1230      1240      1250      1260
     S  G  T  T  E  A  N  A  W  K  S  T  L  V  G  H  D  T  F  T
   TCCGGCACTACCGAAGCGAATGCATGGAAATCGACACTAGTAGGTCATGACACCTTTACC 1270      1280      1290
     K  V  K  P  S  A  A  S  *  *
   AAAGTTAAGCCTTCTGCTGCTAGCTAATAAGAATTC
                                 EcoRI
```

FIGURE 10B

```
              10        20         30         40         50         60
                                                    M   K   Y   L   L   P   T
AAGCTTGCATGCAAATTCTATTTCAAGGAGACAGTCATAATGAAATACCTATTGCCTACG
HindIIISphI             SD           /--------------------

70        80         90        100        110        120
   A   A   A   G   L   L   L   L   A   A   Q   P   A   M   A   Q   V   Q   L   Q
GCAGCCGCTGGATTGTTATTACTCGCTGCCCAACCAGCGATGGCCCAGGTGCAGCTGCAG
------pelB leader----------------------------/VH_NP  PstI 130       140        150        160        170        180
   Q   P   G   A   E   L   V   K   P   G   A   S   V   K   L   S   C   K   A   S
CAGCCTGGGGCTGAGCTTGTGAAGCCTGGGGCTTCAGTGAAGCTGTCCTGCAAGGCTTCT 190       200        210        220        230        240
   G   Y   T   F   T   S   Y   W   M   H   W   V   K   Q   R   P   G   R   G   L
GGCTACACCTTCACCAGCTACTGGATGCACTGGGTGAAGCAGAGGCCTGGACGAGGCCTT
                      CDR1

250       260        270        280        290        300
   E   W   I   G   R   I   D   P   N   S   G   G   T   R   Y   N   E   K   F   L
GAGTGGATTGGAAGGATTGATCCTAATAGTGGTGGTACTAAGTACAATGAGAAGTTCAAG
                                  CDR2

310       320        330        340        350        360
   S   K   A   T   L   T   V   D   K   P   S   S   T   A   Y   M   Q   L   S   S
AGCAAGGCCACACTGACTGTAGACAAACCCTCCAGCACAGCCTACATGCAGCTCAGCAGC 370       380        390        400        410        420
   L   T   S   E   D   S   A   V   Y   Y   C   A   R   Y   D   Y   Y   G   S   S
CTGACATCTGAGGACTCTGCGGTCTATTATTGTGCAAGATACGATTACTACGGTAGTAGC 430       440        450        460        470        480
   Y   F   D   Y   W   G   Q   G   T   T   L   T   V   S   S   G   G   G   G   S
TACTTTGACTACTGGGGCCAAGGGACCACGGTCACCGTCTCCTCAGGTGGAGGCGGTTCA
CDR3                              BstEII      /---(G4S)3-----

490       500        510        520        530        540
   G   G   G   G   S   G   G   G   G   S   Q   V   V   L   T   Q   E   S   A   L
GGCGGAGGTGGCTCTGGCGGTGGCGGATCCCAGGCTGTTGTGACTCAGGAATCTGCACTC
----------------------BamHI-/Vλ_J558L 550       560        570        580        590        600
   T   T   S   P   G   E   T   V   T   L   T   C   R   S   S   T   G   A   V   T
ACCACATCACCTGGTGAAACAGTCACACTCACTTGTCGCTCAAGTACTGGGGCTGTTACA
                                                              CDR1

610       620        630        640        650        660
   T   S   N   Y   A   N   W   V   Q   E   K   P   D   H   L   F   T   G   L   I
ACTAGTAACTATGCCAACTGGGTCCAAGAAAAACCAGATCATTTATTCACTGGTCTAATA 670       680        690        700        710        720
   G   G   T   N   N   R   A   P   G   V   P   A   R   F   S   G   S   L   I   G
GGTGGTACCAACAACCGAGCTCCAGGTGTTCCTGCCAGATTCTCAGGCTCCCTGATTGGA
     KpnI    CDR2    SstI 730       740        750        760        770        780
   D   K   A   A   L   T   I   T   G   A   Q   T   E   D   E   A   I   Y   F   C
GACAAGGCTGCCCTCACCATCACAGGGGCACAGACTGAGGATGAGGCAATATATTTCTGT
```

FIGURE 11A

```
          790          800          810          820          830          840
  A    L    W    Y    S    N    H    W    V    F    G    G    G    T    K    L    T    V    L    G
GCTCTATGGTACAGCAACCACTGGGTGTTCGGTGGAGGAACCAAACTGACTGTCCTAGGT
       CDR3

850          860          870          880          890          900
  L    E    A    P    A    A    A    P    A    E    A    G    I    T    G    T    W    Y    N    Q
CTCGAGGCACCTGCTGCCGCACCTGCCGAAGCTGGTATCACTGGCACCTGGTATAACCAA
  XhoI    /-Ala.Pro linker--/core streptavidin 910          920          930          940          950          960
  L    G    S    T    F    I    V    T    A    G    A    D    G    A    L    T    G    T    Y    E
CTGGGGTCGACTTTCATTGTGACCGCTGGTGCGGACGGAGCTCTGACTGGCACCTACGAA
        SalI 970          980          990         1000         1010         1020
  S    A    V    G    N    A    E    S    R    Y    V    L    T    G    R    Y    D    S    A    P
TCTGCGGTTGGTAACGCAGAATCCCGCTACGTACTGACTGGCCGTTATGACTCTGCACCT 1030         1040         1050         1060         1070         1080
  A    T    D    G    S    G    T    A    L    G    W    T    V    A    W    K    N    N    Y    R
GCCACCGATGGCTCTGGTACCGCTCTGGGCTGGACTGTGGCTTGGAAAAACAACTATCGT
                 KpnI 1090         1100         1110         1120         1130         1140
  N    A    H    S    A    T    T    W    S    G    Q    Y    V    G    G    A    E    A    R    I
AATGCGCACAGCGCCACTACGTGGTCTGGCCAATACGTTGGCGGTGCTGAGGCTCGTATC 1150         1160         1170         1180         1190         1200
  N    T    Q    W    L    L    T    S    G    T    T    E    A    N    A    W    K    S    T    L
AACACTCAGTGGCTGTTAACATCCGGCACTACCGAAGCGAATGCATGGAAATCGACACTA 1210         1220         1230         1240         1250         1260
  V    G    H    D    T    F    T    K    V    K    P    S    A    A    S    *    *
GTAGGTCATGACACCTTTACCAAAGTTAAGCCTTCTGCTGCTAGCTAATAAGAATTC
                                                             EcoRI
```

FIGURE 11B

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGCTGCAGCAGCCTGGGGCTGAGCTTGTGAAGCCTGGGGCT
TCAGTGAAGCTGTCCTGCAAGGCTTCTGGCTACACCTTCACCAGCTACTGG
ATGCACTGGGTGAAGCAGAGGCCTGGACGAGGCCTTGAGTGGATTGGAAGG
ATTGATCCTAATAGTGGTGGTACTAAGTACAATGAGAAGTTCAAGAGCAAG
GCCACACTGACTGTAGACAAACCTCCAGCACAGCCTACATGCAGCTCAGC
AGCCTGACATCTGAGGACTCTGCGGTCTATTATTGTGCAAGATACGATTAC
TACGGTAGTAGCTACTTTGACTACTGGGGCCAAGGGACCACGGTCACCGTC
TCCTCAGGTGGAGGCGGTTCAGGCGGAGGTGGCTCTGGCGGTGGCGGATCC
CAGGCTGTTGTGACTCAGGAATCTGCACTCACCACATCACCTGGTGAAACA
GTCACACTCACTTGTCGCTCAAGTACTGGGGCTGTTACAACTAGTAACTAT
GCCAACTGGGTCCAAGAAAAACCAGATCATTTATTCACTGGTCTAATAGGT
GGTACCAACAACCGAGCTCCAGGTGTTCCTGCCAGATTCTCAGGCTCCCTG
ATTGGAGACAAGGCTGCCCTCACCATCACAGGGGCACAGACTGAGGATGAG
GCAATATATTTCTGTGCTCTATGGTACAGCAACCACTGGGTGTTCGGTGGA
GGAACCAAACTGACTGTCCTAGGTCTCGAGATCAAGCGCAAGGAATCTGCA
GCTGCCAAGTTCGAGCGGCAGCACATGGACTCTGGCAACTCCCCAGCAGC
AGCTCCAACTACTGCAACCTGATGATGTGCTGCCGAAGATGACCCAGGGGA
AATGCAAGCCAGTGAACACCTTTGTGCATGAGTCCCTGGCCGATGTTAAGG
CCGTGTGCTCCCAGAAGAAAGTCACTTGCAAGAATGGGCAGACCAACTGCT
ACCAGAGCAAATCCACCATGCGCATCACAGACTGCCGCGAGACTGGCAGCT
CCAAGTACCCCAACTGCGCCTACAAGACCACCCAGGTGGAGAAACATCA
TAGTGGCTTGTGGCGGTAAACCGTCCGTGCCAGTCCACTTCGATGCTTCAG
TGTAGATCTCCACCTGAGGCCAGAACAGTGAATTC
```

FIGURE 21

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGGAGTCAGGACCTGGCCTGGTGGCGCCCTCACAGAGCCTG
TCCATCACATGCACTGTCTCAGGGTTCTCATTAACCAGTTATGGTGTAAGC
TGGGTTCGCCAGCCTCCAAGAAAGGGTCTGGAGTGGCTGGGAGTAATATGG
GAAGACGGGAGCACAAATTATCATTCACGTCTCATATCCAGACTGAGCATC
AACAAGGATAACTCCAAGAGCCAAGTTTTCTTAAAACTGAACAGTCTGCAA
ACTGATGACACAGCCACGTACTACTGTGCCAAACCCACTACGGTAGCAGC
AACGTGGGGCTATGGAATACTGGGGTCAAGGAACCTCGGTCACCGTCTCC
TCAGGTGGAGGCGGTTCAGGCGGAGGTGGCTCTGGCGGTGGCGGATCGGAC
ATCGAGCTCACCCAGTCTCCAGCCTCCCTAACTGCATCTGTGGGAGAAACT
GTCACCATCACCTGTCGAGCAAGTGAAAATATTTACAGTTATGTAGCATGG
TATCAGCAGAAACAGGGAAAATCTCCTCAGTTCCTGGTCTATAATGCAAAA
TCCTTAGCAGAGGGTGTGCCATCAAGGTTCAGTGGCAGTGGATCAGGCACA
CAGTTTTCTCTGAAGATCAACAGCCTGCAGCCTGAAATTTTGGGAATTAT
TACTGTCAACATCATTATGTTAGTCCGTGGACGTTCGGTGGAGGCACCAAG
CTCGAGATCAAGCGCAAGGAATCTGCAGCTGCCAAGTTCGAGCGGCAGCAC
ATGGACTCTGGCAACTCCCCAGCAGCAGCTCCAACTACTGCAACCTGATG
ATGTGCTGCCGAAGATGACCCAGGGGAAATGCAAGCCAGTGAACACCTTTG
TGCATGAGTCCCTGGCCGATGTTAAGGCCGTGCTCCCAGAAGAAAGTCA
CTTGCAAGAATGGGCAGACCAACTGCTACCAGAGCAAATCCACCATGCGCA
TCACAGACTGCCGCGAGACTGGCAGCTCCAAGTACCCAACTGCGCCTACA
AGACCACCCAGGTGGAGAAACACATCATAGTGGCTTGTGGCGGTAAACCGT
CCGTGCCAGTCCACTTCGATGCTTCAGTGTAGATCTCCACCTGAGGCCAGA
ACAGTGAATTC
```

FIGURE 22

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGCTGCAGGAGTCAGGACCTGGCCTGGTGGCGCCCTCACAG
ACGCTGTCCATCACATGCACCGTCTCAGGGTTCTCATTAACCGGCTATGGT
GTAAACTGGGTTCGCCAGCCTCCAGGAAAGGGTCTGGAGTGGCTGGGAATG
ATTTGGGGTGATGGAAACACAGACTATAATTCAGCTCTCAAATCCAGACTG
AGCATCAGCAAGGACAACTCCAAGAGCCAAGTTTTCTTAAAAATGAACAGT
CTGCACACTGATGACACAGCCAGGTACTACTGTGCCAGAGAGAGAGATTAT
AGGCTTGACTACTGGGGCCAAGGCACCACGGTCACCGTCTCCTCAGGTGGA
GGCGGTTCAGGCGGAGGTGGCTCTGGCGGTGGCGGATCGGACATCGTCATG
ACTCAGTCTCCAGCCTCCCTTTCTGCGTCTGTGGGAGAAACTGTCACCATC
ACATGTCGAGCAAGTGGGAATATTCACAATTATTTAGCATGGTATCAGCAG
AAACAGGGAAAATCTCCTCAGCTCCTGGTCTATTATACAACAACCTTAGCA
GATGGTGTGCCATCAAGGTTCAGTGGCAGTGGATCAGGAACACAATATTCT
CTCAAGATCAACAGCCTGCAGCCTGAAGATTTTGGGAGTTATTACTGTCAA
CATTTTTGGAGTACTCCTCGGACGTTCGGTGGAGGCACCAAGCTCGAGATC
AAGCGCAAGGAATCTGCAGCTGCCAAGTTCGAGCGGCAGCACATGGACTCT
GGCAACTCCCCCAGCAGCAGCTCCAACTACTGCAACCTGATGATGTGCTGC
CGAAGATGACCCAGGGGAAATGCAAGCCAGTGAACACCTTTGTGCATGAGT
CCCTGGCCGATGTTAAGGCCGTGTGCTCCCAGAAGAAAGTCACTTGCAAGA
ATGGGCAGACCAACTGCTACCAGAGCAAATCCACCATGCGCATCACAGACT
GCCGCGAGACTGGCAGCTCCAAGTACCCCAACTGCGCCTACAAGACCACCC
AGGTGGAGAAACACATCATAGTGGCTTGTGGCGGTAAACCGTCCGTGCCAG
TCCACTTCGATGCTTCAGTGTAGATCTCCACCTGAGGCCAGAACAGTGAAT
TC
```

FIGURE 23

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGCTGCAGCAGCCTGGGGCTGAGCTTGTGAAGCCTGGGGCT
TCAGTGAAGCTGTCCTGCAAGGCTTCTGGCTACACCTTCACCAGCTACTGG
ATGCACTGGGTGAAGCAGAGGCCTGGACGAGGCCTTGAGTGGATTGGAAGG
ATTGATCCTAATAGTGGTGGTACTAAGTACAATGAGAAGTTCAAGAGCAAG
GCCACACTGACTGTAGACAAACCTCCAGCACAGCCTACATGCAGCTCAGC
AGCCTGACATCTGAGGACTCTGCGGTCTATTATTGTGCAAGATACGATTAC
TACGGTAGTAGCTACTTTGACTACTGGGGCCAAGGGACCACGGTCACCGTC
TCCTCAGGTGGAGGCGGTTCAGGCGGAGGTGGCTCTGGCGGTGGCGGATCC
CAGGCTGTTGTGACTCAGGAATCTGCACTCACCACATCACCTGGTGAAACA
GTCACACTCACTTGTCGCTCAAGTACTGGGGCTGTTACAACTAGTAACTAT
GCCAACTGGGTCCAAGAAAACCAGATCATTTATTCACTGGTCTAATAGGT
GGTACCAACAACCGAGCTCCAGGTGTTCCTGCCAGATTCTCAGGCTCCCTG
ATTGGAGACAAGGCTGCCCTCACCATCACAGGGGCACAGACTGAGGATGAG
GCAATATATTTCTGTGCTCTATGGTACAGCAACCACTGGGTGTTCGGTGGA
GGAACCAAACTGACTGTCCTAGGTCTCGAGATTAAACGTATGCTTAAGATC
GCTGCTTTCAACATACGTACCTTCGGTGAATCTAAATGTCTAACGCTACG
CTAGCATCTTACATCGTACGCATCGTACGCCGTTACGATATCGTTCTGATC
CAGGAAGTTCGCGACTCTCACCTGGTTGCAGTTGGTAAACTTCTAGACTAC
CTGAACCAGGACGACCCGAACACCTACCACTACGTTGTTTCTGAACCCCTC
GGGCGTAACTCTTACAAAGAACGGTACCTGTTCCTGTTCCGTCCGAACAAA
GTTTCAGTACTGGATACCTACCAGTACGACGACGGATGCGAATCTTGCGGT
AACGACTCTTTCTCCCGGGAACCGGCTGTTGTTAAATTCTCGAGCCACTCT
ACCAAGGTTAAAGAGTTCGCTATCGTTGCTCTGCACAGCGCGCCGTCTGAC
GCTGTTGCTGAAATCAACTCTCTGTACGACGTTTACCTGGACGTTCAGCAG
AAATGGCACCTGAACGACGTCATGCTGATGGGTGACTTCAACGCTGACTGC
TCTTATGTAACCTCTTCTCAGTGGTCATCGATTCGTCTGCGCACCTCGTCG
ACCTTCCAGTGGCTGATCCCGGACTCCGCTGACACCACCGCTACTAGTACC
AACTGCGCTTACGACCGTATCGTTGTTGCTGGATCCCTGCTGCAGTCTTCT
GTTGTACCGGGTAGCGCGGCCCCGTTCGACTTCCAGGCTGCATATGGTCTT
TCGAACGAAATGGCGCTGGCCATCTCTGATCACTACCCGGTTGAGGTAACC
CTGACCTAATTCTAGA
```

FIGURE 24

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGGAGTCAGGACCTGGCCTGGTGGCGCCCTCACAGAGCCTG
TCCATCACATGCACTGTCTCAGGGTTCTCATTAACCAGTTATGGTGTAAGC
TGGGTTCGCCAGCCTCCAAGAAAGGGTCTGGAGTGGCTGGGAGTAATATGG
GAAGACGGGAGCACAAATTATCATTCACGTCTCATATCCAGACTGAGCATC
AACAAGGATAACTCCAAGAGCCAAGTTTTCTTAAAACTGAACAGTCTGCAA
ACTGATGACACAGCCACGTACTACTGTGCCAAACCCACTACGGTAGCAGC
AACGTGGGGCTATGGAATACTGGGGTCAAGGAACCTCGGTCACCGTCTCC
TCAGGTGGAGGCGGTTCAGGCGGAGGTGGCTCTGGCGGTGGCGGATCGGAC
ATCGAGCTCACCCAGTCTCCAGCCTCCCTAACTGCATCTGTGGGAGAAACT
GTCACCATCACCTGTCGAGCAAGTGAAATATTTACAGTTATGTAGCATGG
TATCAGCAGAAACAGGGAAAATCTCCTCAGTTCCTGGTCTATAATGCAAAA
TCCTTAGCAGAGGGTGTGCCATCAAGGTTCAGTGGCAGTGGATCAGGCACA
CAGTTTTCTCTGAAGATCAACAGCCTGCAGCCTGAAAATTTTGGGAATTAT
TACTGTCAACATCATTATGTTAGTCCGTGGACGTTCGGTGGAGGCACCAAG
CTCGAGATTAAACGTATGCTTAAGATCGCTGCTTTCAACATACGTACCTTC
GGTGAATCTAAAATGTCTAACGCTACGCTAGCATCTTACATCGTACGCATC
GTACGCCGTTACGATATCGTTCTGATCCAGGAAGTTCGCGACTCTCACCTG
GTTGCAGTTGGTAAACTTCTAGACTACCTGAACCAGGACGACCCGAACACC
TACCACTACGTTGTTTCTGAACCCCTCGGGCGTAACTCTTACAAAGAACGG
TACCTGTTCCTGTTCCGTCCGAACAAAGTTTCAGTACTGGATACCTACCAG
TACGACGACGGATGCGAATCTTGCGGTAACGACTCTTTCTCCCGGGAACCG
GCTGTTGTTAAATTCTCGAGCCACTCTACCAAGGTTAAAGAGTTCGCTATC
GTTGCTCTGCACAGCGCGCCGTCTGACGCTGTTGCTGAAATCAACTCTCTG
TACGACGTTTACCTGGACGTTCAGCAGAAATGGCACCTGAACGACGTCATG
CTGATGGGTGACTTCAACGCTGACTGCTCTTATGTAACCTCTTCTCAGTGG
TCATCGATTCGTCTGCGCACCTCGTCGACCTTCCAGTGGCTGATCCCGGAC
TCCGCTGACACCACCGCTACTAGTACCAACTGCGCTTACGACCGTATCGTT
GTTGCTGGATCCCTGCTGCAGTCTTCTGTTGTACCGGGTAGCGCGGCCCCG
TTCGACTTCCAGGCTGCATATGGTCTTTCGAACGAAATGGCGCTGGCCATC
TCTGATCACTACCCGGTTGAGGTAACCCTGACCTAATTCTAGA
```

FIGURE 25

```
AAGCTTGCATGCAAATTCTATTTCAAGGAGACAGTCATAATGAAATACCTA
TTGCCTACGGCAGCCGCTGGATTGTTATTACTCGCTGCCCAACCAGCGATG
GCCCAGGTGCAGCTGCAGGAGTCAGGACCTGGCCTGGTGGCGCCCTCACAG
ACGCTGTCCATCACATGCACCGTCTCAGGGTTCTCATTAACCGGCTATGGT
GTAAACTGGGTTCGCCAGCCTCCAGGAAAGGGTCTGGAGTGGCTGGGAATG
ATTTGGGGTGATGGAAACACAGACTATAATTCAGCTCTCAAATCCAGACTG
AGCATCAGCAAGGACAACTCCAAGAGCCAAGTTTTCTTAAAAATGAACAGT
CTGCACACTGATGACACAGCCAGGTACTACTGTGCCAGAGAGAGAGATTAT
AGGCTTGACTACTGGGGCCAAGGCACCACGGTCACCGTCTCCTCAGGTGGA
GGCGGTTCAGGCGGAGGTGGCTCTGGCGGTGGCGGATCGGACATCGTCATG
ACTCAGTCTCCAGCCTCCCTTTCTGCGTCTGTGGGAGAAACTGTCACCATC
ACATGTCGAGCAAGTGGGAATATTCACAATTATTTAGCATGGTATCAGCAG
AAACAGGGAAAATCTCCTCAGCTCCTGGTCTATTATCAACAACCTTAGCA
GATGGTGTGCCATCAAGGTTCAGTGGCAGTGGATCAGGAACACAATATTCT
CTCAAGATCAACAGCCTGCAGCCTGAAGATTTTGGGAGTTATTACTGTCAA
CATTTTTGGAGTACTCCTCGGACGTTCGGTGGAGGCACCAAGCTCGAGATT
AAACGTATGCTTAAGATCGCTGCTTTCAACATACGTACCTTCGGTGAATCT
AAAATGTCTAACGCTACGCTAGCATCTTACATCGTACGCATCGTACGCCGT
TACGATATCGTTCTGATCCAGGAAGTTCGCGACTCTCACCTGGTTGCAGTT
GGTAAACTTCTAGACTACCTGAACCAGGACGACCCGAACACCTACCACTAC
GTTGTTTCTGAACCCCTCGGGCGTAACTCTTACAAAGAACGGTACCTGTTC
CTGTTCCGTCCGAACAAAGTTTCAGTACTGGATACCTACCAGTACGACGAC
GGATGCGAATCTTGCGGTAACGACTCTTTCTCCCGGGAACCGGCTGTTGTT
AAATTCTCGAGCCACTCTACCAAGGTTAAAGAGTTCGCTATCGTTGCTCTG
CACAGCGCGCCGTCTGACGCTGTTGCTGAAATCAACTCTCTGTACGACGTT
TACCTGGACGTTCAGCAGAAATGGCACCTGAACGACGTCATGCTGATGGGT
GACTTCAACGCTGACTGCTCTTATGTAACCTCTTCTCAGTGGTCATCGATT
CGTCTGCGCACCTCGTCGACCTTCCAGTGGCTGATCCCGGACTCCGCTGAC
ACCACCGCTACTAGTACCAACTGCGCTTACGACCGTATCGTTGTTGCTGGA
TCCCTGCTGCAGTCTTCTGTTGTACCGGGTAGCGCGGCCCCGTTCGACTTC
CAGGCTGCATATGGTCTTTCGAACGAAATGGCGCTGGCCATCTCTGATCAC
TACCCGGTTGAGGTAACCCTGACCTAATTCTAGA
```

FIGURE 26

H17-BSRNase
(pSPH17BSR)

H17-BSRNaseKDEL
(pSPH17BSRKDEL)

H17-Link-BSRNaseKDEL
(pSPH17LBSRKDEL)

H17-Dip.Tox.-BSRNase
(pSPDTBSR)

H17-Dip.tox-BSRNase-
KDEL
(pSPH17DTBSRKDEL)

H17-Dip tox-
link-BSRNaseKDEL
(pSPH17DTLBSR
KDEL)

Key

ScFv H17E2

Bovine seminal RNase

Diptheria toxin disulphide loop

Linker

KDEL sequence

Fig. 28

```
ATGAAATACCTATTGCCTACGGCAGCCGCTGGATTGTTATTACTCGCTGCCCAACC
AGCGATGGCCCAGCTGCAGGAGTCAGGACCTGGCCTGGTGGCGCCCTCACAGAGCC
TGTCCATCACATGCACTGTCTCAGGGTTCTCATTAACCAGTTATGGTGTAAGCTGG
GTTCGCCAGCCTCCAAGAAAGGGTCTGGAGTGGCTGGGAGTAATATGGGAAGACGG
GAGCACAAATTATCATTCACGTCTCATATCCAGACTGAGCATCAACAAGGATAACT
CCAAGAGCCAAGTTTTCTTAAAACTGAACAGTCTGCAAACTGATGACACAGCCACG
TACTACTGTGCCAAACCCCACTACGGTAGCAGCAACGTGGGGGCTATGGAATACTG
GGGTCAAGGAACCTCGGTCACCGTCTCCTCAGGTGGAGGCGGTTCAGGCGGAGGTG
GCTCTGGCGGTGGCGGATCGGACATCGAGCTCACCCAGTCTCCAGCCTCCCTAACT
GCATCTGTGGGAGAAACTGTCACCATCACCTGTCGAGCAAGTGAAAATATTTACAG
TTATGTAGCATGGTATCAGCAGAAACAGGGAAAATCTCCTCAGTTCCTGGTCTATA
ATGCAAAATCCTTAGCAGAGGGTGTGCCATCAAGGTTCAGTGGCAGTGGATCAGGC
ACACAGTTTTCTCTGAAGATCAACAGCCTGCAGCCTGAAGATTTTGGGAATTATTA
CTGTCAACATCATTATGTTAGTCCGTGGACGTTCGGTGGAGGCACCAAGCTCGAGA
TCAAGCGCTCTAGCCTCGAAGGTGGGTGCGCTGGTAATAGAGTCAGAAGATCAGTC
GGAAGCAGCCTGTCTTGCGGTGGTCTCGACGTCGAGATCAAGCGCAAGGAATCTGC
AGCTGCCAAGTTCGAGCGGCAGCACATGGACTCTGGCAACTCCCCAGCAGCAGCT
CCAACTACTGCAACCTGATGATGTGCTGCCGGAAGATGACCCAGGGGAAATGCAAG
CCAGTGAACACCTTTGTGCATGAGTCCCTGGCCGATGTTAAGGCCGTGTGCTCCCA
GAAGAAAGTCACTTGCAAGAATGGGCAGACCAACTGCTACCAGAGCAAATCCACCA
TGCGCATCACAGACTGCCGCGAGACTGGCAGCTCCAAGTACCCAACTGCGCCTAC
AAGACCACCCAGGTGGAGAAACACATCATAGTGGCTTGTGGCGGTAAACCGTCCGT
GCCAGTCCACTTCGATGCTTCAGTGTAG
```

FIGURE 29

```
ATGAAATACCTATTGCCTACGGCAGCCGCTGGATTGTTATTACTCGCTGCCCAACC
AGCGATGGCCCAGCTGCAGGAGTCAGGACCTGGCCTGGTGGCGCCCTCACAGAGCC
TGTCCATCACATGCACTGTCTCAGGGTTCTCATTAACCAGTTATGGTGTAAGCTGG
GTTCGCCAGCCTCCAAGAAAGGGTCTGGAGTGGCTGGGAGTAATATGGGAAGACGG
GAGCACAAATTATCATTCACGTCTCATATCCAGACTGAGCATCAACAAGGATAACT
CCAAGAGCCAAGTTTTCTTAAAACTGAACAGTCTGCAAACTGATGACACAGCCACG
TACTACTGTGCCAAACCCCACTACGGTAGCAGCAACGTGGGGCTATGGAATACTG
GGGTCAAGGAACCTCGGTCACCGTCTCCTCAGGTGGAGGCGGTTCAGGCGGAGGTG
GCTCTGGCGGTGGCGGATCGGACATCGAGCTCACCCAGTCTCCAGCCTCCCTAACT
GCATCTGTGGGAGAAACTGTCACCATCACCTGTCGAGCAAGTGAAAATATTTACAG
TTATGTAGCATGGTATCAGCAGAAACAGGGAAGATCTCCTCAGTTCCTGGTCTATA
ATGCAAAATCCTTAGCAGAGGGTGTGCCATCAAGGTTCAGTGGCAGTGGATCAGGC
ACACAGTTTTCTCTGAAGATCAACAGCCTGCAGCCTGAAAATTTTGGGAATTATTA
CTGTCAACATCATTATGTTAGTCCGTGGACGTTCGGTGGAGGCACCAAGCTCGAGA
TCAAGCGCTCTAGCCTCGAAGGTGGGTGCGCTGGTAATAGAGTCAGAAGATCAGTC
GGAAGCAGCCTGTCTTGCGGTGGTCTCGACGTCGAGATCAAGCGCAAGGAATCTGC
AGCTGCCAAGTTCGAGCGGCAGCACATGGACTCTGGCAACTCCCCCAGCAGCAGCT
CCAACTACTGCAACCTGATGATGTGCTGCCGGAAGATGACCCAGGGGAAATGCAAG
CCAGTGAACACCTTTGTGCATGAGTCCCTGGCCGATGTTAAGGCCGTGTGCTCCCA
GAAGAAAGTCACTTGCAAGAATGGGCAGACCAACTGCTACCAGAGCAAATCCACCA
TGCGCATCACAGACTGCCGCGAGACTGGCAGCTCCAAGTACCCCAACTGCGCCTAC
AAGACCACCCAGGTGGAGAAACACATCATAGTGGCTTGTGGCGGTAAACCGTCCGT
GCCAGTCCACTTCGATGCTTCAGTGAAGGACGAACTGTAA
```

FIGURE 30

```
ATGAAATACCTATTGCCTACGGCAGCCGCTGGATTGTTATTACTCGCTGCCCAACC
AGCGATGGCCCAGCTGCAGGAGTCAGGACCTGGCCTGGTGGCGCCCTCACAGAGCC
TGTCCATCACATGCACTGTCTCAGGGTTCTCATTAACCAGTTATGGTGTAAGCTGG
GTTCGCCAGCCTCCAAGAAAGGGTCTGGAGTGGCTGGGAGTAATATGGGAAGACGG
GAGCACAAATTATCATTCACGTCTCATATCCAGACTGAGCATCAACAAGGATAACT
CCAAGAGCCAAGTTTTCTTAAAACTGAACAGTCTGCAAACTGATGACACAGCCACG
TACTACTGTGCCAAACCCCACTACGGTAGCAGCAACGTGGGGGCTATGGAATACTG
GGGTCAAGGAACCTCGGTCACCGTCTCCTCAGGTGGAGGCGGTTCAGGCGGAGGTG
GCTCTGGCGGTGGCGGATCGGACATCGAGCTCACCCAGTCTCCAGCCTCCCTAACT
GCATCTGTGGGAGAAACTGTCACCATCACCTGTCGAGCAAGTGAAAATATTTACAG
TTATGTAGCATGGTATCAGCAGAAACAGGGAAAATCTCCTCAGTTCCTGGTCTATA
ATGCAAAATCCTTAGCAGAGGGTGTGCCATCAAGGTTCAGTGGCAGTGGATCAGGC
ACACAGTTTTCTCTGAAGATCAACAGCCTGCAGCCTGAAGATTTTGGGAATTATTA
CTGTCAACATCATTATGTTAGTCCGTGGACGTTCGGTGGAGGCACCAAGCTCGAGA
TCAAGCGCTCTAGCCTCGAAGGTGGGTGCGCTGGTAATAGAGTCAGAAGATCAGTC
GGAAGCAGCCTGTCTTGCGGTGGTCTCGACGTCGAGATCAAGGCACCTGCTGCCTC
CCCGGCAGACGCTAAGGAATCTGCAGCTGCCAAGTTCGAGCGGCAGCACATGGACT
CTGGCAACTCCCCAGCAGCAGCTCCAACTACTGCAACCTGATGATGTGCTGCCGG
AAGATGACCCAGGGGAAATGCAAGCCAGTGAACACCTTTGTGCATGAGTCCCTGGC
CGATGTTAAGGCCGTGTGCTCCCAGAAGAAAGTCACTTGCAAGAATGGGCAGACCA
ACTGCTACCAGAGCAAATCCACCATGCGCATCACAGACTGCCGCGAGACTGGCAGC
TCCAAGTACCCCAACTGCGCCTACAAGACCACCCAGGTGGAGAAACACATCATAGT
GGCTTGTGGCGGTAAACCGTCCGTGCCAGTCCACTTCGATGCTTCAGTGAAGGACG
AACTGTAA
```

FIGURE 31

```
ATGAAATACCTATTGCCTACGGCAGCCGCTGGATTGTTATTACTCGCTGCCCAACC
AGCGATGGCCCAGCTGCAGGAGTCAGGACCTGGCCTGGTGGCGCCCTCACAGAGCC
TGTCCATCACATGCACTGTCTCAGGGTTCTCATTAACCAGTTATGGTGTAAGCTGG
GTTCGCCAGCCTCCAAGAAAGGGTCTGGAGTGGCTGGGAGTAATATGGGAAGACGG
GAGCACAAATTATCATTCACGTCTCATATCCAGACTGAGCATCAACAAGGATAACT
CCAAGAGCCAAGTTTTCTTAAAACTGAACAGTCTGCAAACTGATGACACAGCCACG
TACTACTGTGCCAAACCCCACTACGGTAGCAGCAACGTGGGGGCTATGGAATACTG
GGGTCAAGGAACCTCGGTCACCGTCTCCTCAGGTGGAGGCGGTTCAGGCGGAGGTG
GCTCTGGCGGTGGCGGATCGGACATCGAGCTCACCCAGTCTCCAGCCTCCCTAACT
GCATCTGTGGGAGAAACTGTCACCATCACCTGTCGAGCAAGTGAAAATATTTACAG
TTATGTAGCATGGTATCAGCAGAAACAGGGAAAATCTCCTCAGTTCCTGGTCTATA
ATGCAAAATCCTTAGCAGAGGGTGTGCCATCAAGGTTCAGTGGCAGTGGATCAGGC
ACACAGTTTTCTCTGAAGATCAACAGCCTGCAGCCTGAAGATTTTGGGAATTATTA
CTGTCAACATCATTATGTTAGTCCGTGGACGTTCGGTGGAGGCACCAAGCTCGAGA
TCAAGGCACCTGCTGCCTCCCCGGCAGACGCTAAGGAATCTGCAGCTGCCAAGTTC
GAGCGGCAGCACATGGACTCTGGCAACTCCCCAGCAGCAGCTCCAACTACTGCAA
CCTGATGATGTGCTGCCGGAAGATGACCCAGGGGAAATGCAAGCCAGTGAACACCT
TTGTGCATGAGTCCCTGGCCGATGTTAAGGCCGTGTGCTCCCAGAAGAAAGTCACT
TGCAAGAATGGGCAGACCAACTGCTACCAGAGCAAATCCACCATGCGCATCACAGA
CTGCCGCGAGACTGGCAGCTCCAAGTACCCAACTGCGCCTACAAGACCACCCAGG
TGGAGAAACACATCATAGTGGCTTGTGGCGGTAAACCGTCCGTGCCAGTCCACTTC
GATGCTTCAGTGAAGGACGAACTGTAA
```

FIGURE 32

```
ATGAAATACCTATTGCCTACGGCAGCCGCTGGATTGTTATTACTCGCTGCCCAACC
AGCGATGGCCCAGCTGCAGGAGTCAGGACCTGGCCTGGTGGCGCCCTCACAGAGCC
TGTCCATCACATGCACTGTCTCAGGGTTCTCATTAACCAGTTATGGTGTAAGCTGG
GTTCGCCAGCCTCCAAGAAAGGGTCTGGAGTGGCTGGGAGTAATATGGGAAGACGG
GAGCACAAATTATCATTCACGTCTCATATCCAGACTGAGCATCAACAAGGATAACT
CCAAGAGCCAAGTTTTCTTAAAACTGAACAGTCTGCAAACTGATGACACAGCCACG
TACTACTGTGCCAAACCCCACTACGGTAGCAGCAACGTGGGGGCTATGGAATACTG
GGGTCAAGGAACCTCGGTCACCGTCTCCTCAGGTGGAGGCGGTTCAGGCGGAGGTG
GCTCTGGCGGTGGCGGATCGGACATCGAGCTCACCCAGTCTCCAGCCTCCCTAACT
GCATCTGTGGGAGAAACTGTCACCATCACCTGTCGAGCAAGTGAAAATATTTACAG
TTATGTAGCATGGTATCAGCAGAAACAGGGAAAATCTCCTCAGTTCCTGGTCTATA
ATGCAAAATCCTTAGCAGAGGGTGTGCCATCAAGGTTCAGTGGCAGTGGATCAGGC
ACACAGTTTTCTCTGAAGATCAACAGCCTGCAGCCTGAAGATTTTGGGAATTATTA
CTGTCAACATCATTATGTTAGTCCGTGGACGTTCGGTGGAGGCACCAAGCTCGAGA
TCAAGCGCAAGGAATCTGCAGCTGCCAAGTTCGAGCGGCAGCACATGGACTCTGGC
AACTCCCCCAGCAGCAGCTCCAACTACTGCAACCTGATGATGTGCTGCCGGAAGAT
GACCCAGGGGAAATGCAAGCCAGTGAACACCTTTGTGCATGAGTCCCTGGCCGATG
TTAAGGCCGTGTGCTCCCAGAAGAAAGTCACTTGCAAGAATGGGCAGACCAACTGC
TACCAGAGCAAATCCACCATGCGCATCACAGACTGCCGCGAGACTGGCAGCTCCAA
GTACCCCAACTGCGCCTACAAGACCACCCAGGTGGAGAAACACATCATAGTGGCTT
GTGGCGGTAAACCGTCCGTGCCAGTCCACTTCGATGCTTCAGTGAAGGACGAACTG
TAA
```

FIGURE 33

COMPOUNDS FOR TARGETING

The present invention relates to compounds, some of which may be directly or indirectly cytotoxic combinations of compounds, that have a high avidity for, and can be targeted to, selected cells.

BACKGROUND OF THE PRIOR ART

The cell-specific targeting of compounds which are directly, or indirectly, cytotoxic has been proposed as a way to combat diseases such as cancer. Bagshawe and his co-workers have disclosed (Bagshawe (1987) *Br. J. Cancer* 56, 531; Bagshawe et al (1988) *Br. J. Cancer* 58, 700; WO 88/07378) conjugated compounds comprising an antibody or part thereof and an enzyme, the antibody being specific to tumour cell antigens and the enzyme acting to convert an innocuous pro-drug into a cytotoxic compound. The cytotoxic compounds were alkylating agents. eg a benzoic acid mustard released from para-N-bis(2-chloroethyl) aminobenzoyl glutamic acid by the action of Pseudomonas sp. CPG2 enzyme.

An alternative system using different pro-drugs has been disclosed (WO 91/11201) by Epenetos and co-workers. The cytotoxic compounds were cyanogenic monosaccharides or disaccharides, such as the plant compound amygdalin, which release cyanide upon the action of a β-glucosidase and hydroxynitrile lyase.

In a further alternative system, the use of antibody-enzyme conjugates containing the enzyme alkaline phosphatase in conjunction with the pro-drug etoposide 4'-phosphate or 7-(2'-aminoethyl phosphate)mitomycin or a combination thereof have been disclosed (EP 0 302 473; Senter et al (1988) *Proc. Natl. Acad. Sci. USA* 85, 4842).

Rybak and co-workers have disclosed (Rybak et al (1991) *J. Biol. Chem.* 266, 21202; WO 91/16069) the cytotoxic potential of a monomeric pancreatic ribonuclease when injected directly into *Xenopus oocytes* and the cytotoxic potential of monomeric RNase coupled to human transferrin or antibodies directed against the transferrin receptor. The monomeric RNase hybrid proteins were cytotoxic to human erythroleukaemia cells in vitro.

Other approaches are the in vivo application of streptavidin conjugated antibodies followed, after an appropriate period, by radioactive biotin (Hnatowich et al (1988) *J. Nucl. Med.* 29, 1428–1434), or injection of a biotinylated mAb followed by radioactive streptavidin (Paganelli et al (1990) *Int. J. Cancer* 45, 1184–1189). A pilot radioimmunolocalisation study in non-small cell lung carcinomas was conducted with encouraging results (Kalofonos et al (1990) *J. Nucl. Med.* 31, 1791–1796).

Apart from these examples, it is rather more common to see biotinylated antibodies and streptavidin-enzyme conjugates which are used in enzyme-linked immunosorbent assays.

These previous systems have used relatively large antibody-enzyme or antibody-streptavidin or antibody-biotin conjugates and may comprise portions of non-mammalian origin which are highly immunoreactive.

Rapid penetrance (Yokota et al (1992) *Cancer Res.* 52, 3402–3408) and rapid clearance (Colcher et al (1990) *J. Natl. Cancer Inst.* 82, 1191–1197) has been demonstrated for single chain Fv antibody fragments (ScFv).

In using the cell-specific reagents aforementioned in a therapeutically useful situation one of the requirements that needs to be met is for the cell-specific reagent to accumulate to a sufficiently higher level at the target cell than at other cells. A further requirement is that a directly or indirectly cytotoxic reagent is carried to the target cell, and it is preferred that the said cytotoxic reagent is of high potency.

We have now devised improved systems at least some of which exhibit higher avidities to the selected target cells, and make use of novel, potent directly or indirectly cytotoxic agents.

SUMMARY OF INVENTION

A first aspect of the invention provides a compound comprising a target cell-specific portion and a cytotoxic portion characterised in that the cytotoxic portion has nucleolytic activity.

Suitably, as disclosed below, the cytotoxic portion may have ribonucleolytic activity or it may have DNA endonucleolytic activity.

One aspect of the present invention provides a compound comprising a target cell-specific portion and a directly or indirectly cytotoxic portion, characterised in that the target cell-specific portion recognizes the target cell with high avidity.

A further aspect of the present invention provides a compound comprising a target cell-specific portion and a directly or indirectly cytotoxic portion characterised in that the cytotoxic portion is a sub-unit of an oligomer provided that, if the sub-unit is complexed with another sub-unit of the said oligomer then the said other sub-unit is the cytotoxic portion of a second compound of the invention.

A further aspect of the present invention provides a compound of at least two molecules each comprising a target cell-specific portion and a further portion wherein the molecules are complexed to one another via their further portions.

A further aspect of the present invention provides a compound comprising an oligomeric complex of at least two molecules each comprising a target cell-specific portion wherein the molecules are complexed to one another via their cytotoxic portions.

A further aspect of the present invention provides a compound comprising a target cell-specific portion and a directly or indirectly cytotoxic portion characterised in that the cytotoxic portion contains a binding site for a small-molecule wherein the said small-molecule binding site binds but does not modify catalytically the said small molecule.

A further aspect of the present invention provides a compound comprising a target cell-specific portion and a directly or indirectly cytotoxic portion characterised in that the target cell-specific portion comprises two or more binding sites for the target cell, wherein the target cell-specific portion is not an antibody, or bivalent fragment thereof, having respective arms which recognize the same entity as one another.

A further aspect of the present invention provides a compound comprising a target cell-specific portion and a cytotoxic portion characterised in that the cytotoxic portion has DNA endonucleolytic activity.

A further aspect of the invention provides a compound comprising a mediator portion and a directly or indirectly cytotoxic portion.

By "mediator portion" we mean the portion of the compound that recognizes a target cell-specific molecule. The target cell-specific molecule may be a further compound of any of the appropriate preceding aspects of the present invention or it may be a target cell-specific molecule known in the art or it may be a derivative thereof capable of recognition by the mediator portion.

By "high avidity" we mean that the target cell-specific portion recognizes the target cell with a binding constant of at least $K_d=10^{-9}$M, suitably $K_d=10^{-10}$M, more suitably $K_d=10^{-11}$M, more suitably still $K_d=10^{-12}$M, preferably $K_d=10^{-15}$M, more preferably $K_d=10^{-18}$M, more preferably still $K_d=10^{-21}$M, yet even more preferably $K_d=10^{-24}$M, and in further preference $K_d=10^{-27}$M or even $K_d=10^{-30}$M.

By "target cell specific" portion we mean the portion of the compound which comprises one or more binding sites which recognize and bind to entities on the target cell. The said entities are expressed predominantly, and preferably exclusively, on the said target cell. The target cell specific portion may contain one or more binding sites for different entities expressed on the same target cell type, or one or more binding sites for different entities expressed on two or more different target cell types.

By a "directly cytotoxic agent" we mean an agent which in itself is toxic to the cell if it is to reach, and preferably enter the said cell.

By an "indirectly cytotoxic agent" we mean an agent which in itself may or may not be non-toxic, but which can bind specifically to a cytotoxic compound, or can bind specifically to a compound which can be converted into a cytotoxic compound by the action of a further reagent.

The entity which is recognised may be any suitable entity which is expressed by tumour cells, virally-infected cells, pathogenic microorganisms, cells introduced as part of gene therapy or even normal cells of the body which, for whatever reason, one wishes to target, but which is not expressed, or at least not with such frequency, in cells which one does not wish to target. The entity which is recognised will often be an antigen. Examples of antigens include those listed in Table 1 below. Monoclonal antibodies which will bind to many of these antigens are already known (for example those given in the Table) but in any case, with today's techniques in relation to monoclonal antibody technology, antibodies can be prepared to most antigens. The antigen-specific portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

Chimaeric antibodies are discussed by Neuberger et al (1988, 8*th International Biotechnology Symposium* Part 2, 792–799).

Suitably prepared non-human antibodies can be "humanized" in known ways, for example by inserting the CDR regions of mouse antibodies into the framework of human antibodies.

The advantages of using antibody fragments, rather than whole antibodies, are several-fold. The smaller size of the fragments allows for rapid clearance, and may lead to improved tumour to non-tumour ratios. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Alternatively, the entity which is recognised may or may not be antigenic but can be recognised and selectively bound to in some other way. For example, it may be a characteristic cell surface receptor such as the receptor for melanocyte-stimulating hormone (MSH) which is expressed in high number in melanoma cells. The cell-specific portion may then be a compound or part thereof which specifically binds to the entity in a non-immune sense, for example as a substrate or analog thereof for a cell-surface enzyme or as a messenger.

Preferably, the high avidity target cell specific portion comprises two or more different binding sites for the target cell.

The different binding sites for the target cell may or may not be two or more different antibodies, or fragments thereof, which are directed to different entities expressed on the target cell. Alternatively, the different binding sites for the target cell may recognize and selectively bind the cell in some other, non-immune sense.

A further alternative is that one or more of the binding sites is an antibody, or part thereof, and that one or more of the binding sites for the target cell recognize and selectively bind the cell in some other, non-immune sense.

A compound which has binding sites for two or more target cell-specific entities may be more specific for binding to the said target cell, and a compound which has more than one of each of the different binding sites may bind to the said target cell with greater avidity. In combining two or more binding sites, which in themselves may be of high specificity but low affinity, it will be possible to generate in the compound of the invention a higher affinity for the target cell whilst retaining the specificity of the binding sites.

TABLE 1

| Antigen | Antibody | Existing Uses |
|---|---|---|
| 1. Tumour Associated Antigens | | |
| Carcino-embryonic Antigen | {C46 (Amersham) {85A12 (Unipath) | Imaging & Therapy of colon/rectum tumours. |
| Placental Alkaline Phosphatase | H17E2 (ICRF, Travers & Bodmer) | Imaging & Therapy of testicular and ovarian cancers. |
| Pan Carcinoma | NR-LU-10 (NeoRx Corporation) | Imaging & Therapy of various carcinomas incl. small cell lung cancer. |
| Polymorphic Epithelial Mucin (Human milk fat globule | HMFG1 (Taylor-Papadimitriou, ICRF) | Imaging & Therapy of ovarian cancer, pleural effusions. |
| Human milk mucin core protein | SM-3(IgG1)[1] | Diagnosis, Imaging & Therapy of breast cancer |
| β-human Chorionic Gonadotropin | W14 | Targeting of enzyme (CPG2) to human xenograft choriocarcinoma in nude mice. (Searle et al (1981) Br. J Cancer 44, 137–144) |
| A Carbohydrate on Human Carcinomas | L6 (IgG2a)[2] | Targeting of alkaline phosphatase. (Senter et al (1988) Proc. Natl. Acad. Sci. USA 85, 4842–4846 |
| CD20 Antigen on B Lymphoma (normal and neoplastic) | 1F5 (IgG2a)[3] | Targeting of alkaline phosphatase. (Senter et al (1988) Proc. Natl. Acad. Sci. USA 85, 4842–4846 |
| 2. Immune Cell Antigens | | |
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CDS) | H65 (Bodmer, Knowles ICRF, Licensed to Xoma Corp., USA) | Immunotoxin treatment of Acute Graft versus Host disease, Rheumatoid Arthritis. |
| 3. Infectious Agent-Related Antigens | | |
| Mumps virus-related | Anti-mumps polyclonal antibody | Antibody conjugated to Diphtheria toxin for treatment of mumps. |
| Hepatitis B Surface Antigen | Anti HBs Ag | Immunotoxin against Hepatoma. |

[1] Burchell et al (1987) Cancer Res. 47, 5476–5482
[2] Hellstrom et al (1986) Cancer Res. 46, 3917–3923
[3] Clarke et al (1985) Proc. Natl. Acad. Sci. USA 82, 1766–1770
Other antigens include alphafoetoprotein, Ca-125 and prostate specific antigen.

It is preferable that the two portions of the compound of the invention are produced as a fusion compound by recombinant DNA techniques whereby a length of DNA comprises respective regions encoding the two portions of the compound of the invention either adjacent one another or separated by a region encoding a linker peptide which does not destroy the desired properties of the compound. The benefits in making the compound of the invention using recombinant DNA techniques are several fold. Firstly, it enables a high degree of precision with which the two portions of the compound can be joined together. Secondly, the construction of compounds which are "hetero-oligomeric" can be controlled by the expression of the different recombinant DNA molecules encoding each of the different type of subunit of the "hetero-oligomer" in the same host cell.

By "hetero-oligomer" we mean those compounds in which two or more different cell-specific portions are joined to either the same or to different subunits which are capable of oligomerisation. The expression, in the same host cell of two compounds, A and B, each with different target cell specific portions but with a common second portion capable of oligomerisation will result in a mixed population of compounds. For example, if the common second portion is capable of dimerisation, three potential compounds will be produced: $A_2$, AB and $B_2$, in a ratio of 1:2:1, respectively.

The separation of the desired compound with each of the different cell specific portions, that is AB, can be achieved by two step affinity chromatography.

Application of the mixture of compounds to an affinity column specific for A will result in the binding of $A_2$ and AB. These compounds are eluted from this first column, and then applied to an affinity column specific for B. This will result in AB, but not $A_2$, being bound to the column. Finally, the desired product AB, can be eluted.

Of course, the order in which the affinity columns are used is not important.

The same principle of separating those compounds with two or more different binding sites can be applied to the purification of the desired compounds from mixtures of other hetero-oligomers.

Conceivably, the two portions of the compound may overlap wholly or partly.

The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued Apr. 3, 1984 to Rutter et al, 4,530,901 issued Jul. 23, 1985 to Weissman, 4,582,800 issued Apr. 15, 1986 to Crowl, 4,677,063 issued Jun. 30, 1987 to Mark et al, 4,678,751 issued Jul. 7, 1987 to Goeddel, 4,704,362 issued Nov. 3, 1987 to Itakura et al, 4,710,463 issued Dec. 1, 1987 to Murray, 4,757,006 issued Jul. 12, 1988 to Toole, Jr. et al, 4,766,075 issued Aug. 23, 1988 to Goeddel et al and 4,810,648 issued Mar. 7, 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

Those vectors that include a replicon such as a procaryotic replicon can also include an appropriate promoter such as a procaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his3, trp1, leu2 and ura3. Plasmids pRS413–416 are Yeast Centromere plasmids (YCps).

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Exemplary genera of yeast contemplated to be useful in the practice of the present invention are Pichia, Saccharomyces, Kluyveromyces, Candida, Torulopsis, Hansenula, Schizosaccharomyces, Citeromyces, Pachysolen, Debaromyces, Metschunikowia, Rhodosporidium, Leucosporidium, Botrvoascus, Sporidiobolus, Endomycopsis, and the like. Preferred genera are those selected from the group consisting of Pichia, Saccharomyces, Kluyveromyces, Yarrowia and Hansenula. Examples of Saccharomyces are *Saccharomyces cerevisiae, Saccharomyces italicus* and *Saccharomyces rouxii*. Examples of Kluyveromyces are *Kluyveromyces fragilis* and *Kluyveromyces lactis*. Examples of Hansenula are *Hansenula polymorpha, Hansenula anomala* and *Hansenula capsulata*. *Yarrowia lipolytica* is an example of a suitable Yarrowia species.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, and hybrid promoters involving hybrids of parts of 5' regulatory regions with parts of 5' regulatory regions of other promoters or with upstream activation sites (eg the promoter of EP-A-258 067).

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* AHD1 gene is preferred.

The present invention also relates to a host cell transformed with a polynucleotide vector construct of the present invention. The host cell can be either procaryotic or eucaryotic. Bacterial cells are preferred procaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658 and monkey kidney-derived COS-1 cells available from the ATCC as CRL 1650.

Transformation of appropriate cell hosts with a DNA construct of the present invention is accomplished by well known methods that typically depend on the type of vector used. With regard to transformation of procaryotic host cells, see, for example, Cohen et al, *Proc. Natl. Acad. Sci. USA*, 69: 2110 (1972); and Sambrook et al, *Molecular Cloning, A Laboratory Manual*, Cold Spring Harbor Laboratory, Cold Spring Harbor, N.Y. (1989). Transformation of yeast cells is described in Sherman et al, *Methods In Yeast Genetics, A Laboratory Manual*, Cold Spring Harbor, N.Y. (1986). The method of Beggs, *Nature*, 275: 104–109 (1978) is also useful. With regard to vertebrate cells, reagents useful in transfecting such cells, for example calcium phosphate and DEAE-dextran or liposome formulations, are available from Stratagene Cloning Systems, or Life Technologies Inc, Gaithersburg, Md. 20877, USA.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern, *J. Mol. Biol.*, 98: 503 (1975) or Berent et al, *Biotech.*, 3: 208 (1985). Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains the protein.

Nutrient media useful for culturing transformed host cells are well known in the art and can be obtained from several commercial sources.

Alternatively, the target-cell specific and second portions of the compound of the invention are linked together by any of the conventional ways of cross-linking polypeptides, such as those generally described in O'Sullivan et al *Anal. Biochem.* (1979) 100, 100–108. For example, the antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Some of the various compounds of the invention are illustrated diagrammatically in FIG. 1. C and D are the target cell-specific portions, and X is the cytotoxic portion. Of course, X may form higher order oligomers than those illustrated for example trimers, tetramers, pentamers, hexamers.

In FIG. 1(*a*) to 1(*d*) C and D are shown binding to entities on either the same, or different cells.

In one embodiment of the invention, C and D recognize different molecules on the same target cell wherein the molecules on the same target cell are not confined to that cell type but may occur on a few other cell types. In particular, C may recognize molecules on cell types I, II and III, whereas D may recognize molecules on cell types I, IV and V. Thus a compound of the invention comprising C and D as the target cell-specific portion will have greater specificity for cell type I compared with cell types II, III and IV. This aspect of the invention is particularly helpful, as there have been very few completely target cell-specific molecules discovered, whereas molecules which occur on a few cell types, and which are useful in this aspect of the invention, are well known. Such molecules are usually cell-surface antigens for which cross-reactive antibodies are known. Examples of such molecules are given in Table 2.

TABLE 2

| Antigen | Cell-type | Antibody |
|---------|-----------|----------|
| CD9 | Pre-B cells, monocytes, platelets | MM2/57 (IgG2b, mouse) |
| CALLA | Lymphoid progenitor cells, granulocytes | B-E3 (IgG2a, mouse) |
| CD13 | Myeloid monocytes, granulocytes | B-F10 (IgG1, mouse) |
| CD24 | B-cells, granulocytes | ALB-9 (IgG1, mouse) |
| CD61 | Platelets, megakaryocytes | PM 6/13 (IgG1, mouse) |

The antibodies described in Table 2 are generally available from Serotec, Oxford. OX5 1BR, UK.

Preferably, the cytotoxic portion of the compound of the invention is capable of oligomerisation. Attachment of the target-cell specific portion to a cytotoxic portion capable of oligomerisation provides a method for increasing the number of binding sites to the target cell. For example, if the target cell-specific portion is joined to a portion capable of forming a dimer then the number of target cell-specific binding sites is two; if the target cell-specific portion is joined to a portion capable of forming a tetramer then the number of target cell-specific binding sites is four. The number of target cell-specific binding sites is greater than one and the compounds may therefore have a greater avidity for the target cell than do compounds which only have one target cell-specific binding site.

It is preferable for the cytotoxic portion of the compound of the invention capable of oligomerisation to contain no interchain disulphide bonds nor intrachain disulphide bonds; to be well characterised; to be non-toxic; to be stable; to be amenable to preparation in a form suitable for pre-clinical or clinical use or be in pre-clinical or clinical use; and for the subunit monomers to have a high affinity for each other, that is they contain one or more subunit binding sites.

Preferably, each subunit of the cytotoxic portion of the compound of the invention contains a binding site for a small molecule, the small molecule being capable of being conjugated to any from the following compounds: radioactive compound; spin-labelled compound; drug; pro-drug; radionuclide; protein including enzyme; antibody; or toxin.

In a preferred embodiment of the invention, the cytotoxic portion is streptavidin. Streptavidin is a homotetrameric molecule of $M_r$=60000 (subunit $M_r$=15000) and is produced by Streptomvces. Streptavidin binds four molecules of the water-soluble vitamin biotin with high specificity and affinity ($K_d$=10$^{-15}$M) although isolated subunits possess a very much lower affinity for biotin ($K_d$=10$^{-8}$M). Each subunit of streptavidin has a tightly-packed "core", with relatively unstructured amino- and carboxyl-terminal extensions. These extensions are believed to contribute to the formation of higher order aggregates of streptavidin. Many commercial forms of streptavidin are extensively proteolysed, have lost their unstructured extensions, and form stable tetramers (Bayer et al (1989) *Biochem J*. 259, 369–376; Bayer et al (1990) *Methods Enzymol*. 184, 51–67). The mature form of the protein has been the subject of recent research and is becoming increasingly well characterised (Gitlin et al (1988) *Biochem J*. 256, 279–282; Gitlin et al (1990) *Biochem J*. 269, 527–530; Sano & Cantor (1990) *J. Biol. Chem*. 265, 3369–3373) and the gene has been cloned and sequenced (Argarana et al (1986) *Nucl. Acids Res*. 14, 1871–1872) and expressed in *E. coli* (Sano & Cantor (1990) *Proc. Natl. Acad. Sci. USA* 87, 142–146). A modified form of the gene is available commercially from British Bio-technology Ltd, Oxford, UK.

Of course, for the invention to work the cytotoxic portion may comprise intact streptavidin, or it may comprise a fragment or fragments of streptavidin retaining at least the biotin- and subunit-binding sites.

Of course, the cytotoxic portion may comprise other molecules which bind biotin with high affinity, such as intact avidin, or it may comprise a fragment or fragments of avidin retaining at least the biotin- and subunit-binding sites. A comparison of avidin and streptavidin is made in Table 3. As avidin is naturally glycosylated, then it may be desirable to express the DNA encoding the compound of the invention in a eukaryotic cell such as yeast, mammalian or insect cell.

|  | Avidin | Streptavidin |
| --- | --- | --- |
| Source | Tissues and egg-whites of birds, reptiles and amphibia | *Streptomyces avidinii* |
| Glycoprotein | yes | no |
| pI | 10 | 5 |
| $M_r$ (subunit) | 67,000 | 60,000 |
| Oligomeric state | Tetramer | Tetramer |

By "subunit-binding sites" we mean those parts of the monomers that are necessary for the monomers to combine with one or more other monomers to produce an oligomer.

Biotin has an extremely high affinity for streptavidin ($K_d$=10$^{-15}$M) and at the same time is small enough to diffuse rapidly through most tissues in the body. Some of the biotin conjugates useful in the invention are known in the art, and it is preferred that the biotin is conjugated via a flexible linker arm to reduce any steric hindrance to the binding of the biotin portion of the conjugate to streptavidin or avidin.

Examples of biotin conjugates useful in the invention are biotinylated growth factors and cytokines such as TNFα-biotin and EGF-biotin which are generally available from Boehringer Mannheim, Mannheim, Germany, and biotin-alkaline phosphatase, biotin-fluorescein, biotin-peroxidase and other conjugates generally available from Calbiochem-Novabiochem, Nottingham, UK. Activated biotin reagents, suitable for conjugating to other molecules, are generally available from Fluka, Buchs, Switzerland.

In a second preferred embodiment of the invention, the cytotoxic portion is a dimeric compound with ribonucleolytic activity, such as a ribozyme, but preferably ribonuclease (RNase). The enzymes of the RNase family are able to degrade single-stranded RNA molecules to smaller polynucleotides and are directly cytotoxic when intracellular. Bovine seminal RNase (BSRNase) has activities in addition to its RNA-degrading activity, namely anti-tumour (Vescia et al (1980) *Cancer Res*. 40, 3740–3744; Vescia & Tramontano (1981) *Mol. Cell. Biochem*. 36, 125–128); immunosuppressive (Tamburrini et al (1990) *Eur. J. Biochem*. 190, 145–148; activation by interferon-γ (Schein et al (1990) *Nucl. Acids Res*. 18, 1057) and anti-spermatogenic (Doital & Matonsek (1973) *J. Reprod. Fertil*. 33, 263–274). BSRNase is a dimer and forms two unique disulphide bridges across the subunit interface (Piccoli et al (1988) *Biochem J*. 253, 329–336). The cDNA encoding the precursor to BSRNase can be prepared using the methods disclosed by Preub et al (1990) *FEBS Lett*. 270, 229–232.

Of course, for the invention to work the cytotoxic portion may comprise intact BSRNase, or it may comprise a fragment or fragments of BSRNase retaining at least the active site and subunit-binding sites.

It is further preferred if the fusion with the RNase comprises the sequence KDEL (SEQ ID No 29) at, or near to, the C-terminus of the protein.

It is still further preferred if a linker sequence is present at the N-terminus of the RNase to allow the N-terminus to be more flexible and increase the likelihood of dimer formation.

Preferably, a disulphide-loop-containing sequence which allows an RNase to be linked to a ScFv via a disulphide bond is present in a fusion protein.

In one embodiment the invention, the cytotoxic portion is a compound with DNA endonucleolytic activity such as copper-phenanthroline adducts but preferably is a DNA endonuclease, for example deoxyribonuclease-I (DNase-I), which is an endonuclease which cleaves double-stranded DNA to yield 5' phosphorylated polynucleotides. It does not cut all DNA sites with the same frequency as it is affected by the local structure of the DNA (specifically, the size of the minor groove).

Alternatively, the DNA endonuclease could be a type II restriction endonuclease. Type II restriction endonucleases are enzymes isolated from microorganisms, usually bacteria, which cleave double-stranded DNA at specific sequences. Typically, the type II restriction endonucleases recognize palindromic sequences in DNA and cleave both strands of the DNA within or adjacent the recognition site. Type II restriction enzymes are dimers of identical subunits, and, for example, EcoRI is a homodimer of 31 kDa subunits which recognizes the sequence 5'-GAATTC-3'.

Other type II restriction enzymes recognize different hexonucleotide sequences, for example BamHI recognizes 5'-GGATCC-3', HindIII recognizes 5'-AAGCTT-3'. In addition, type II restriction enzymes which recognize different numbers of bases are known, for example, MspI recognizes 5'-CCGG-3', Sau3AI recognizes 5'-GATC-3', HinfI recognizes 5'-GANTC-3' and NotI recognizes 5'-GCGGCCGC-3'. Of course, the fewer specific bases in the recognition sequence, the more likely that any DNA molecule will be cleaved by the cognate type II endonuclease.

The gene for the bovine DNase I has been chemically synthesized and expressed in E. coli (Worrall & Connolly (1990) J. Biol. Chem. 265, 21889–21895. The gene for the human enzyme has been cloned, from a human pancreatic cDNA library constructed in λgt10 and the enzyme has been expressed in human cell culture and used in the relief of cystic fibrosis symptoms, by reducing the viscosity of sputum, by degrading the viscous DNA (Shak et al (1990) Proc. Natl. Acad. Sci. 87, 9188–9192; Hubbard et al (1992) N. Engl. J. Med. 326, 812–815). All the enzymes are compact, monomeric proteins of about 29 kDa (260 amino acids); when glycosylated the human enzyme is about 35 kDa. It is dependent on divalent cations for activity ($Ca^{2+}$, $Mg^{2+}$). The human enzyme is about 75% identical to the bovine enzyme, at the amino acid sequence level. The synthetic gene encoding the bovine DNase-I can be prepared using the methods disclosed by Worrall & Connolly (1990) loc. cit.

The enzyme from bovine pancreas has been purified and crystallized, and a high resolution structure determined at 2 Å (Suck & Oefner (1986) J. Mol. Biol. 192, 605–632).

One aspect of the invention is the introduction into the targeted cell of the DNAse I enzyme. During stages of mitosis, when the nuclear membrane is dissolved, the chromosomal DNA of the said targeted cell will be susceptible to nuclease attack. In this embodiment of the invention DNAse I will be particularly cytotoxic to rapidly dividing cells, such as tumour cells.

A further aspect of the invention is the incorporation into the compound of the invention a nuclear localisation sequence from the SV40 large T antigen (Kalderon et al (1984) Cell 39, 499–509). The said nuclear localisation sequence is PKKKRKV (SEQ ID No 1), or analogues thereof, and a DNA fragment encoding the said sequence, or analogues thereof, may or may not be incorporated into the gene expressing the compound of the invention containing DNAse I as the second portion.

Inclusion of the said nuclear localisation sequence will allow the compound of the invention to gain access to the chromosomal DNA during the periods of the cell cycle when the nuclear membrane is intact, as the nuclear pores are permeable to large macromolecules incorporating the said nuclear localisation sequence, or analogues thereof.

For the invention to work, of course, the cytotoxic portion may comprise a fragment of RNase or of DNA endonuclease which retain their enzymatic activity, such as the active site, and in the case of the dimeric RNase, and restriction endonuclease, their subunit binding site.

A further aspect of the invention is that the RNase and the DNase are of mammalian, preferably human, origin. The use of the said mammalian proteins as the second, functional portion of the compound of the invention is advantageous as such compounds are less likely to give rise to undesirable immune reactions.

Many target cell-specific molecules are known, such as those disclosed in Table 1, which are not joined to a further directly or indirectly cytotoxic portion, but may nevertheless be useful in directing cytotoxic agents to a target cell.

Thus in a further aspect of the invention a compound comprises a mediator portion and a directly or indirectly cytotoxic portion. The mediator may recognize the native target cell-specific molecule, but it is preferable for the mediator to recognize a derivative of the said molecule.

In the case of antibodies, the native target cell-specific molecule may be recognised by the mediator via its Fc portion.

The said derivative may be made by joining a moiety, such as a small molecule, for example a hapten, to the said molecule, and may be recognised, if the mediator is, for example, an antibody or fragment thereof.

The advantage in using this method is that the same moiety may be joined to all types of target cell-specific molecules, and then only one compound, comprising a mediator which recognizes the said moiety and a directly or indirectly cytotoxic portion, may be used to deliver the cytotoxic agent to the target cell.

In one embodiment of the invention the mediator is $ScFV_{NP}$, and the moiety recognised by the said $ScFV_{NP}$ is the hapten 4-hydroxy-3-nitrophenylacetic acid (NP) or 4-hydroxy-3-iodophenylacetic acid, and the target cell-specific molecule is an antibody.

Other haptens are suitable as are other molecules, such as peptides, that can be recognised by the mediator. Conveniently the peptide is the core mucin peptide.

Before such molecules can be regarded as suitable candidates, there is a requirement that cell specificity be demonstrated and a further requirement that this specificity be shown to be conferred only by the combination of the interaction of the primary targeting antibody with target, and the interaction of the second step reagent (in this case the ScFv) with the primary antibody. To this end, the primary antibody needs to be recognised specifically by the mediator, and therefore requires stable modifications that will distinguish it from native antibodies. Multiple derivatisation of the primary antibody with a hapten fulfils this demand, and has the further advantage of amplification, providing an array of secondary targets for the mediator.

Of course, other mediators such as Fab, $F(ab')_2$, dAbs or other antibody fragments may be used. The mediator may also recognize the moiety in a non-immune sense, such as in biotin-streptavidin recognition. It is preferred if the moiety recognised is a small molecule, but the moiety may also be a polypeptide, peptide, oligosaccharide or the like.

The murine immune response to the haptens 4-hydroxy-3-nitrophenylacetic acid (NP) and 4-hydroxy-3-iodo-5-nitrophenylacetic acid (NIP) is dominated by well characterised $V_H$ domains and a $\lambda_1$ light chain (Kabat et al (1987) Sequences of proteins of immunological interest, US Department of Health and Human Services, Public Health Services, National Institutes of Health). NP-specific $V_H$ domains have been used in the construction of recombinant antibodies (Neuberger et al (1984) Nature 312, 604–608, Casedei et al (1990) Proc. Natl. Acad. Sci. USA 87, 2047–2051). The hapten itself is well studied and of some immunological interest (Brownstone et al (1966) loc. cit.) and is also available commercially in a variety of chemical forms. It is relatively simple to conjugate NP or NIP to other proteins including antibodies.

We describe in the Examples the construction and characterisation of a ScFv with an affinity in the range of 1–3×$10^8$ $M^{-1}$ at pH 7.4 for NIP conjugated to BSA, sufficiently high that the molecule is suitable as a second step targeting reagent. Derivatisation with hapten resulted in reduction in immunoreactivity of the primary antibody, but even under these adverse circumstances the hapten-conjugated antibody was still capable of delivering $ScFv_{NP}$ specifically to cells. Since about forty hapten molecules were conjugated, on average, to each mAb molecule, there is still a potential 40-fold amplification provided. The specificity of targeting is governed by the interactions of primary antibody with target, and the ScFv$_{NP}$ with derivatised primary antibody, since the ScFv does not bind cells and non-derivatised antibodies bound at cells cannot capture the ScFv. The ScFv described here can therefore be considered as a universal agent for delivery of drugs or radionuclides or other cytotoxic agents to any cell type for which a previously characterised antibody exists.

In this aspect of the invention, the cytotoxic portion joined to the mediator portion may be a drug, pro-drug, radionuclide, protein including an enzyme, antibody or any other therapeutically useful reagent.

Thus, the drug may be a cytotoxic chemical compound such as methotrexate, adriamicin, vinca alkaloids (vincristine, vinblastine, etoposide), daunorubicin or other intercalating agents. The enzyme, or enzymatic portion thereof, may be directly cytotoxic, such as DNaseI or RNase, or indirectly cytotoxic such as an enzyme which converts a substantially non-toxic pro-drug into a toxic form. The protein may be ricin. The cytotoxic portion may comprise a highly radioactive atom, such as iodine-131, rhenium-186, rhenium-188 or yttrium-90, which emits enough energy to destroy neighboring cells.

An indirectly cytotoxic portion may be a small-molecule binding site wherein the said small-molecule is capable of being conjugated to any from the following cytotoxic compounds: radioactive compound; drug; pro-drug; radionuclide; protein including enzyme; antibody; or toxin.

We hereby disclose the principle that ScFvs are suitable for indirect targeting. Moderating the degree of derivatisation of the primary antibody will reduce the loss of immunoreactivity of the primary antibody whilst still maintaining an array of secondary targets for the hapten-specific ScFv.

In a further embodiment, the cytotoxic portion of the compound comprises at least the biotin-binding portion of streptavidin as disclosed in Example 4.

The compounds of the invention are administered in any suitable way, usually parenterally, for example intravenously, intraperitoneally or, preferably (for bladder cancer), intravesically (ie into the bladder), in standard sterile, non-pyrogenic formulations of diluents and carriers, for example isotonic saline (when administered intravenously).

A further aspect of the invention provides a method of delivery of the compound of the invention which contains a binding site for a small molecule, and the administration of the said small molecule conjugated with any from the following: drug, pro-drug, radionuclide, enzyme, antibody or any other therapeutically useful reagent, to give the "small molecule conjugate".

Once the compound has bound to the target cells and been cleared from the bloodstream (if necessary), which typically takes a day or so, the small molecule conjugate is administered, usually as a single infused dose. If needed, because the compound of the invention may be immunogenic, cyclosporin or some other immunosuppressant can be administered to provide a longer period for treatment but usually this will not be necessary.

The timing between administrations of the compound and the small molecule conjugate may be optimised in a non-inventive way since target cell/normal tissue ratios of conjugate (at least following intravenous delivery) are highest after about 4–6 days, whereas at this time the absolute amount of antibody bound to the tumour, in terms of percent of injected dose per gram, is lower than at earlier times. Therefore, the optimum interval between administration of the conjugate and the small molecule conjugate will be a compromise between peak target concentration of enzyme and the best distribution ratio between target and normal tissues.

The dosage of the small molecule conjugate will be chosen by the physician according to the usual criteria. The dosage of the compound of the invention will similarly be chosen according to normal criteria, and, in the case of tumour treatment, particularly with reference to the type, stage and location of the tumour and the weight of the patient. The duration of treatment will depend in part upon the rapidity and extent of any immune reaction to the antibody or cytotoxic component of the compound.

A further aspect of the invention provides a method of delivery of the target cell-specific molecule and a compound of the invention which contains a mediator portion. Once the target cell-specific molecule has bound to the target cells and been cleared from the bloodstream (if necessary), which typically takes a day or so, the compound comprising a mediator portion is administered in any suitable way.

If the cytotoxic portion, joined to the mediator portion, contains a binding site for a small molecule, then, once the mediator-containing compound has bound to the target cell-specific molecule at the site of the target cell, and has been cleared from the bloodstream (if necessary), the said small molecule conjugate is administered as described supra.

The compounds of the invention either in themselves, or together with a target cell-specific molecule or additionally together with an appropriate toxic agent, capable of binding to the small molecule-binding site of the compound, are in principle suitable for the destruction of cells in any tumour or other defined class of cells selectively exhibiting a recognisable (surface) entity. The compounds are principally intended for human use but could be used for treating other mammals including dogs, cats, cattle, horses, pigs and sheep.

The small molecule conjugate, when used in combination with a compound for diagnosis, usually comprises a radioactive atom for scintigraphic studies, for example technetium 99m ($^{99m}$Tc) or iodine-123 ($^{123}$I), or a spin label for nuclear magnetic resonance (nmr) imaging (also known as magnetic resonance imaging, mri), such as iodine-123 again, iodine-131, indium-111, fluorine-19, carbon-13, nitrogen-15, oxygen-17, gadolinium, manganese or iron.

When used in combination with a compound for selective destruction of the tumour, the small molecule conjugate may comprise a highly radioactive atom, such as iodine-131, rhenium-186, rhenium-188 or yttrium-90, which emits enough energy to destroy neighboring cells, or a cytotoxic chemical compound such as methotrexate, adriamicin, vinca alkaloids (vincristine, vinblastine, etoposide), daunorubicin and other intercalating agents or (preferably) an enzyme or enzymatic portion thereof which converts a non-toxic pro-drug into a toxic form. In the latter case. the compound of the invention is administered and, once there is an optimum balance between (i) the tumour to normal cell ratio of compound and (ii) the absolute level of compound associated with the tumour, the pro-drug is administered either systemically (eg intravenously) or intravesically, into the bladder. The enzyme/pro-drug systems of Bagshawe and his co-workers may be used (loc. cit.) or the antibody-alkaline phosphatase conjugates, followed by etoposite phosphate (loc. cit.) or, more preferably, the cyanide-liberating systems described by Epenetos (loc. cit.).

The compounds of the invention, together with an appropriate small molecule conjugated to a readily-detectable reagent such as a radionuclide; fluorescent molecule; or enzyme are in principle suited for the recognition of antigens in other situations. These include immunoblotting procedures, such as the well-known Western blot (Towbin et al (1979) *Proc. Natl. Acad. Sci. USA* 76, 4350–4354); assays such as the enzyme-linked immunosorbent assay (ELISA); and in situ hybridisation experiments in which the presence of antigens within fixed cells is detected.

In a further embodiment of the invention, a compound comprising an oligomeric complex of at least two molecules each comprising a target cell-specific portion and a further portion wherein the molecules are complexed to one another via their further portions is useful in agglutinating cells. In a preferred embodiment the target cell-specific portion of the compound of the invention recognizes particular blood group antigens displayed on the surface of the erythrocyte, and because of the multivalent binding nature of the compound, the addition of the compound to blood may lead to haemagglutination. Thus, in this embodiment the compounds may be specific to particular antigens within the ABO, Rhesus, Kell, or any other blood group systems, and the compound of the invention may find uses in blood group typing or other areas of tissue typing.

Antibodies, including monoclonal antibodies, are known which react with most of the aforementioned blood group antigens and it is well within the scope of a person skilled in the art to derive, for example, ScFvs from such antibodies for use in the invention.

The invention will now be described in detail with reference to the following figures and examples wherein:

FIG. 1(*a*), 1(*b*), 1(*c*), and 1(*d*) show diagrammatic representations of compounds in accordance with the invention.

FIG. 3 shows oligonucleotide primers used in the polymerase chain reaction to amplify various fragments of the ScFv coding region.

FIG. 4A and FIG. 4B show the nucleotide sequence (SEQ ID No 2) (and encoded protein sequence (SEQ ID No 3)) between the HindIII and EcoRI sites of pRAS107 and pRAS111.

FIG. 9A and FIG. 9B show the nucleotide sequence (SEQ ID No 4) (and deduced amino acid sequence (SEQ ID No 5)) between the HindIII and EcoRI sites of pRAS108 and pRAS112.

FIG. 10A and 10B show the nucleotide sequence (SEQ ID No 6) (and deduced amino acid sequence (SEQ ID No 7)) between the HindIII and EcoRI sites of pRAS109 and pRAS113.

FIG. 11A and 11B show the nucleotide sequence (SEQ ID No 8) (and deduced amino acid sequence (SEQ ID No 9)) between the HindIII and EcoRI sites of pRAS110 and pRA114.

FIG. 21 shows the nucleotide sequence (SEQ ID No 10) of the ScFv-BSRNase fusion (anti-4-OH-nitrophenacetyl antibody) that has been inserted between the HindIII and EcoRI sites of plasmid pSP71.

FIG. 22 shows the nucleotide sequence (SEQ ID No 11) of the ScFv-BSRNase fusion (H17-BSRNase; anti-human placental alkaline phosphatase antibody; H17E2) that has been inserted between the HindIII and EcoRI sites of plasmid pSP71.

FIG. 23 shows the nucleotide sequence (SEQ ID No 12) of the ScFv-BSRNase fusion (anti-lysozyme antibody) that has been inserted between the HindIII and EcoRI sites of a plasmid pUC18.

FIG. 24 shows the nucleotide sequence (SEQ ID No 13) of the ScFv-DNaseI fusion (anti-4-OH nitrophenacetyl antibody) that has been inserted between the HindIII and BglI sites of plasmid pSP71.

FIG. 25 shows the nucleotide sequence (SEQ ID No 14) of the ScFv-DNaseI fusion (anti-human placental alkaline phosphatase antibody; H17E2) that has been inserted between the HindIII and BglI sites of plasmid pSP71.

FIG. 26 shows the nucleotide sequence (SEQ ID No 15) of the ScFv-DNaseI fusion (anti-lysozyme antibody) that has been inserted between the HindIII and BglI sites of plasmid pUC18.

FIG. 28 is a schematic diagram of the H17E2 scFv-seminal RNase fusion proteins. The plasmid which express them are named in parentheses.

FIG. 29 shows the nucleotide sequence (SEQ ID No 24) encoding the H17E2 scFv-diptheria toxin disulphide loop-BSRNase (H17-Dip. Tox.-BSRNase).

FIG. 30 shows the nucleotide sequence (SEQ ID No 25) encoding the H17E2 scFv-diptheria toxin disulphide loop-BSRNase-KDEL (H17-Dip. Tox.-BSRNase KDEL).

FIG. 31 shows the nucleotide sequence (SEQ ID No 26) encoding the H17E2 ScFv diptheria toxin disulphide loop-Linker-BSRNase-KDEL (H17-Dip. Tox.-link-BSRNase KDEL).

FIG. 32 shows the nucleotide sequence (SEQ ID No 27) encoding the H17E2 ScFv-Linker-BSRNase-KDEL (H17-LBSRNase-KDEL).

FIG. 33 shows the nucleotide sequence (SEQ ID No 28) encoding the H17E2 ScFv-BSRNase KDEL).

EXAMPLE 1

Construction of a Single-chain Fv (ScFv) Reactive Against the Hapten NP (4-OH Nitrophenacetyl)

Plasmid Constructions

Figure 2:
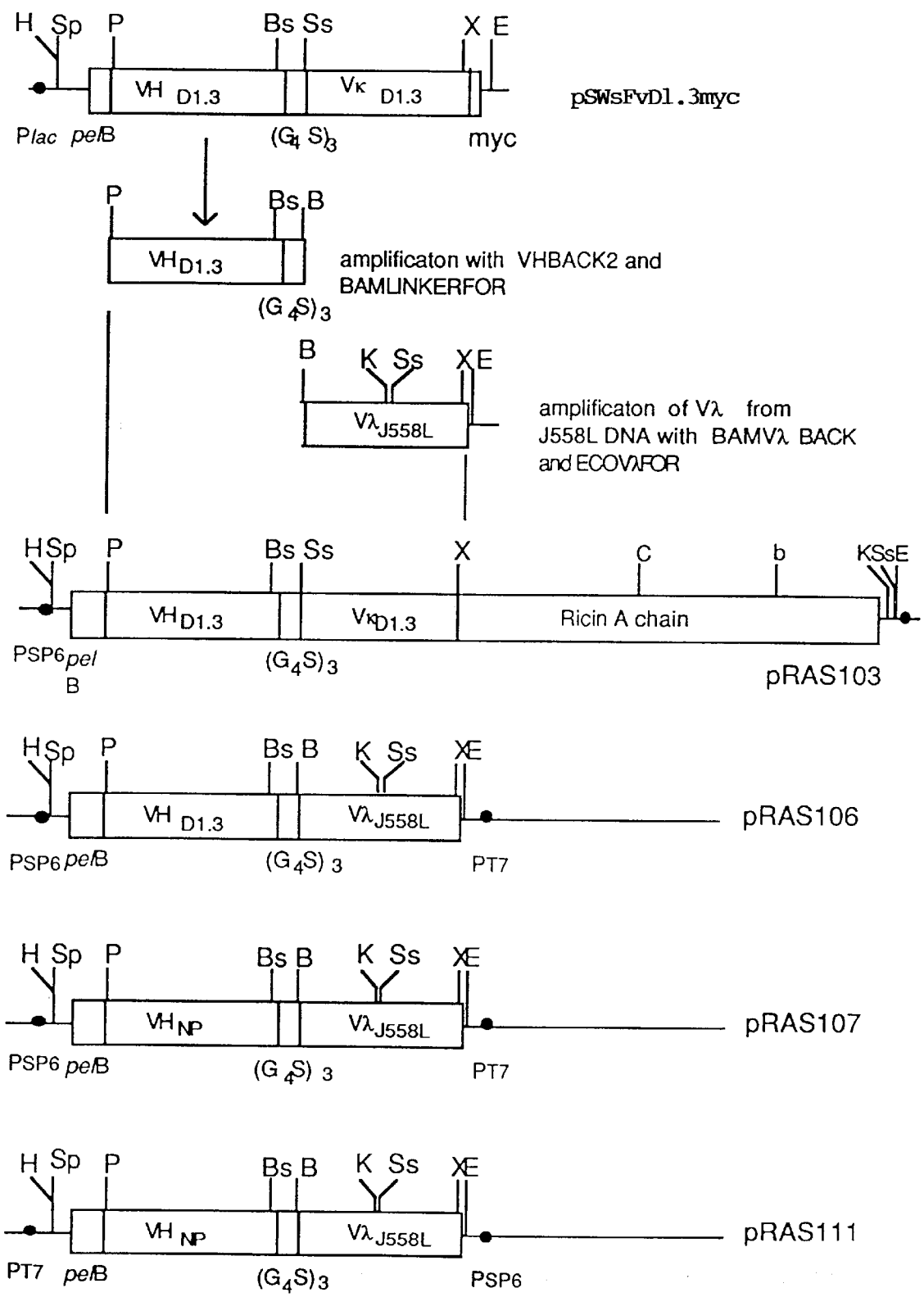
FIG. 2 shows the construction of plasmids expressing ScFv$_{NP}$.

Plasmids are shown in FIG. 2. Filled circles represent promoters: $P_{lac}$, lac promoter of pUC plasmids; $P_{SP6}$, SP6 promoter; $P_{T7}$, T7 promoter. Open boxes represent fused gene portions: pelB, the signal sequence derived from the pectate lyase B gene of *Erwinia caratovora*; $(G_4S)_3$, flexible oligopeptide linker comprising three tandem repeats of N-GlyGlyGlyGlySer-C (SEQ ID No 16); myc, a small immunogenic tag derived from c-myc. Restriction enzyme sites: B, BamHI; Bs, BstEII; b, BglII; C, ClaI; E, EcoRI; H, HindIII; K, KpnI; P, PstI; Sp, SphI; Ss, SstI; X, XhoI.

Plasmid pSWsFvD1.3myc (McCafferty et al (1990) *Nature* 348, 552–554) encodes a single-chain Fv reactive against hen egg lysozyme, and which comprises $VH_{D1.3}$ and $V\kappa_{D1.3}$ domains linked by a flexible oligopeptide, $(G_4S)_3$, under the transcriptional control of the lac promoter of *E. coli*. The region encoding $V\kappa_{D1.3}$ was replaced by one encoding Vλ in the following manner. The segment encoding $VH_{D1.3}(G_4S)_3$ was subjected to polymerase chain reaction (PCR) mediated amplification using oligonucleotide primers VHBACK2 (SEQ ID No 17) and BAMLINKER-FOR (SEQ ID No 18) (FIG. 3). Primer BAMLINKERFOR directs the incorporation of a BamHI site that also encodes the two carboxy-terminal amino acids of the flexible oligopeptide linking the two V domains.

A Vλ gene segment was amplified from chromosomal DNA of plasmacytoma J558L using primer pair BAMVλBACK (SEQ ID No 19) and ECOVλFOR (SEQ ID No 20). The former directs the incorporation of a BamHI site at the 5' end of the gene; the latter two stop codons and XhoI and EcoRI sites at the 3' end of the gene.

The two amplified products were used to replace the PstI-EcoRI fragment of plasmid pRAS103 to generate plasmid pRAS106 which encodes a ScFv protein comprising $VH_{D1.3}(G_4S)_3V\lambda_{J558L}$ under the transcriptional control of the SP6 promoter.

The PstI-BstEII fragment of pRAS106 was replaced with a PstI-BstEII fragment encoding $VH_{NP}$ amplified from plasmid pRAS49 (Spooner and Lord (1991) loc. cit.) using primers VHBACK3 (SEQ ID No 21) and VH1FOR-2 (SEQ ID No 22) to generate plasmid pRAS107. This bears a $VH_{NP}(G_4S)_3V\lambda_{J558L}$ ScFv under the transcriptional control of the SP6 promoter, and is intended purely for expression in in vitro systems.

Plasmid pRAS111 bears the ScFv of pRAS107, but under T7 promoter control, and is suitable for expression in both in vitro systems and bacterial systems.

The nucleotide sequence (and deduced amino-acid sequence) between the HindIII and EcoRI sites of plasmids pRAS107 and pRAS111 are given in FIG. 4.

TABLE 3

Plasmids used

| Plasmid | Relevant characteristics | Source or reference |
|---|---|---|
| pSWsFvD1.3myc | Anti-lysozyme ScFv, $VH_{D1.3}(G_4S)_3V\kappa_{D1.3}$ | McCafferty et al (1990) loc. cit. |
| pRAS103 | Anti-lysozyme ScFv-ricin A chain fusion, lac promoter | Spooner et al (1992) pp 7–15 in Monoclonal Antibodies 2; Applications in Clinical Oncology (Epenetos, A.A., Ed), Chapman & Hall |
| pRAS106 | $VH_{D1.3}(G_4S)_3V\lambda_{J558L}$, SP6 promoter | This application |
| pRAS49 | Anti-NP antibody H chain-ricin A chain fusion, IgH promoter | Spooner and Lord (1991) loc. cit. |
| pRAS107 | $VH_{NP}(G_4S)_3V\lambda_{J558L}$, SP6 promoter | This application |
| pRAS111 | $VH_{NP}(G_4S)_3V\lambda_{J558L}$, T7 promoter | This application |

Growth of Plasmacytoma J558L and DNA Preparation

Mouse plasmacytoma J558L cells were grown in Dulbecco's modified Eagle's medium supplemented with 10% fetal calf serum. Cells were washed twice in standard phosphate-buffered saline pH 7.4 (PBS) and high molecular weight DNA was prepared by addition, with gentle vortexing, of $10^6$ cells suspended in 100 μl PBS to 2.5 ml 10 mM Tris-HCl 1 mM EDTA pH 8.0 containing 0.02% (w/v) SDS. After adding Proteinase K to 1 mg.ml$^{-1}$, incubation (3h, 50° C.) and two phenol/chloroform extractions, DNA was precipitated with ethanol, and dissolved overnight at 4° C. in 1 ml 10 mM Tris-HCl 1 mM EDTA pH 8.

Polymerase Chain Reaction

Plasmid or chromosomal DNA (100 ng) was subjected to 24 rounds of PCR-mediated amplification (94° C., 1 min; 65° C., 1.5 min; and 72° C., 2 min) in 50 μl reaction volumes containing 25 pmol of each appropriate oligonucleotide primer, 250 μM of each dNTP, 67 mM Tris-HCl (pH 8.8), 17 mM $(NH_4)_2SO_4$, 1.5–6 mM $MgCl_2$, 200 mg.ml$^{-1}$ gelatin and 5 units of Taq polymerase (Cetus) overlaid with 25 μl paraffin oil. Amplified DNA was extracted once with phenol/chloroform and precipitated with ethanol before use.

Bacterial Expression of pRAS111 Protein

*E. coli* K12 JM109(DE3), a JM109 derivative with a chromosomal insertion of T7 polymerase under lac transcriptional control, was transformed with plasmid pRAS111. Cells were grown to a density of $10^7$ ml$^{-1}$ and expression of pRAS111 protein was induced by induction of T7 polmerase with 100 nM IPTG. A 31 kDa protein accumulates in the cells in sufficient quantity for provisional identification by Coomassie staining of cell extracts. The identity is confirmed by Western Blotting, probing with biotinylated goat anti-mouse lambda (Gαmλ) antiserum.

In addition, *E. coli* K12 BL21 (DE3), a derivative of BL21 with a single chromosomal copy of T7 RNA polymerase under lacUV5 promoter control (Studier and Moffatt (1986) *J. Mol. Biol.* 189, 113–130) was transformed with plasmid pRAS111. Cultures (400 ml) were grown at 37° C. or at room temperature in minimal salts medium supplemented with 100 μg.ml$^{-1}$ ampicillin and 1% glucose or in L-broth supplemented with 100 μg.ml$^{-1}$ ampicillin, to a density of $10^7$ cells.ml$^{-1}$. Expression of pRAS111 ScFv protein was achieved by induction of T7 polymerase with 100 nM IPTG. After induction, cells were grown for 24 h to permit accumulation of pRAS111 ScFv protein in the growth medium.

Biological Activity and Affinity Purification of pRAS111 Protein

Filtered bacterial supernatants were applied to wells of a 96-well plate previously coated with 10 mg.ml$^{-1}$NIP$_{15}$-BSA or 300 mg.ml$^{-1}$ hen egg lysozyme, and bound protein was detected by serial incubation with biotinylated Gαmλ antiserum and HRPO-streptavidin conjugate. Colour changes were generated by incubation with ABTS and were monitored at 405 nm.

Figure 5:
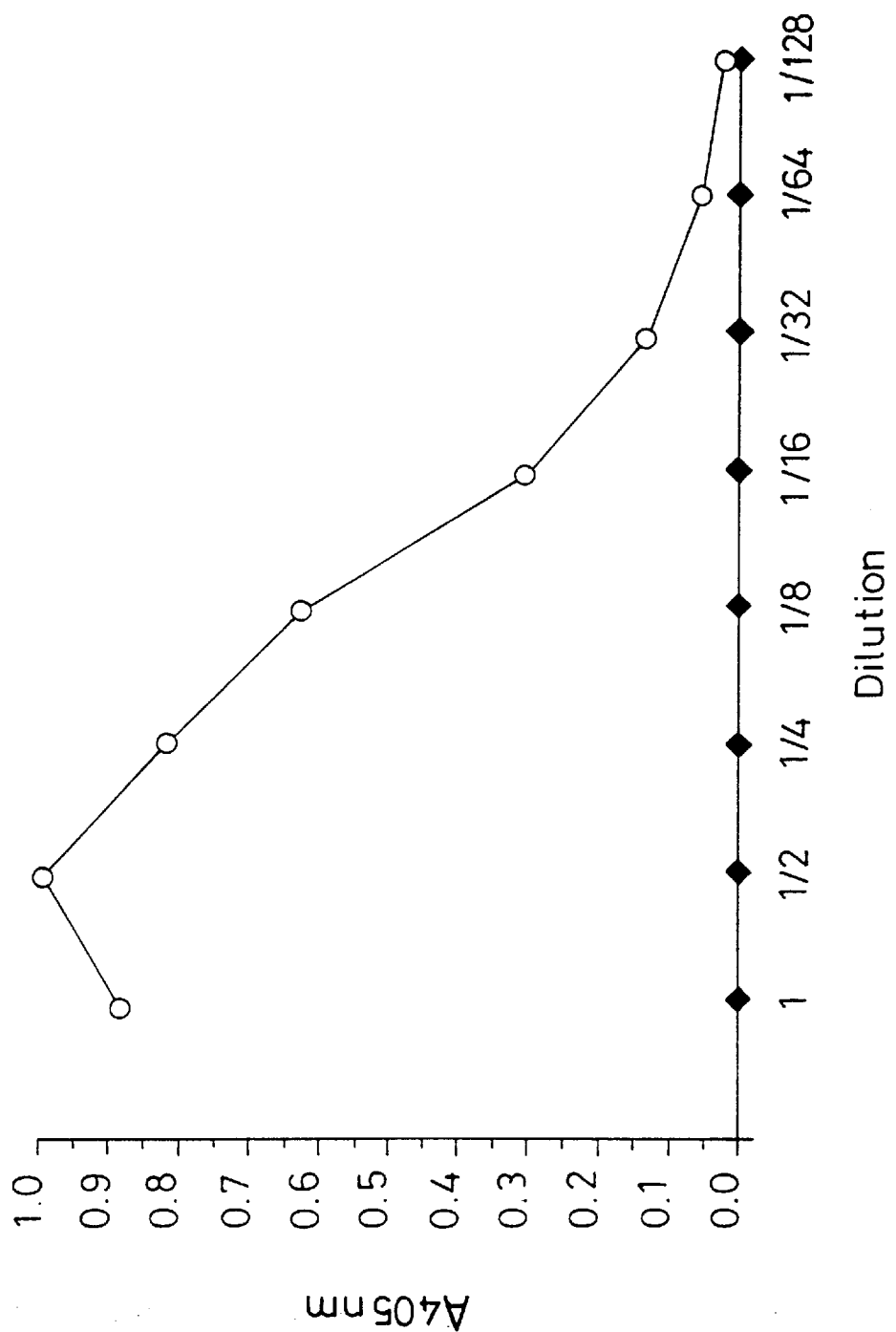
FIG. 5 shows the binding of a soluble protein expressed from pRAS111 to NIP$_{15}$-BSA. The meaning of the symbols in FIGS. 5, 6 and 12 through 14 are depicted on FIG. 6.
Figure 6:
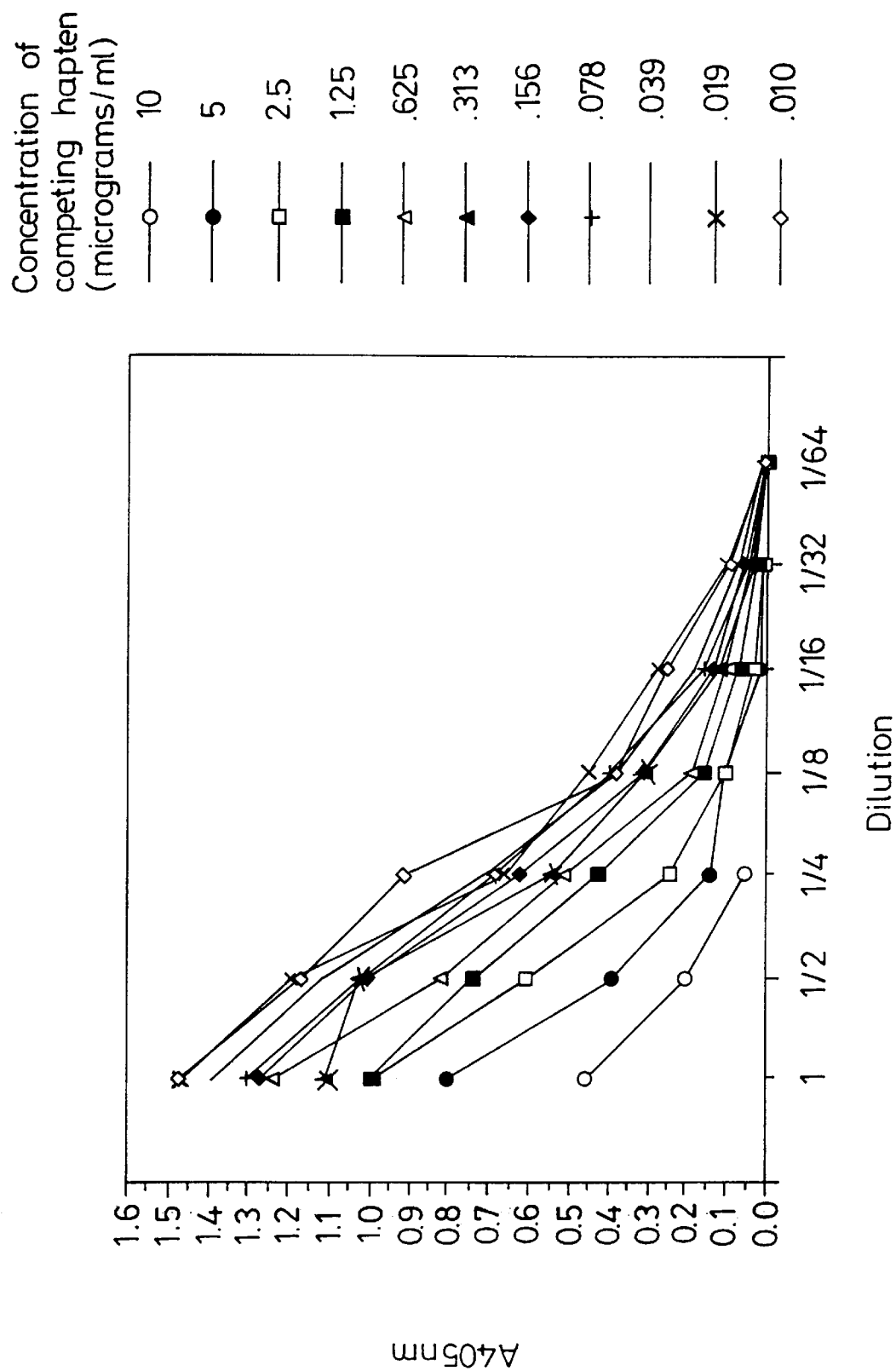
FIG. 6 shows that a soluble protein expressed from pRAS111 and which binds NIP$_{15}$-BSA can be competed by NIP$_{15}$-BSA.

A soluble protein present in the growth medium of JM109 (DE3)/pRAS111 cultures, but not in cultures of JM109 (DE3), binds NIP$_{15}$-BSA, but not lysozyme (FIG. 5). Filtered bacterial growth medium recovered after induction of pRAS111 protein was applied to wells of an ELISA plate coated with 10 μg.ml$^{-1}$ NIP$_{15}$-BSA (◉) or 300 μg.ml$^{-1}$ hen egg lysozyme (♦). Bound protein was detected by serial incubation with biotinylated Gαmλ (Goat anti-mouse lambda light chain) antisera and horseradish peroxidase conjugated streptavidin diluted in blocking buffer, and colour changes generated by addition of ABTS were monitored at 405 nm. A soluble protein present in the growth medium of JM109(DE3)/pRAS111 cultures, but not in cultures of JM109(DE3), binds NIP$_{15}$-BSA, can be competed with NIP$_{15}$-BSA (FIG. 6). ScFv protein was allowed to bind ELISA wells coated with 10 μg.ml$^{-1}$ NIP$_{15}$-BSA in the absence of competing hapten, or in the presence of 0.010 μg.ml$^{-1}$ (◇), 0.019 μg.ml$^{-1}$ (×), 0.039 μg.ml$^{-1}$ (−), 0.078 μg.ml$^{-1}$ (+), 0.156 μg.ml$^{-1}$ (♦), 0.313 μg.ml$^{-1}$ (⊀), 0.625 μg.ml$^{-1}$ (△), 1.25 μg.ml$^{-1}$ (■), 2.5 μg.ml$^{-1}$ (□), 5 μg.ml$^{-1}$ (●) or 10 μg.ml$^{-1}$ (○) competing hapten. Bound protein was detected by serial incubation with biotinylated Gαmλ antisera and horseradish peroxidase conjugated streptavidin, and colour changes generated by addition of ABTS were monitored at 405 nm. The ScFv encoded by pRAS111 was found to have a binding affinity for NP of $K_d = 4 \times 10^{-9}$M. Since bivalency of an antibody commonly provides an extra three orders of magnitude of binding ability, then an avidity of at least $10^{-12}$M would be predicted for bivalent molecules derived from ScFvNP.

As an alternative, growth medium, filtered through 0.2 μm nitrocellulose filters to remove cells and particulates, was adjusted to 80% saturation with solid ammonium sulphate at 4° C. After incubation (4° C., 1 h) treated medium was centrifuged (10,000×g, 30 min) to pellet insoluble proteins. Pellets were taken up in 20 ml PBS and were dialysed exhaustively against PBS at 4° C. Insoluble material after dialysis was removed by brief centrifugation and the remainder was adjusted to 40 ml final volume with PBS, to 0.02% with sodium azide and was applied slowly (2 ml h$^{-1}$) to a 2 ml NP-Sepharose column at room temperature. After washing with 50 column volumes of PBS containing 0.02% sodium azide (PBS/azide), bound proteins were eluted with 50 mM glycine-HCl pH 2.2 and fractions (2 ml) were immediately adjusted by addition of 200 μl 2M unbuffered Tris base. Fractions containing ScFv protein were pooled, dialysed against PBS and concentrated using Macrosep (Amicon) concentrators with a 10 kDa cut-off. Yields were estimated by Bio-Rad protein assay, using rabbit IgG as a reference, and by absorbance at 280 nm assuming $A_{280}=1$ for 1.4 mg.ml$^{-1}$ solution.

Figure 19:
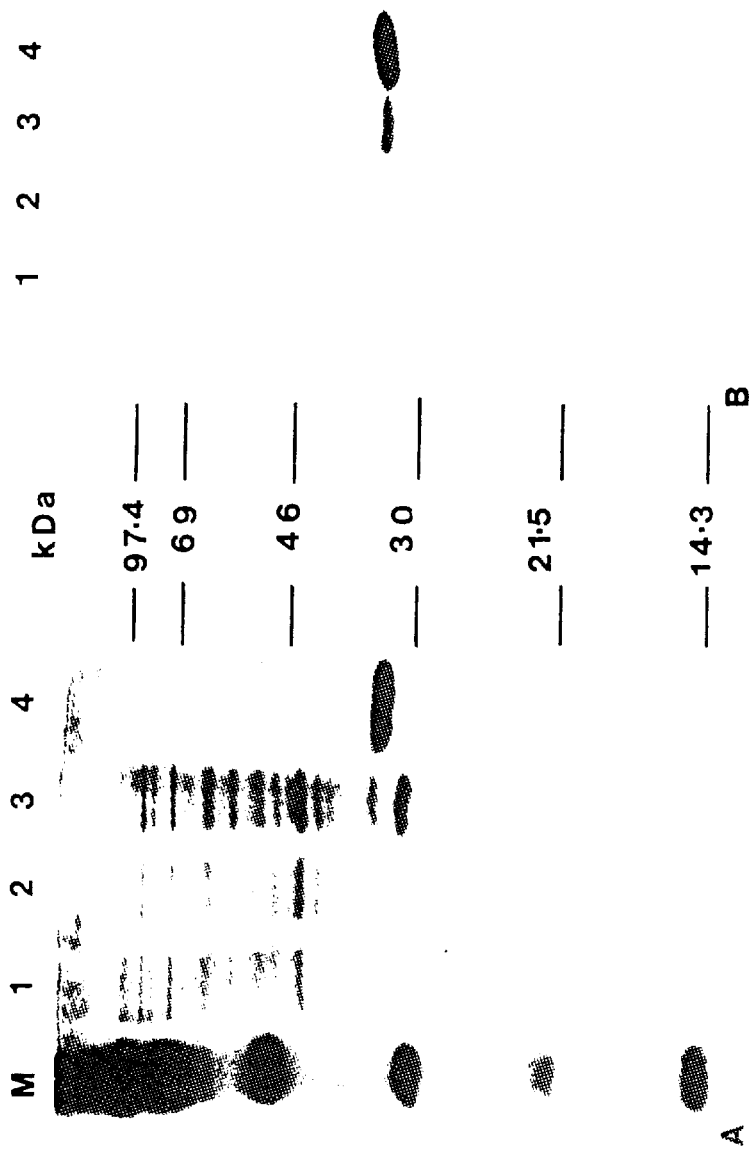
FIG. 19 shows the purification of pRAS111 ScFv$_{NP}$ protein.
Figure 20A:
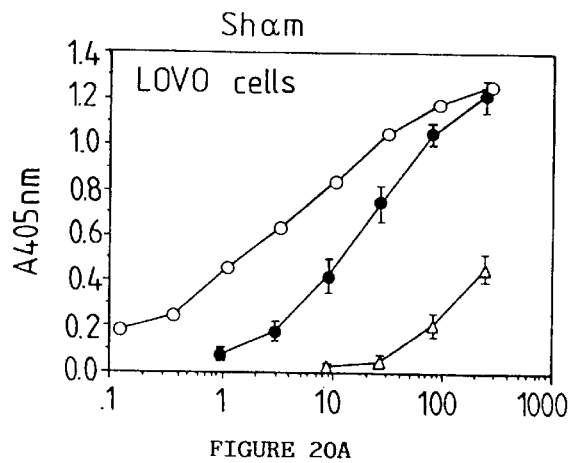
FIG. 20A, FIG. 20B, FIG. 20C, FIG. 20D, FIG. 20E and FIG. 20F show indirect targeting of pRAS111 ScFv$_{NP}$.
Figure 20B:
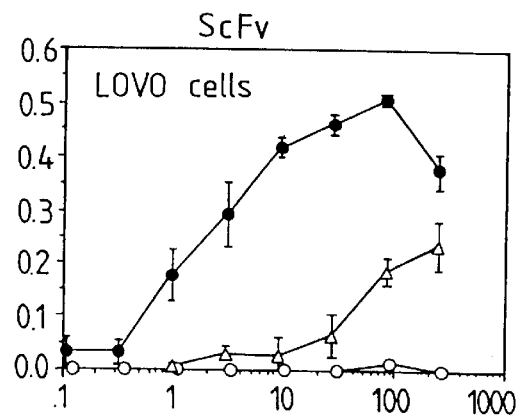
Figure 20C:
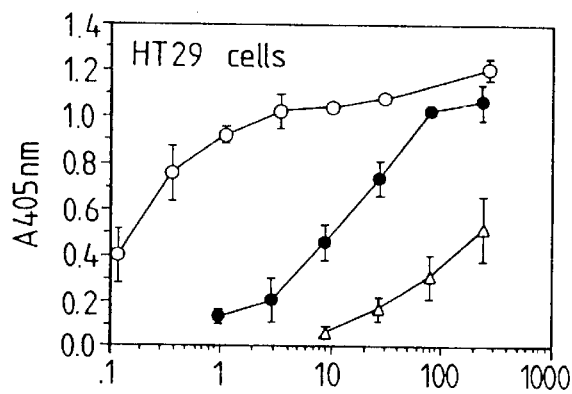
Figure 20D:
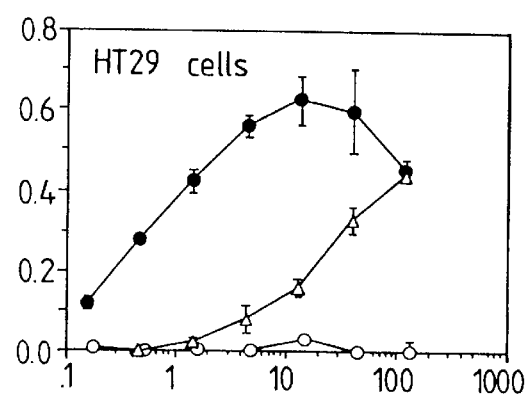
Figure 20E:
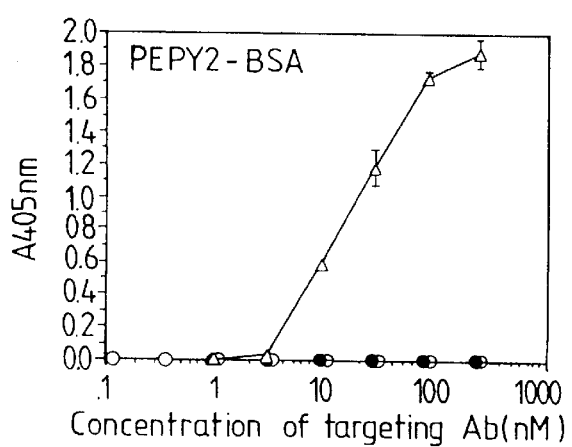
Figure 20F:
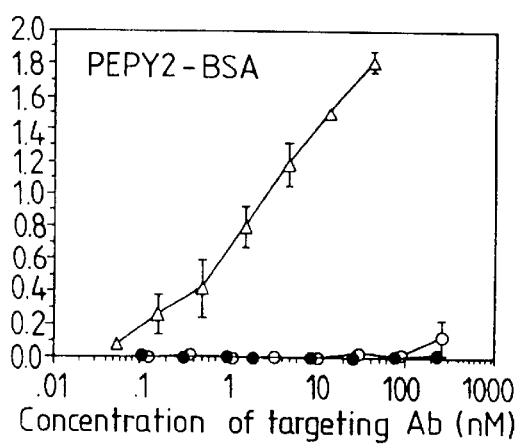

Soluble NIP-binding activity was detected by ELISA analysis of bacterial growth medium after induction, and could be concentrated by ammonium sulphate precipitation and purified by affinity chromatography on NP-Sepharose (FIG. 19) so no attempt was made to recover pRAS111 ScFv protein present in cell pellets. Yields of pRAS111 ScFv from growth medium were not greatly different when induced at room temperature or 37° C. Induction of expression was efficient in minimal salts medium and not discernible in rich broth; however, little difference was noted in the final yields. The most important factor found here was the bacterial strain, with yields of ~1.3 mg l$^{-1}$ pRAS111 ScFv protein recovered from cultures of BL21(DE3)/pRAS111, approximately ten-fold greater than those obtained from cultures of JM109(DE3)/pRAS111.

Specificity of pRAS111 Protein

The screening agent used here, biotinylated Gαmλ antiserum, also detects the λ1 light chain of anti-NP/NIP antibodies. It is therefore not possible to demonstrate specificity of pRAS111 ScFv protein for NP or NIP by competition with anti-NP/NIP antibodies, but only by its ability to recognize NP/NIP. A soluble protein present in growth medium of JM109 (DE3)/pRAS111 cultures, but not in untransformed cultures of JM109 (DE3), binds NIP$_{16}$-BSA, but not lysozyme, and can be competed with NIP$_{16}$-BSA (FIG. 5). This activity can be retained on NP-Sepharose columns, from where it can be eluted. In addition, targeting studies demonstrate no cross-reaction with BSA, PEPY2-BSA, antibody or mammalian cells.

Affinity Determinations

Results of affinity determinations using ELISA-based techniques are given in Table 4. Affinity of pRAS111 ScFv for NIP was estimated firstly by adapting the method of Mariani et al (1987) Molec. Immunol. 24, 297–303), determining the concentration of total added antibody giving half-maximal binding ($C_{t50}$) assuming $C_{t50}=1/K_{app}$, where $K_{app}$ is the apparent affinity constant. This approximation only holds true if the number of available binding sites per well is sufficiently low that their contribution is insignificant. Determinations of $K_{app}$ should approach $K_{actual}$ as the amount of antigen per well is reduced. Table 4 shows that a point is reached where similar values of $K_{app}$ are derived ($K = 2-3 \times 10^8$ M$^{-1}$), representing the closest approximation that can be made using this method.

To confirm the accuracy of this approach, similar estimations of K were made using the method of Hogg et al (1987) Molec. Immunol. 24, 797–801) in the absence of competing antigen, by calculating the slope of the linear portion of a plot of $A_{450}/[\text{ScFv}_{NP}]$ v $A_{450}$, where $A_{450}/[\text{ScFv}_{NP}]=fKn-fK(A_{450})$, $A_{450}$ is the absorbance at 450 nm, [ScFv$_{NP}$] is the concentration of added ScFv$_{NP}$, n is the concentration of available binding sites and f is the valency of the ScFv$_{NP}$ for NIP. A value of 1 was assigned to f.

TABLE 4

| Affinity determinations of pRAS111 ScFv$_{NP}$ protein | | |
|---|---|---|
| | | K (M$^{-1}$) |
| Antigen coat | concn (mg ml$^{-1}$) of coating buffer | Mariani et al (1987), Hogg et al (1987) |
| NIP$_{16}$BSA | 5 | 2.5 (± 0.1) × 10$^9$   1.6 (± 0.1) × 10$^9$ |
| NIP$_{16}$BSA | 1 | 8.2 (± 1.5) × 10$^8$   8.1 (± 0.7) × 10$^8$ |
| NIP$_4$BSA | 10 | 2.9 (± 0.3) × 10$^8$   1.2 (± 0.2) × 10$^8$ |
| NIP$_4$BSA | 5 | 2.5 (± 0.5) × 10$^8$   1.8 (± 0.1) × 10$^8$ |

Preparation of NP-Sepharose

Sepharose support (20 ml) with an amine function (Affigel 102, Biorad) was washed and suspended by addition of 20 ml 40 mM triethylamine. To this was added 430 mg NP-cap-OSu (Cambridge Research Biochemicals) dissolved in 1 ml dimethylformamide (DMF). After mixing by gentle inversion (2h, room temperature) and extensive washing in water and then PBS, NP-Sepharose was equilibrated in PBS/azide and stored in the dark at 4° C.

Western Blots to Identify pRAS111 Protein

Western blots were performed as previously described (Spooner and Lord (1991) pp 65–77 in *Monoclonal Antibodies; Applications in Clinical Oncology* (Epenetos, A. A., Ed) Chapman and Hall) and pRAS111 ScFv protein was identified by serial incubations in PBS/5% milk powder/ 0.1% Tween 20 (blocking solution), biotinylated Gamλ antisera and streptavidin-HRPO diluted in blocking solution to concentrations recommended by the suppliers. After each incubation, blots were washed 5 times in PBS/0.1% Tween 20. Proteins bound by biotinylated Gamλ antisera and steptavidin-HRPO were revealed by incubation with DAB.

EXAMPLE 2

Derivatisation of Proteins with Hapten

NIP-cap-OSu (Cambridge Research Biochemicals) was dissolved in dimethylformamide to 20 mg.ml$^{-1}$ and added to proteins as below.

NIP-BSA: for low coupling ratio, 80 μl 20 mg.ml$^{-1}$ NIP-cap-OSu/DMF was added to 1 ml 200 mg.ml$^{-1}$ BSA in 10 mM triethylamine. For high coupling ratio, 800 μl 20 mg.ml$^{-1}$ NIP-cap-OSu/DMF was added to 1 ml 200 mg.ml$^{-1}$ BSA in 100 mM triethylamine.

NIP-antibody: 200 μl 20 mg.ml$^{-1}$ NIP-cap-OSu/DMF was added to 2 ml 2.8 mg.ml$^{-1}$ antibody (AUA1 or HMFG1, Unipath) in PBS/40 mM triethylamine.

After mixing by inversion (2 h, room temperature) and extensive dialysis against PBS, insoluble material was removed by centrifugation. Soluble NIP-BSA was adjusted to 0.02% with sodium azide. Soluble NIP-antibody was sterilised by filtration (0.2 μm filter). Haptenated proteins were stored at 4° C. in the dark. Protein concentration was estimated by Bio-Rad protein assay.

The number of haptens conjugated to each protein molecule was estimated by absorbance at 430 nm according to Brownstone et al (1966) *Immunology* 10, 465–479: low coupling ratio NIP-BSA, 3.7 (NIP$_4$-BSA); high coupling ratio NIP-BSA, 16.4 (NIP$_{16}$-BSA); NIP-AUA1, 38.3 (NIP$_{38}$-AUA1) and NIP-HMFG1, 35.4 (NIP$_{35}$-HMFG1).

EXAMPLE 3

Indirect Targeting Using pRAS111 ScFv Protein

The measured affinity of ScFv$_{NP}$ or pRAS111 protein is sufficiently high to contemplate cell targeting by a two-step approach. Cells (LOVO and HT29) and peptide (PEPY-BSA) were incubated with AUA1, NIP$_{38}$-AUA1, or NIP$_{35}$-HMFG1, and bound material was detected by incubation with sheep anti mouse antisera (Shαm) conjugated to HRPO or by serial incubation with biotinylated Gamλ and streptavidin-HRPO (FIG. 20). LOVO cells, which express AUA1 antigen, can be identified by serial incubation with specific antibody (AUA1) and with Shαm conjugated to HRPO. Hapten-derivatised NIP$_{38}$-AUA1 displayed a marked reduction in cell-binding ability, with loss of approximately 90% of immunoreactivity. Hapten-conjugated NIP$_{35}$-HMFG1 also bound LOVO cells, reflecting the ability of HMFG1 to bind these cells when presented at high concentration. When pRAS111 ScFv$_{NP}$ protein was used as a detection layer, hapten-derivatised NIP$_{38}$-AUA1 and NIP$_{35}$-HMFG1 were both recognised, but non-hapten-conjugated AUA1 was not. Similar results were obtained with a different cell line, HT29, that also expresses AUA1 antigen.

When the specificity of the system was altered completely, a peptide (PEPY2) derived from the protein backbone of polymorphic epithelial mucin identified with NIP$_{35}$-HMFG1 antibody was bound by pRAS111 ScFv protein whilst those incubated with AUA1 and NIP$_{38}$-AUA1 were not.

The specificity of pRAS111 ScFv$_{NP}$ protein is therefore dependent upon prior targeting with a hapten-derivatised primary targeting vehicle, and the specificity of targeting depends only upon the interaction of primary hapten-conjugated targeting vehicle and the interaction of second step ScFv with the primary targeting vehicle.

For ELISAs using fixed mammalian cells, cells were seeded into wells of 96-well microculture plates at 10$^5$ cells.ml$^{-1}$ in RPMI supplemented with 10% fetal calf serum and were grown to confluence at 37° C. in a 5% CO$_2$ atmosphere. Cells were washed twice in PBS, were incubated in 0.25% glutaraldehyde in PBS (100 μl per well, room temperature, 15 min) and after a further wash in PBS, were stored at 4° C. in PBS/azide.

Unbound sites were blocked (30 min, room temperature) using 1% milk powder reconstituted in PBS containing 0.1% Tween 20 (blocking buffer). Antibodies and hapten-conjugated antibodies were applied and were detected by serial incubation with pRAS111 ScFv protein, biotinylated Gamλ antisera and streptavidin-HRPO or by incubation with horseradish peroxidase conjugated Sheep anti mouse serum, diluted in blocking buffer to appropriate concentrations. After each incubation, plates were washed 5 times in PBS containing 0.1% Tween 20. Colour changes were generated using ABTS (monitored at 405 nm) or OPD (monitored at 450 nm).

The results of indirect targeting of pRAS111 ScFv$_{NP}$ are shown in FIG. 20.

Binding of AUA1 (open circles), NIP$_{38}$-AUA1 (closed circles) and NIP$_{35}$-HMFG1 (open triangles) to LOVO cells, HT29 cells and to a peptide derived from the mucin backbone conjugated to BSA (PEPY2-BSA). Bound primary antibody was detected using HRPO-conjugated sheep anti-mouse antisera (Shαm) or by recognition using pRAS111 ScFv$_{NP}$ (ScFv).

EXAMPLE 4

Construction of High Avidity ScFv-streptavidin Fusion

Plasmid Constructions

Figure 7:
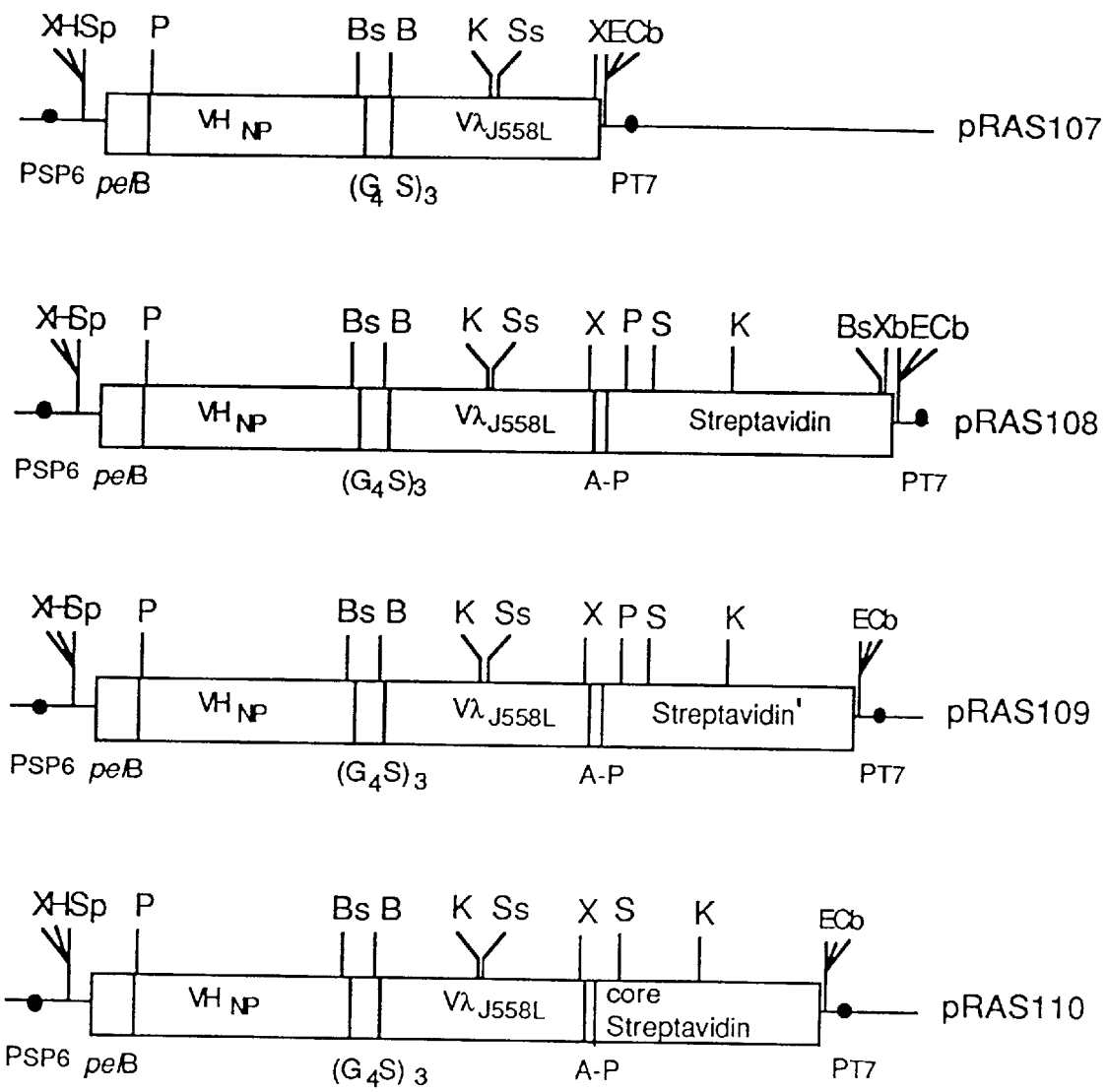
FIG. 7 shows the construction of plasmids expressing ScFv-streptavidin fusions in vitro.

Plasmids for the in vitro expression of ScFv-streptavidin fusions are shown in FIG. 7. Filled circles represent promoters: P$_{SP6}$, SP6 promoter; P$_{T7}$, T7 promoter. Open boxes represent fused gene portions: pelB, the signal sequence derived from the pectate lyase B gene of *Erwinia caratovora*; (G$_4$S)$_3$, flexible oligopeptide linker comprising three tandem repeats of N-GlyGlyGlyGlySer-C; A-P, a novel flexible oligopeptide linker.

Restriction enzyme sites: B, BamHI; Bs, BstEII; b, BglII; C, ClaI; E, EcoRI; H, HindIII; K, KpnI; P, PstI; Sp, SphI; Ss, SstI; X, XhoI; Xb, XbaI.

Figure 8:
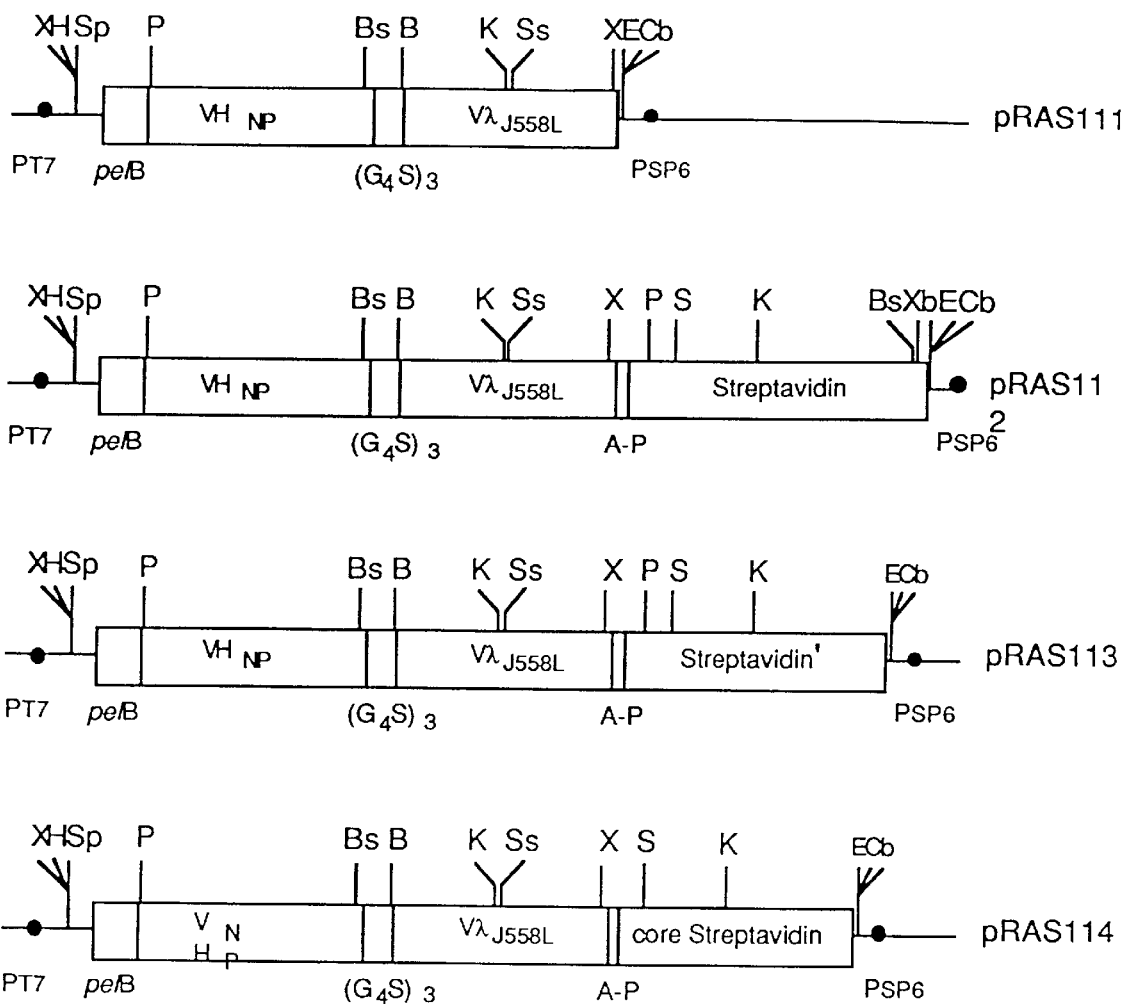
FIG. 8 shows the construction of plasmids for the expression of ScFv-streptavidin fusions in *E. coli*.

Plasmids for the expression of ScFv-streptavidin fusions in *E. coli* are shown in FIG. 8. Filled circles represent promoters: P$_{SP6}$, SP6 promoter; P$_{T7}$, T7 promoter. Open boxes represent fused gene portions: pelB, the signal sequence derived from the pectate lyase B gene of *Erwinia caratovora*; (G$_4$S)$_3$, flexible oligopeptide linker comprising three tandem repeats of N-GlyGlyGlyGlySer-C; A-P, a novel flexible oligopeptide linker Restriction enzyme sites: B, BamHI; Bs, BstEII; b, BglII; C, ClaI; E, EcoRI; H, HindIII; K, KpnI; P, PstI; Sp, SphI; Ss, SstI; X, XhoI; Xb, XbaI.

Segments of DNA encoding mature streptavidin monomers or fragments were amplified by PCR and were used to replace the XhoI-EcoRI fragment of plasmid pRAS107 to generate plasmids pRAS108, pRAS109 and pRAS110, which encode ScFv$_{NP}$-streptavidin fusions under SP6 transcriptional control.

Plasmid pRAS108 encodes a ScFv$_{NP}$ fused via a novel oligopeptide (APAAAPA (SEQ ID No 23)). Its product is expected to tetramerise via the streptavidin monomer moieties. Mature streptavidin often forms higher order complexes, probably through interaction of the amino-terminal and carboxy-terminal regions which are thought to be flexible extensions. Many commercial preparations lack these, through natural proteolysis, and form stable tetramers. In order to mimic this, two further ScFv$_{NP}$-streptavidin derivatives were made, one borne on plasmid pRAS109 and which lacks the 19 carboxy terminal amino acids of streptavidin, and the other, on plasmid pRAS110, which further lacks the 12 amino-terminal amino acids of streptavidin. Plasmid pRAS110 thus encodes a ScFv$_{NP}$ linked to "core" streptavidin monomers, typical of many commercial preparations.

Plasmids pRAS112, pRAS113 and pRAS114 are derived from plasmids pRAS108, pRAS109 and pRAS110 respectively, and code for ScFv$_{NP}$-streptavidin fusions under the transcriptional control of the T7 promoter.

The nucleotide sequence (and deduced amino-acid sequence) between the HindIII and EcoRI sites of plasmids pRAS108 and pRAS112 are given in FIG. 9, the sequences of plasmids pRAS109 and pRAS113 in FIG. 10 and those of plasmid pRAS110 and pRAS114 are displayed in FIG. 11.

Bacterial Expression of pRAS112, pRAS113 and pRAS114 Proteins

In contrast to ScFv$_{NP}$, in the conditions used, proteins encoded by plasmids pRAS112, pRAS113 and pRAS114 do not accumulate after induction in amounts sufficient for provisional identification by Coomassie staining. Western Blotting of cell extracts and culture supernatants, probing with biotinylated Gαmλ antiserum and HRPO-streptavidin conjugate or rabbit α-streptavidin (RαS) antiserum and HRPO-donkey α-rabbit (DαR) antiserum allows identification of fusion proteins of expected monomeric sizes. Very little ScFv$_{NP}$-core streptavidin accumulates after induction of expression of pRAS114 protein.

In non-reducing conditions, almost all of the ScFv-streptavidin material migrates with sizes corresponding to multimeric forms (at ~90 kDa for a dimer and 180 kDa for the tetramer). Note that in the conditions employed here, streptavidin itself exists mostly as higher order aggregates.

Antigen Binding

Filtered bacterial supernatants were applied to wells of a 96-well plate previously coated with 10 μg.ml$^{-1}$ NIP$_{15}$-BSA or 300 μg.ml$^{-1}$ hen egg lysozyme, and bound protein was detected by serial incubation with biotinylated Gαmλ antiserum and HRPO-streptavidin conjugate or RαS antiserum and HRPO-DαR antiserum. Colour changes were generated by incubation with ABTS and were monitored at 405 nm.

Figure 12:
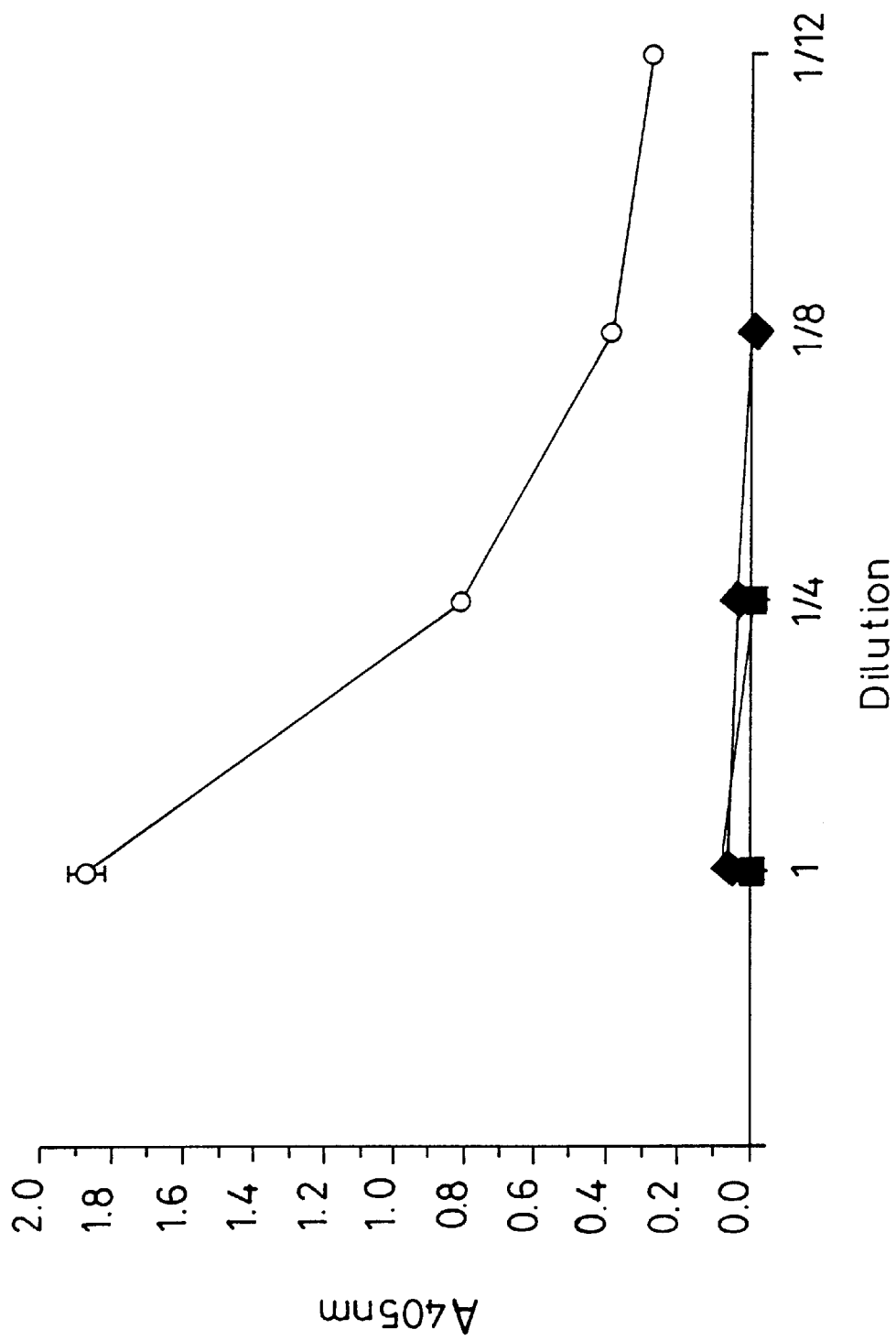
FIG. 12 shows the detection of soluble pRAS112-encoded protein (full length ScFv$_{NP}$-streptavidin monomer) in bacterial supernatants.
Figure 13:
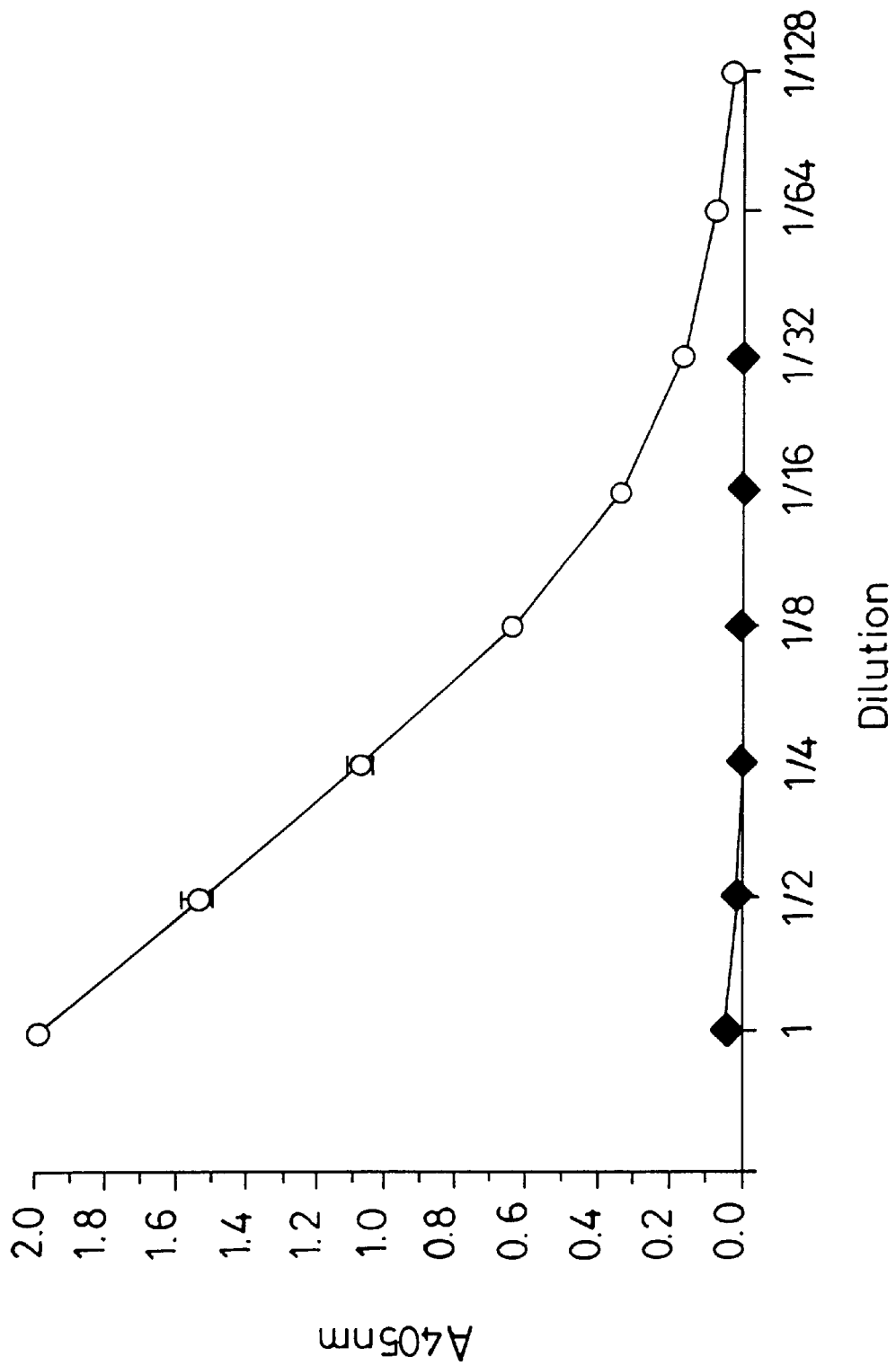
FIG. 13 shows that pRAS112-encoded protein binds to NIP$_{15}$-BSA, but not to lysozyme.

Only soluble pRAS112 protein (full length ScFv$_{NP}$-streptavidin monomer) can be detected in bacterial supernatants (FIG. 12). Filtered bacterial growth medium recovered after induction of pRAS112 (◯), pRAS113 (♦) or pRAS114 (■) protein was diluted in PBS and applied to wells of an ELISA plate coated with 10 μg.ml$^{-1}$ NIP$_{15}$-BSA. Bound protein was detected by serial incubation with Rabbit α Streptavidin antisera and horseradish peroxidase conjugated Donkey α Rabbit antisera, and colour changes generated by addition of ABTS were monitored at 405 nm. Like the parental ScFv$_{NP}$, this protein binds NIP$_{15}$-BSA, but not lysozyme (FIG. 13). Filtered bacterial growth medium recovered after induction of pRAS112 protein was applied to wells of an ELISA plate coated with 10 μg.ml$^{-1}$ NIP$_{15}$-BSA (◯) or 300 μg.ml$^{-1}$ hen egg lysozyme (♦). Bound protein was detected by serial incubation with Rabbit α Streptavidin antisera and horseradish peroxidase conjugated Donkey α Rabbit antisera, and colour changes generated by addition of ABTS were monitored at 405 nm.

Partial Purification of pRAS112 Protein

Figure 14A:
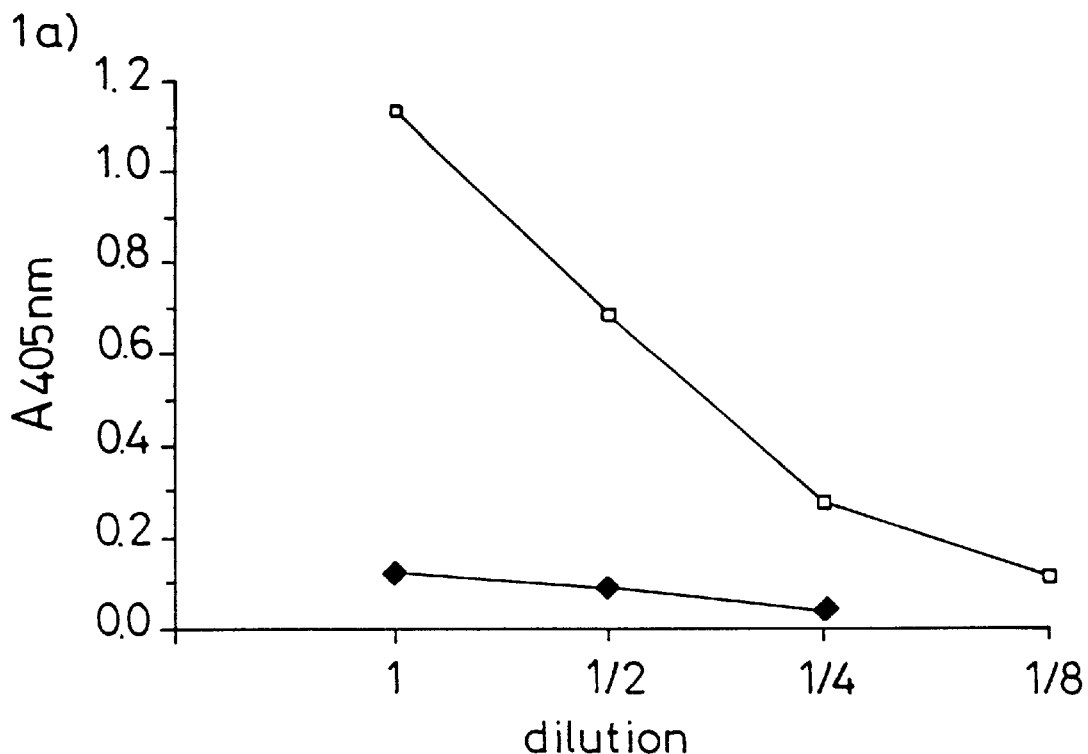
FIG. 14A and FIG. 14B show that concentrated pRAS112-encoded protein binds iminobiotin-Sepharose at pH 11 in contrast to parental ScFv$_{NP}$ protein that does not.
Figure 14B:
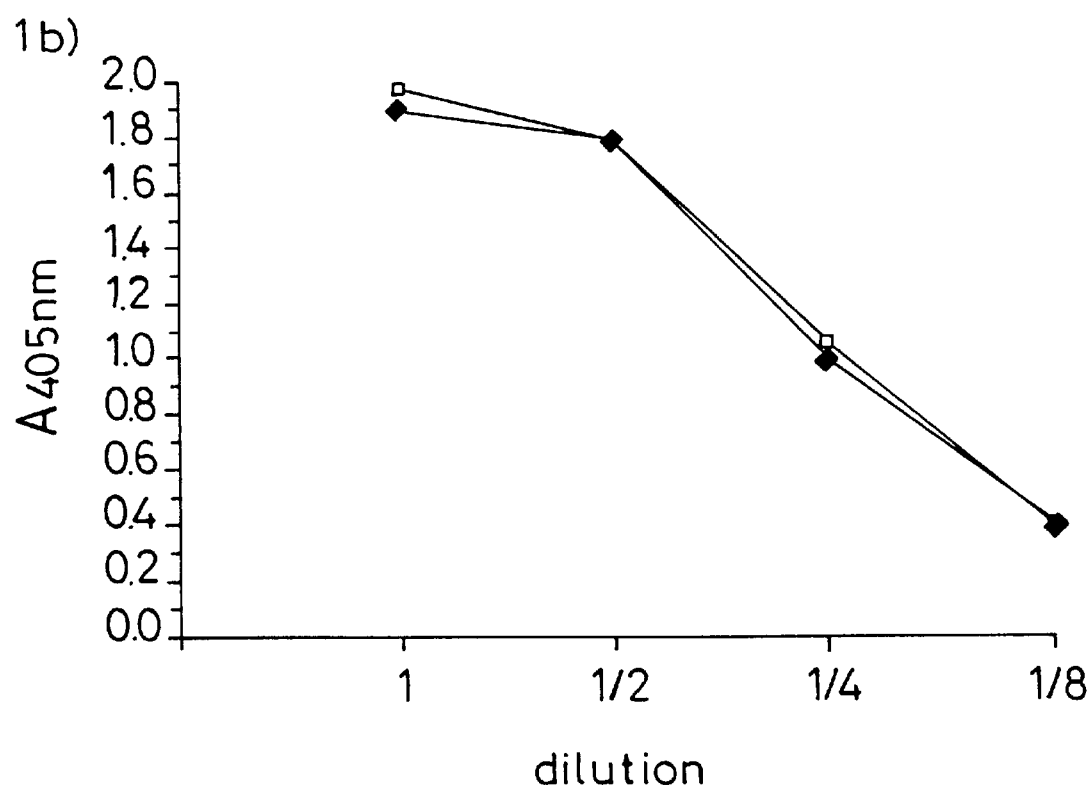

ScFv$_{NP}$-streptavidin fusion protein (pRAS112 protein) can be concentrated about 20-fold by precipitation from 50% saturated ammonium sulphate and dialysis against PBS. As expected concentrated pRAS112 protein binds iminobiotin-Sepharose at pH11, in contrast to parental ScFv$_{NP}$ protein (FIG. 14). Concentrated proteins resolubilised in PBS after precipitation from 50% (pRAS112) or 80% (pRAS111) saturated ammonium sulphate were applied at pH11 to a iminobiotin-Sepharose column (Pierce), and antigen binding ability of material applied to the column (◯) and material flowing through the column (♦) were measured by appropriate ELISA. a) pRAS112 protein, b) pRAS111 protein.

Figure 34:
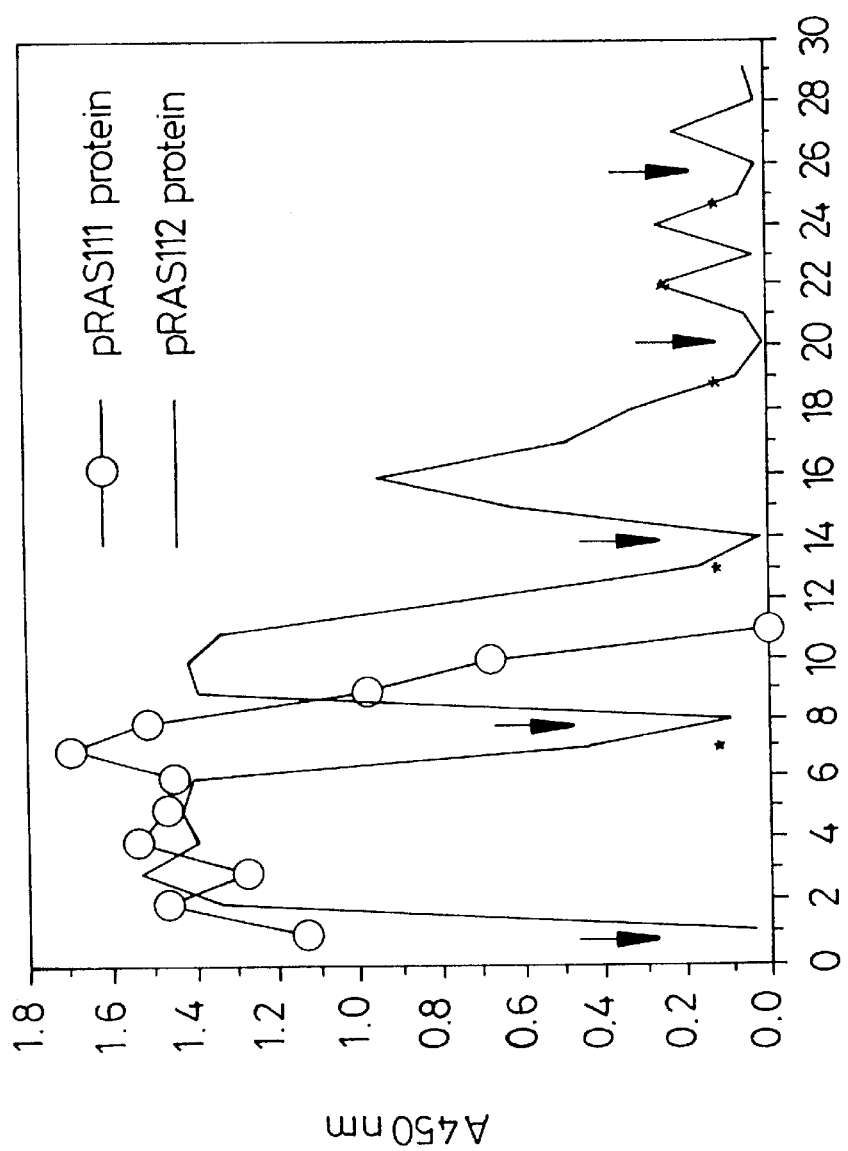
FIG. 34 shows the elution of pRAS111 and pRAS112 proteins from NP-sepharose with 50 mM glycine HCl, pH 2.2.

The avidity of streptavidin fusions can be compared with univalent ScFvs.

a) The slope of a NIP-specific ELISA performed using pRAS112 streptavidin fusion differs from that performed using pRAS111 scFv.

b) pRAS112 protein binding to NIP-BSA cannot be competed with free NP, free NIP or NIP-BSA, whereas pRAS111 scFv can.

c) pRAS112 protein cannot be eluted in a single pulse from a NP-Sepharose column. Multiple pulses of low pH interspersed with high pH washes are required to elute this protein. In contrast, pRAS111 scFv elutes with a single low pH step (FIG. 34).

This indicates that the streptavidin fusions (pRAS112) are binding multivalently.

Figure 15:
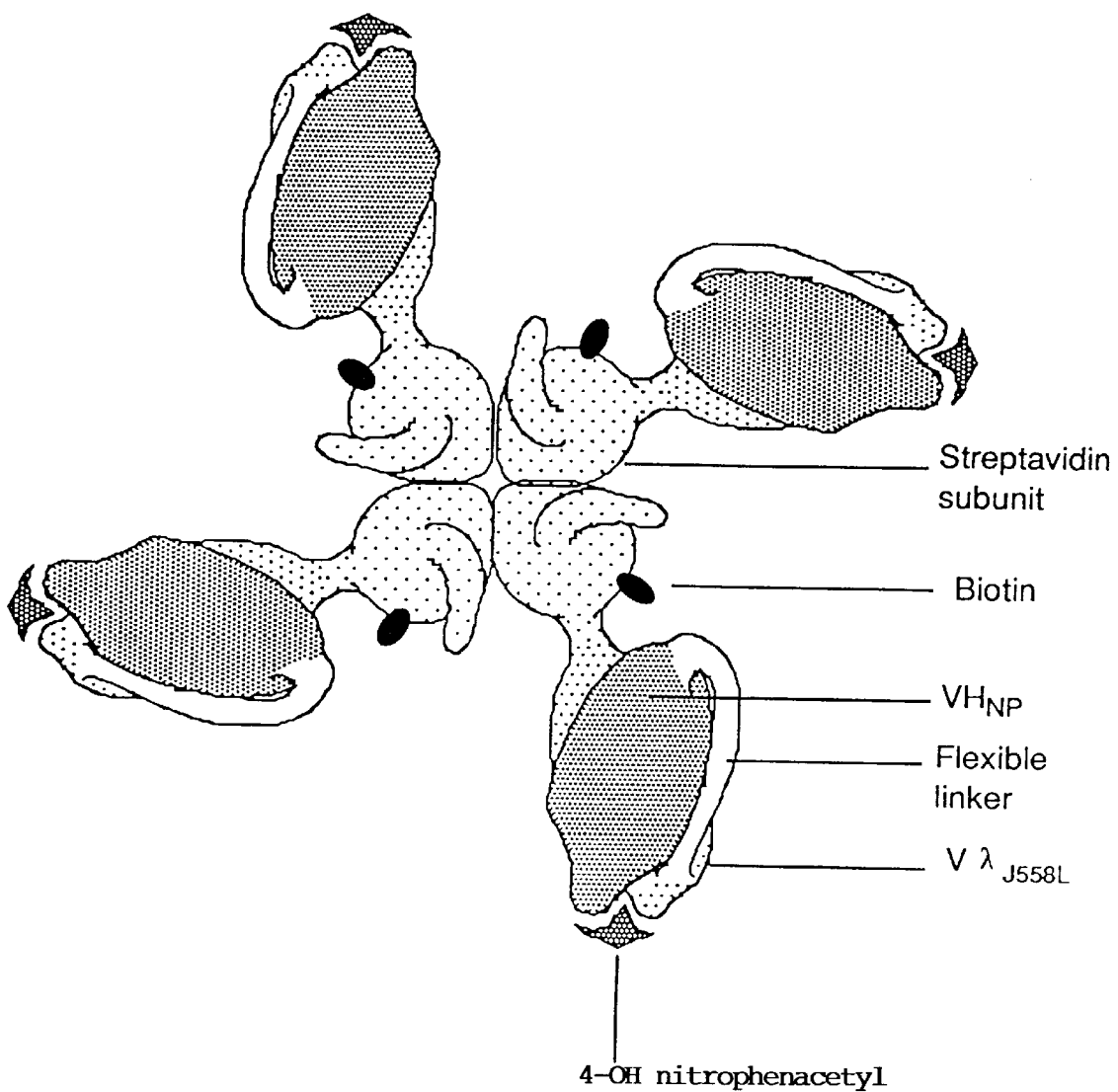
FIG. 15 shows a diagrammatic representation of pRAS112-encoded protein.

A representation of the pRAS112 protein is shown in FIG. 15.

EXAMPLE 5

Construction of ScFv-BSRNase Fusion Molecules

Plasmid Construction

Figure 16:
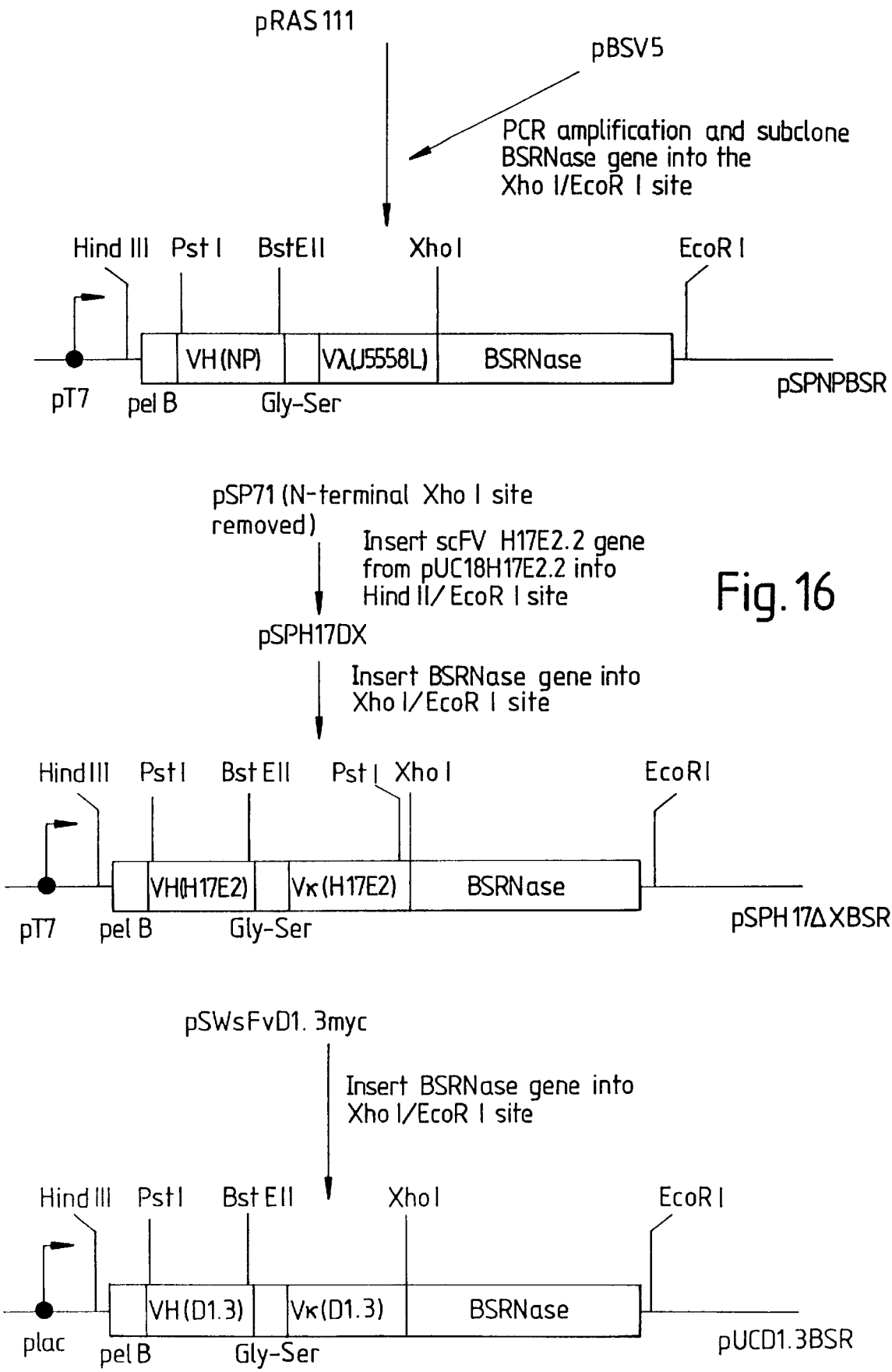
FIG. 16 shows the construction of plasmids expressing ScFv-BSRNase fusion molecules.

Plasmids for the expression of ScFv-BSRNase fusions are shown in FIG. 16. The plasmid pRAS111 is described in Example 1, and the plasmid pBSV5 is as described in Schein et al, loc. cit.

FIG. 21 shows the sequence of the ScFv-BSRNase fusion (4-OH nitrophenacetyl antibody) inserted between the HindIII and EcoRI sites of plasmid pSP7 (available from Promega) to give plasmid pSPNPBSR as shown in FIG. 16.

FIG. 22 shows the sequence of the ScFv-BSRNase fusion (anti-human placental alkaline phosphatase antibody; H17E2) inserted between the HindIII and EcoRI sites of plasmid pSP71 to give plasmid pSPH17ΔXBSR as shown in FIG. 16.

The amino acid sequences of the V$_H$ and V$_L$ chains of H17E2 are disclosed in "Monoclonal Antibodies—applications in clinical oncology", pages 37–43, 1991, A. A. Epenetos, ed., Chapman & Hall, UK.

FIG. 23 shows the sequence of the ScFv-BSRNase fusion (anti-lysozyme antibody) inserted between the HindIII and EcoRI sites of plasmid pUC18 (available from Pharmacia) to give pUCD1.3BSR as shown in FIG. 16.

Figure 17:
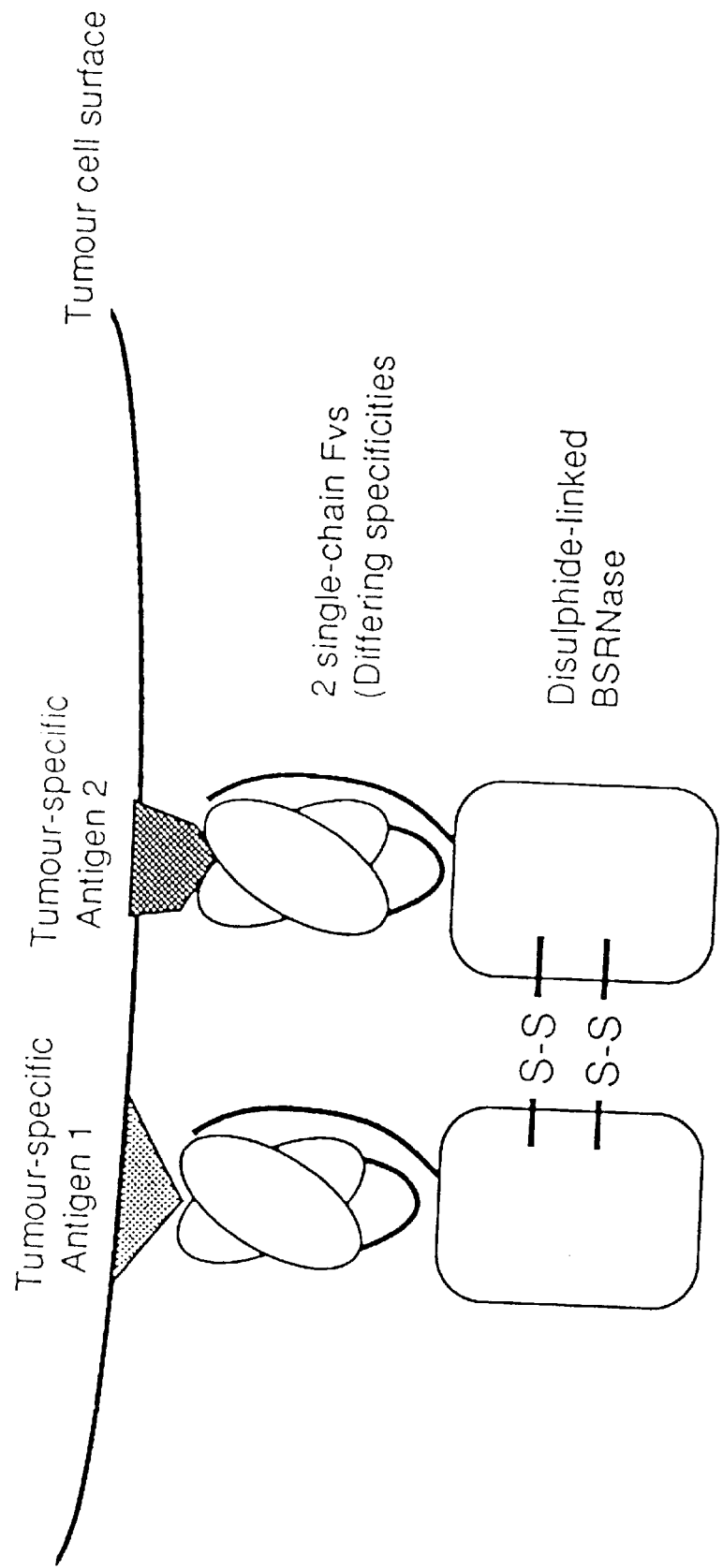
FIG. 17 shows a diagrammatic representation of a ScFv-BSRNase heterodimer.

FIG. 17 shows a diagrammatic representation of the specific case where a heterodimer has been synthesised and purified (as described supra), in this case each of the ScFvs recognizes a different antigen on the same tumour cell.

The plasmids were made using standard methods of molecular biology as disclosed by Sambrook et al (1989) in *Molecular Cloning, a laboratory manual*, 2nd Edn, Cold Spring Harbor Laboratory Press, NY, USA.

The plasmid pSPNPBSR encodes a protein which directs cytotoxin RNase to a target cell-specific molecule derivatised with NP or NIP. The plasmid pPSH17ΔXBSR encodes a protein which directs RNase to cells expressing the human placental alkaline phosphatase antigen. The ScFv encoded by this plasmid is derived from the monoclonal antibody H17E2 (see Table 1).

In addition to the fusion gene consisting of the H17E2 scFv and seminal RNase only (see above) the following fusion genes which incorporate one or more of the following are useful:

(i) A C-terminal "KDEL" sequence (endoplasmic reticulum retention signal), which may elevate cytotoxicity by increasing the retention of the protein in the cell and reducing its loss to other endosomal pathways.

(ii) A linker sequence at the N-terminus of the RNase to allow the N-terminus to be more flexible and increase the likelihood of forming dimers.

(iii) A disulphide loop containing sequence, derived from the diptheria toxin, which allows the scFv and RNase to be linked via a disulphide bond, and permits efficient release of the RNase from the scFv once the cytotoxin has been internalised.

The plasmids which contain these genes (described diagrammatically in FIG. 28 and individual nucleotide sequences encoding these proteins given in FIGS. 29 to 33) are identical to that expressing the original scFv-RNase fusion protein, i.e. only the DNA sequence of the actual cytotoxic molecule has been altered. The conditions for expression and refolding are as described in the earlier Examples.

Characterisation of the scFv-RNase Protein

RNase Activity of the Fusion Proteins.

All the fusions described, H17-BSRNase, H17-DT-BSRNase, H17-DT-BSRNaseKDEL,H17-DT-Link-BSRNase,H17-DT-Link-BSRNaseKDEL, H17-BSRNaseKDEL, H17-Link-BSRNaseKDEL, have RNA-degrading activity, as demonstrated by an RNase assay which involves incubating a sample of the refolded protein (10–50 ng of crude fusion protein) with 5 μg of RNA in a volume of 20 μl at 37° C. for 1 hr. In each case all the RNA was degraded, showing qualitative RNase activity in the fusion protein preparations.

Antigen-binding Activity of Fusion Proteins.

All the fusion proteins demonstrate binding to the antigen human placental alkaline phosphatase (hPLAP) in an ELISA system. The detecting layers for the ELISA were anti-bovine seminal RNase polyclonal antibodies (from rabbit) and anti-rabbit polyclonal antibodies (from goat).

Evidence for the Dimeric Nature of the scFv-RNase.

Gel filtration experiments show the native molecular weight of the fusion proteins. Data from binding experiments indicates that the molecule has a higher avidity than the single-chain H17E2 antibody alone: the scFv will bind to an antigen affinity column (the antigen is placental alkaline phosphatase) and is eluted with a buffer consisting of 50 mM diethylamine (DEA), pH 12. The fusion protein, due to its higher avidity cannot be eluted under these mild conditions, and more harsh conditions are needed, eg 100 mM glycine, pH 2.2. Also, when the scFv and whole IgG H17E2 and fusion proteins are bound to their antigen on an ELISA plate and washed with copious amounts of 50 mM DEA, over 90% of the scFv is washed off, whereas only 40% of the whole IgG and fusion protein is washed off. Finally, the shape of the ELISA curve for the whole IgG H17EE2 and fusion protein are similar (shallow slope), but that of the scFv is a steep slope. These experiments indicate that the scFv-RNase protein is dimeric.

Cytotoxicity of the Fusion Proteins Towards an Antigen-positive Cell-Line (HEp2).

HEp2 cells were seeded in 96-well microtitre plates and grown overnight in E4 culture media with 10 fetal calf serum (FCS) at a density of $10^5$ cells per well. The next day, 10 μl of crude refolded fusion protein in PBS was added to each well and allowed to grow for 72 hr. Cell-killing was detected using the Promega cell-titre 96 assay kit, which measures cell proliferation.

Figure 27:
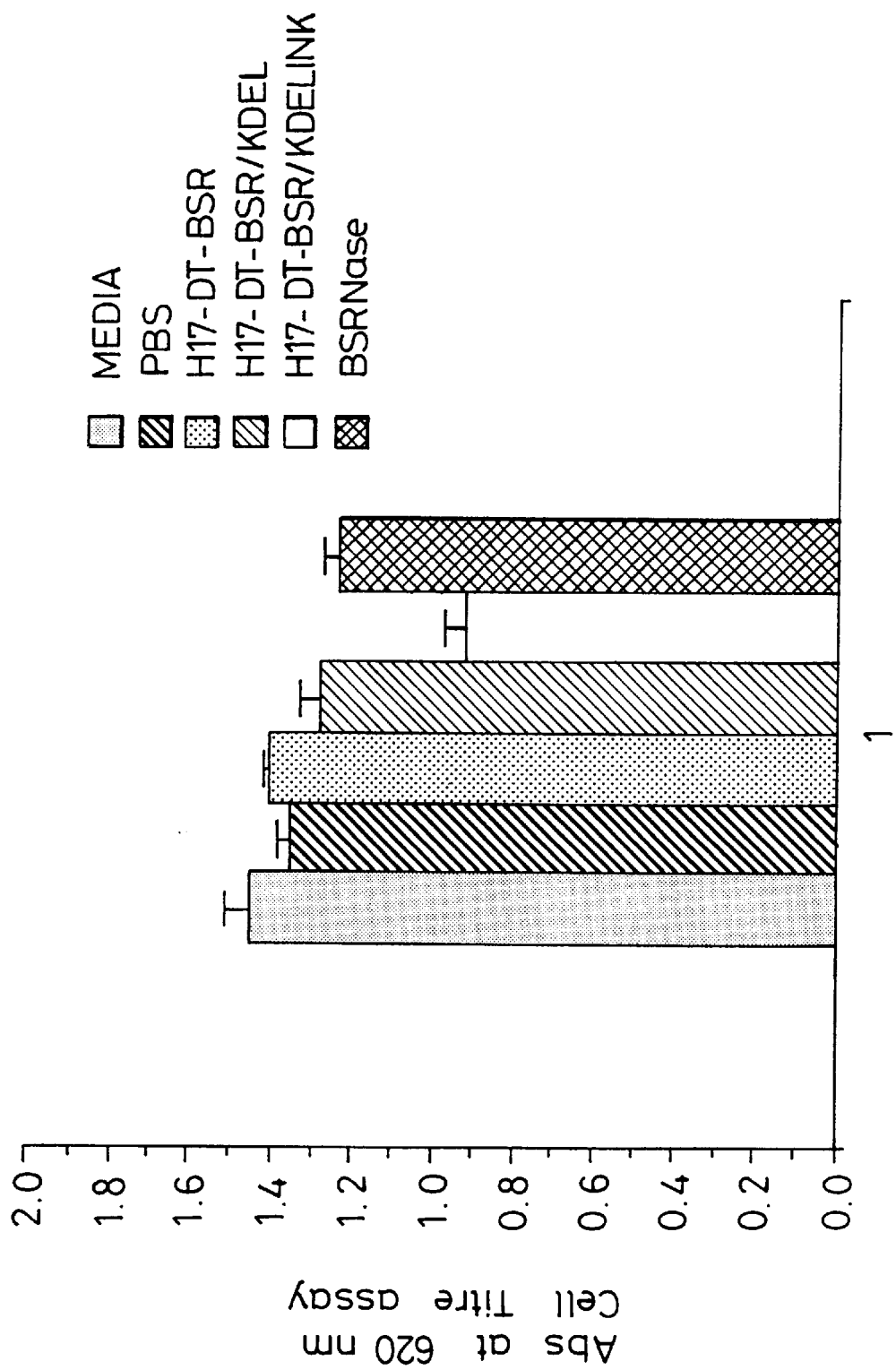
FIG. 27 shows the results of cell-killing experiments using HEp2 cells and the fusion protein H17-DT-BSR, H17-DT-BSR/KDEL and H17-DT-BSR/KDELINK.

The scFv-BSRNase fusion protein consisting of a disulphide loop, KDEL and linker showed significant cell killing activity. The estimated final concentration of the cytotoxin was between 10–100 nM (see FIG. 27 for the results of these experiments).

EXAMPLE 6

Figure 18:
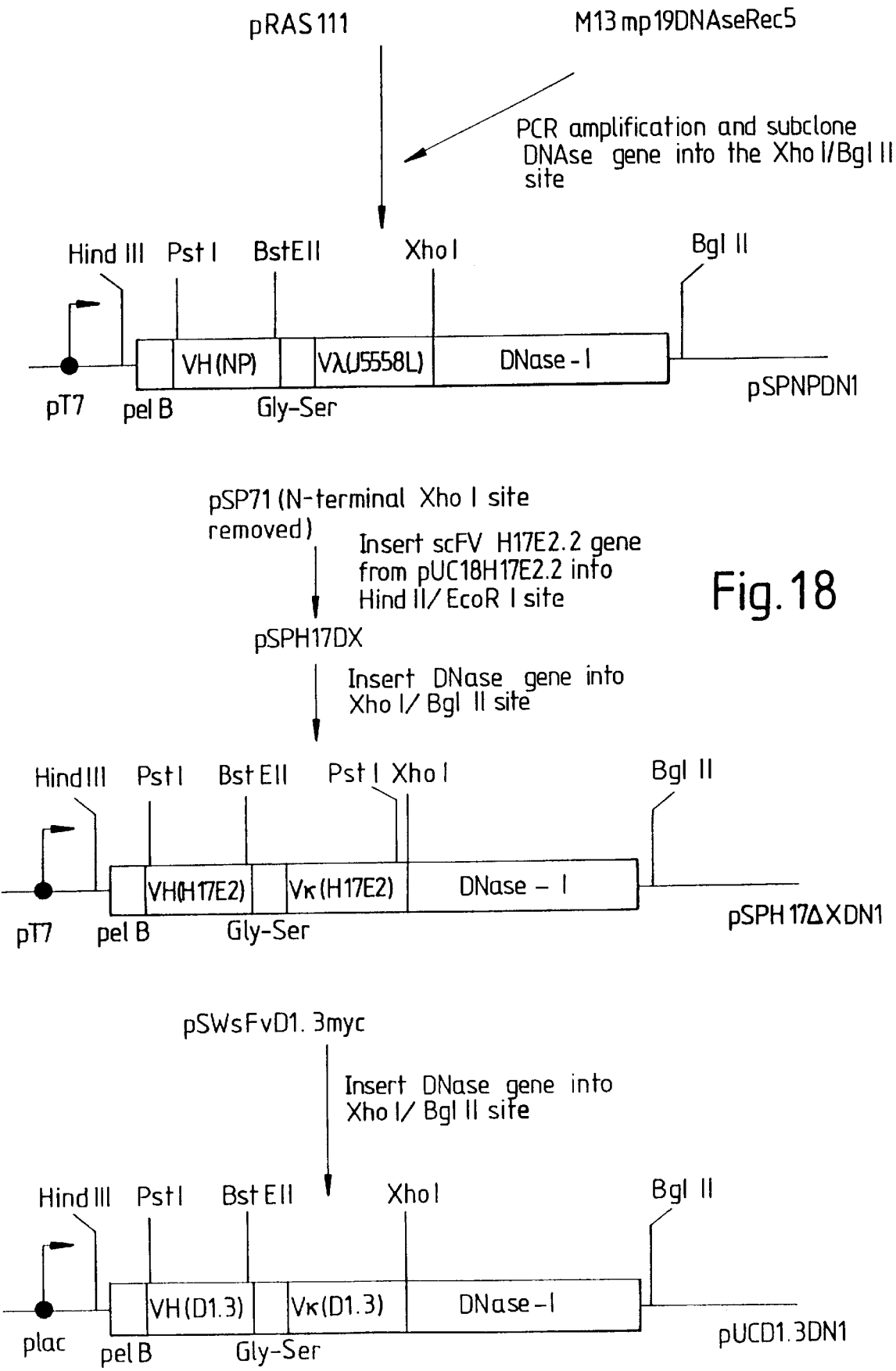
FIG. 18 shows the construction of plasmids expressing ScFv-DNAseI fusion molecules.

Construction of ScFv-DNAseI Fusion Molecules Without a Nuclear Localization Signal Plasmids for the expression of ScFv-DNAseI fusions are shown in FIG. 18. The plasmid pRAS111 is described in Example 1 and M13mp19DNAseRec5 is described in Worrall and Connolly, loc. cit.

FIG. 24 shows the sequence of the ScFv-DNaseI fusion (4-OH nitrophenacetyl antibody) inserted between the HindIII and BglII sites of plasmid pSP71 to give plasmid pSPNPDN1 as shown in FIG. 18.

FIG. 25 shows the sequence of the ScFv-DNaseI fusion (anti-human placental alkaline phosphatase antibody; H17E2) inserted between the HindIII and BglII sites of plasmid pSP71 to give plasmid pSPH17ΔXDN1 as shown in FIG. 18.

FIG. 26 shows the sequence of the ScFv-DNase fusion (anti-lysozyme antibody) inserted between the HindIII and BglII sites of plasmid pUC 18 to give pUCD1.3DN1 as shown in FIG. 18.

The plasmids were made using standard methods of molecular biology as disclosed in Sambrook et al (1989) in *Molecular Cloning, a laboratory manual*, 2nd Edn, Cold Spring Harbor Laboratory Press, NY, USA.

The plasmid pSPNPDN1 encodes a protein which directs DNaseI to a target cell-specific molecule derivatised with NP or NIP.

The plasmid pSPH17ΔXDN1 encodes a protein which directs DNaseI to cells expressing the human placental alkaline phosphatase antigen. The ScFv encoded by this plasmid is derived from the monoclonal antibody H17E2 (see Table 1).

The scFv-DNase I fusion has been expressed under identical conditions to that of the RNase fusions and refolded. The crude refolded preparation of the scFv-DNase I fusion protein shows PLAP-antigen binding activity in an ELISA system similar to the parent antibody H17E2. The detecting layers are anti-bovine DNase I (from rabbit) and anti-rabbit (from goat). The DNase I fusion protein also demonstrates DNA-degrading activity, in a similar system as that of the RNase assay, except 2 μg of DNA is incubated. The activity is only present when 10 mM $CaCl_2$ and 4 mM $MgCl_2$ is added, as is found with the naturally occurring bovine DNase I. suggesting that functional scFv-DNase fusion molecules have been expressed and refolded from *E. coli*.

---

We claim:

1. A compound comprising a target cell-specific portion and a cytotoxic portion characterised in that the cytotoxic portion has DNA endonucleolytic activity.

2. A compound according to claim 1 wherein the cytotoxic portion is at least the catalytically active portion of a DNA endonuclease.

3. A compound according to claim 2 wherein the endonuclease is a mammalian deoxyribonuclease I.

4. A compound according to claim 3 wherein a nuclear localization signal is incorporated.

5. A compound according to claim 4 wherein the nuclear localization signal comprises the sequence PKKKRKV: SEQ ID NO 1.

6. A compound according to claim 6 wherein the DNA endonuclease is a restriction endonuclease.

7. A compound according to claim 1, wherein the target cell-specific portion comprises a ScFv.

8. A compound according to claim 1, wherein the target cell-specific portion and the cytotoxic portion are fused.

9. A compound according to claim 1, wherein the target cell-specific portion bind selectively to a tumour cell.

10. A composition comprising the compound of claim 1 and a pharmaceutical carrier.

* * * * *

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO: 1:

```
Pro Lys Lys Lys Arg Lys Val
1               5
```

(2) INFORMATION FOR SEQ ID NO: 2:

(i) SEQUENCE CHARACTERISTICS:
      (A) LENGTH: 858 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 40..846

(xi) SEQUENCE DESCRIPTION: SEQ ID NO: 2:

```
AAGCTTGCAT GCAAATTCTA TTTCAAGGAG ACAGTCATA ATG AAA TAC CTA TTG        54
                                           Met Lys Tyr Leu Leu
                                            1               5

CCT ACG GCA GCC GCT GGA TTG TTA TTA CTC GCT GCC CAA CCA GCG ATG      102
Pro Thr Ala Ala Ala Gly Leu Leu Leu Leu Ala Ala Gln Pro Ala Met
                10                  15                  20

GCC CAG GTG CAG CTG CAG CAG CCT GGG GCT GAG CTT GTG AAG CCT GGG      150
Ala Gln Val Gln Leu Gln Gln Pro Gly Ala Glu Leu Val Lys Pro Gly
                25                  30                  35

GCT TCA GTG AAG CTG TCC TGC AAG GCT TCT GGC TAC ACC TTC ACC AGC      198
Ala Ser Val Lys Leu Ser Cys Lys Ala Ser Gly Tyr Thr Phe Thr Ser
            40                  45                  50

TAC TGG ATG CAC TGG GTG AAG CAG AGG CCT GGA CGA GGC CTT GAG TGG      246
Tyr Trp Met His Trp Val Lys Gln Arg Pro Gly Arg Gly Leu Glu Trp
            55                  60                  65

ATT GGA AGG ATT GAT CCT AAT AGT GGT GGT ACT AAG TAC AAT GAG AAG      294
Ile Gly Arg Ile Asp Pro Asn Ser Gly Gly Thr Lys Tyr Asn Glu Lys
    70                  75                  80              85

TTC AAG AGC AAG GCC ACA CTG ACT GTA GAC AAA CCC TCC AGC ACA GCC      342
Phe Lys Ser Lys Ala Thr Leu Thr Val Asp Lys Pro Ser Ser Thr Ala
                90                  95                 100

TAC ATG CAG CTC AGC AGC CTG ACA TCT GAG GAC TCT GCG GTC TAT TAT      390
Tyr Met Gln Leu Ser Ser Leu Thr Ser Glu Asp Ser Ala Val Tyr Tyr
                105                 110                 115

TGT GCA AGA TAC GAT TAC TAC GGT AGT AGC TAC TTT GAC TAC TGG GGC      438
Cys Ala Arg Tyr Asp Tyr Tyr Gly Ser Ser Tyr Phe Asp Tyr Trp Gly
                120                 125                 130
```

```
CAA GGG ACC ACG GTC ACC GTC TCC TCA GGT GGA GGC GGT TCA GGC GGA          486
Gln Gly Thr Thr Val Thr Val Ser Ser Gly Gly Gly Gly Ser Gly Gly
        135                 140                 145

GGT GGC TCT GGC GGT GGC GGA TCC CAG GCT GTT GTG ACT CAG GAA TCT          534
Gly Gly Ser Gly Gly Gly Gly Ser Gln Ala Val Val Thr Gln Glu Ser
150                 155                 160                 165

GCA CTC ACC ACA TCA CCT GGT GAA ACA GTC ACA CTC ACT TGT CGC TCA          582
Ala Leu Thr Thr Ser Pro Gly Glu Thr Val Thr Leu Thr Cys Arg Ser
                170                 175                 180

AGT ACT GGG GCT GTT ACA ACT AGT AAC TAT GCC AAC TGG GTC CAA GAA          630
Ser Thr Gly Ala Val Thr Thr Ser Asn Tyr Ala Asn Trp Val Gln Glu
                185                 190                 195

AAA CCA GAT CAT TTA TTC ACT GGT CTA ATA GGT GGT ACC AAC AAC CGA          678
Lys Pro Asp His Leu Phe Thr Gly Leu Ile Gly Gly Thr Asn Asn Arg
        200                 205                 210

GCT CCA GGT GTT CCT GCC AGA TTC TCA GGC TCC CTG ATT GGA GAC AAG          726
Ala Pro Gly Val Pro Ala Arg Phe Ser Gly Ser Leu Ile Gly Asp Lys
        215                 220                 225

GCT GCC CTC ACC ATC ACA GGG GCA CAG ACT GAG GAT GAG GCA ATA TAT          774
Ala Ala Leu Thr Ile Thr Gly Ala Gln Thr Glu Asp Glu Ala Ile Tyr
230                 235                 240                 245

TTC TGT GCT CTA TGG TAC AGC AAC CAC TGG GTG TTC GGT GGA GGA ACC          822
Phe Cys Ala Leu Trp Tyr Ser Asn His Trp Val Phe Gly Gly Gly Thr
                250                 255                 260

AAA CTG ACT GTC CTA GGT CTC GAG TAATAAGAAT TC                            858
Lys Leu Thr Val Leu Gly Leu Glu
                265

(2) INFORMATION FOR SEQ ID NO: 3:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO: 3:

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Pro Gly Ala Glu
            20                  25                  30

Leu Val Lys Pro Gly Ala Ser Val Lys Leu Ser Cys Lys Ala Ser Gly
        35                  40                  45

Tyr Thr Phe Thr Ser Tyr Trp Met His Trp Val Lys Gln Arg Pro Gly
    50                  55                  60

Arg Gly Leu Glu Trp Ile Gly Arg Ile Asp Pro Asn Ser Gly Gly Thr
65                  70                  75                  80

Lys Tyr Asn Glu Lys Phe Lys Ser Lys Ala Thr Leu Thr Val Asp Lys
                85                  90                  95

Pro Ser Ser Thr Ala Tyr Met Gln Leu Ser Ser Leu Thr Ser Glu Asp
            100                 105                 110

Ser Ala Val Tyr Tyr Cys Ala Arg Tyr Asp Tyr Tyr Gly Ser Ser Tyr
        115                 120                 125

Phe Asp Tyr Trp Gly Gln Gly Thr Thr Val Thr Val Ser Ser Gly Gly
    130                 135                 140

Gly Gly Ser Gly Gly Gly Gly Ser Gly Gly Gly Gly Ser Gln Ala Val
145                 150                 155                 160

Val Thr Gln Glu Ser Ala Leu Thr Thr Ser Pro Gly Glu Thr Val Thr
                165                 170                 175
```

```
Leu Thr Cys Arg Ser Ser Thr Gly Ala Val Thr Thr Ser Asn Tyr Ala
            180                 185                 190

Asn Trp Val Gln Glu Lys Pro Asp His Leu Phe Thr Gly Leu Ile Gly
        195                 200                 205

Gly Thr Asn Asn Arg Ala Pro Gly Val Pro Ala Arg Phe Ser Gly Ser
    210                 215                 220

Leu Ile Gly Asp Lys Ala Ala Leu Thr Ile Thr Gly Ala Gln Thr Glu
225                 230                 235                 240

Asp Glu Ala Ile Tyr Phe Cys Ala Leu Trp Tyr Ser Asn His Trp Val
                245                 250                 255

Phe Gly Gly Gly Thr Lys Leu Thr Val Leu Gly Leu Glu
            260                 265
```

(2) INFORMATION FOR SEQ ID NO: 4:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 40..1344

(xi) SEQUENCE DESCRIPTION: SEQ ID NO: 4:

```
AAGCTTGCAT GCAAATTCTA TTTCAAGGAG ACAGTCATA ATG AAA TAC CTA TTG            54
                                           Met Lys Tyr Leu Leu
                                            1               5

CCT ACG GCA GCC GCT GGA TTG TTA TTA CTC GCT GCC CAA CCA GCG ATG          102
Pro Thr Ala Ala Ala Gly Leu Leu Leu Leu Ala Ala Gln Pro Ala Met
                10                  15                  20

GCC CAG GTG CAG CTG CAG CAG CCT GGG GCT GAG CTT GTG AAG CCT GGG          150
Ala Gln Val Gln Leu Gln Gln Pro Gly Ala Glu Leu Val Lys Pro Gly
            25                  30                  35

GCT TCA GTG AAG CTG TCC TGC AAG GCT TCT GGC TAC ACC TTC ACC AGC          198
Ala Ser Val Lys Leu Ser Cys Lys Ala Ser Gly Tyr Thr Phe Thr Ser
        40                  45                  50

TAC TGG ATG CAC TGG GTG AAG CAG AGG CCT GGA CGA GGC CTT GAG TGG          246
Tyr Trp Met His Trp Val Lys Gln Arg Pro Gly Arg Gly Leu Glu Trp
    55                  60                  65

ATT GGA AGG ATT GAT CCT AAT AGT GGT GGT ACT AAG TAC AAT GAG AAG          294
Ile Gly Arg Ile Asp Pro Asn Ser Gly Gly Thr Lys Tyr Asn Glu Lys
70                  75                  80                  85

TTC AAG AGC AAG GCC ACA CTG ACT GTA GAC AAA CCC TCC AGC ACA GCC          342
Phe Lys Ser Lys Ala Thr Leu Thr Val Asp Lys Pro Ser Ser Thr Ala
                90                  95                  100

TAC ATG CAG CTC AGC AGC CTG ACA TCT GAG GAC TCT GCG GTC TAT TAT          390
Tyr Met Gln Leu Ser Ser Leu Thr Ser Glu Asp Ser Ala Val Tyr Tyr
            105                 110                 115

TGT GCA AGA TAC GAT TAC TAC GGT AGT AGC TAC TTT GAC TAC TGG GGC          438
Cys Ala Arg Tyr Asp Tyr Tyr Gly Ser Ser Tyr Phe Asp Tyr Trp Gly
        120                 125                 130

CAA GGG ACC ACG GTC ACC GTC TCC TCA GGT GGA GGC GGT TCA GGC GGA          486
Gln Gly Thr Thr Val Thr Val Ser Ser Gly Gly Gly Gly Ser Gly Gly
    135                 140                 145

GGT GGC TCT GGC GGT GGC GGA TCC CAG GCT GTT GTG ACT CAG GAA TCT          534
Gly Gly Ser Gly Gly Gly Gly Ser Gln Ala Val Val Thr Gln Glu Ser
```

-continued

```
         150                 155                 160                 165
GCA CTC ACC ACA TCA CCT GGT GAA ACA GTC ACA CTC ACT TGT CGC TCA          582
Ala Leu Thr Thr Ser Pro Gly Glu Thr Val Thr Leu Thr Cys Arg Ser
                170                 175                 180

AGT ACT GGG GCT GTT ACA ACT AGT AAC TAT GCC AAC TGG GTC CAA GAA          630
Ser Thr Gly Ala Val Thr Thr Ser Asn Tyr Ala Asn Trp Val Gln Glu
            185                 190                 195

AAA CCA GAT CAT TTA TTC ACT GGT CTA ATA GGT GGT ACC AAC AAC CGA          678
Lys Pro Asp His Leu Phe Thr Gly Leu Ile Gly Gly Thr Asn Asn Arg
        200                 205                 210

GCT CCA GGT GTT CCT GCC AGA TTC TCA GGC TCC CTG ATT GGA GAC AAG          726
Ala Pro Gly Val Pro Ala Arg Phe Ser Gly Ser Leu Ile Gly Asp Lys
    215                 220                 225

GCT GCC CTC ACC ATC ACA GGG GCA CAG ACT GAG GAT GAG GCA ATA TAT          774
Ala Ala Leu Thr Ile Thr Gly Ala Gln Thr Glu Asp Glu Ala Ile Tyr
230                 235                 240                 245

TTC TGT GCT CTA TGG TAC AGC AAC CAC TGG GTG TTC GGT GGA GGA ACC          822
Phe Cys Ala Leu Trp Tyr Ser Asn His Trp Val Phe Gly Gly Gly Thr
                250                 255                 260

AAA CTG ACT GTC CTA GGT CTC GAG GCA CCT GCT GCC GCA CCT GCA GAC          870
Lys Leu Thr Val Leu Gly Leu Glu Ala Pro Ala Ala Ala Pro Ala Asp
            265                 270                 275

CCG TCC AAG GAC TCC AAA GCT CAG GTT TCT GCA GCC GAA GCT GGT ATC          918
Pro Ser Lys Asp Ser Lys Ala Gln Val Ser Ala Ala Glu Ala Gly Ile
        280                 285                 290

ACT GGC ACC TGG TAT AAC CAA CTG GGG TCG ACT TTC ATT GTG ACC GCT          966
Thr Gly Thr Trp Tyr Asn Gln Leu Gly Ser Thr Phe Ile Val Thr Ala
    295                 300                 305

GGT GCG GAC GGA GCT CTG ACT GGC ACC TAC GAA TCT GCG GTT GGT AAC         1014
Gly Ala Asp Gly Ala Leu Thr Gly Thr Tyr Glu Ser Ala Val Gly Asn
310                 315                 320                 325

GCA GAA TCC CGC TAC GTA CTG ACT GGC CGT TAT GAC TCT GCA CCT GCC         1062
Ala Glu Ser Arg Tyr Val Leu Thr Gly Arg Tyr Asp Ser Ala Pro Ala
                330                 335                 340

ACC GAT GGC TCT GGT ACC GCT CTG GGC TGG ACT GTG GCT TGG AAA AAC         1110
Thr Asp Gly Ser Gly Thr Ala Leu Gly Trp Thr Val Ala Trp Lys Asn
            345                 350                 355

AAC TAT CGT AAT GCG CAC AGC GCC ACT ACG TGG TCT GGC CAA TAC GTT         1158
Asn Tyr Arg Asn Ala His Ser Ala Thr Thr Trp Ser Gly Gln Tyr Val
        360                 365                 370

GGC GGT GCT GAG GCT CGT ATC AAC ACT CAG TGG CTG TTA ACA TCC GGC         1206
Gly Gly Ala Glu Ala Arg Ile Asn Thr Gln Trp Leu Leu Thr Ser Gly
    375                 380                 385

ACT ACC GAA GCG AAT GCA TGG AAA TCG ACA CTA GTA GGT CAT GAC ACC         1254
Thr Thr Glu Ala Asn Ala Trp Lys Ser Thr Leu Val Gly His Asp Thr
390                 395                 400                 405

TTT ACC AAA GTT AAG CCT TCT GCT GCT AGC ATT GAT GCT GCC AAG AAA         1302
Phe Thr Lys Val Lys Pro Ser Ala Ala Ser Ile Asp Ala Ala Lys Lys
                410                 415                 420

GCA GGC GTA AAC AAC GGT AAC CCT CTA GAC GCT GTT CAG CAA                 1344
Ala Gly Val Asn Asn Gly Asn Pro Leu Asp Ala Val Gln Gln
            425                 430                 435

TAATAAGAAT TC                                                            1356
```

(2) INFORMATION FOR SEQ ID NO: 5:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Gln Pro Gly Ala Glu
             20                  25                  30

Leu Val Lys Pro Gly Ala Ser Val Lys Leu Ser Cys Lys Ala Ser Gly
         35                  40                  45

Tyr Thr Phe Thr Ser Tyr Trp Met His Trp Val Lys Gln Arg Pro Gly
     50                  55                  60

Arg Gly Leu Glu Trp Ile Gly Arg Ile Asp Pro Asn Ser Gly Gly Thr
 65                  70                  75                  80

Lys Tyr Asn Glu Lys Phe Lys Ser Lys Ala Thr Leu Thr Val Asp Lys
                 85                  90                  95

Pro Ser Ser Thr Ala Tyr Met Gln Leu Ser Ser Leu Thr Ser Glu Asp
             100                 105                 110

Ser Ala Val Tyr Tyr Cys Ala Arg Tyr Asp Tyr Tyr Gly Ser Ser Tyr
         115                 120                 125

Phe Asp Tyr Trp Gly Gln Gly Thr Thr Val Thr Val Ser Ser Gly Gly
     130                 135                 140

Gly Gly Ser Gly Gly Gly Gly Ser Gly Gly Gly Gly Ser Gln Ala Val
145                 150                 155                 160

Val Thr Gln Glu Ser Ala Leu Thr Thr Ser Pro Gly Glu Thr Val Thr
                 165                 170                 175

Leu Thr Cys Arg Ser Ser Thr Gly Ala Val Thr Thr Ser Asn Tyr Ala
             180                 185                 190

Asn Trp Val Gln Glu Lys Pro Asp His Leu Phe Thr Gly Leu Ile Gly
         195                 200                 205

Gly Thr Asn Asn Arg Ala Pro Gly Val Pro Ala Arg Phe Ser Gly Ser
     210                 215                 220

Leu Ile Gly Asp Lys Ala Ala Leu Thr Ile Thr Gly Ala Gln Thr Glu
225                 230                 235                 240

Asp Glu Ala Ile Tyr Phe Cys Ala Leu Trp Tyr Ser Asn His Trp Val
                 245                 250                 255

Phe Gly Gly Gly Thr Lys Leu Thr Val Leu Gly Leu Glu Ala Pro Ala
             260                 265                 270

Ala Ala Pro Ala Asp Pro Ser Lys Asp Ser Lys Ala Gln Val Ser Ala
         275                 280                 285

Ala Glu Ala Gly Ile Thr Gly Thr Trp Tyr Asn Gln Leu Gly Ser Thr
     290                 295                 300

Phe Ile Val Thr Ala Gly Ala Asp Gly Ala Leu Thr Gly Thr Tyr Glu
305                 310                 315                 320

Ser Ala Val Gly Asn Ala Glu Ser Arg Tyr Val Leu Thr Gly Arg Tyr
                 325                 330                 335

Asp Ser Ala Pro Ala Thr Asp Gly Ser Gly Thr Ala Leu Gly Trp Thr
             340                 345                 350

Val Ala Trp Lys Asn Asn Tyr Arg Asn Ala His Ser Ala Thr Thr Trp
         355                 360                 365

Ser Gly Gln Tyr Val Gly Gly Ala Glu Ala Arg Ile Asn Thr Gln Trp
     370                 375                 380

Leu Leu Thr Ser Gly Thr Thr Glu Ala Asn Ala Trp Lys Ser Thr Leu
385                 390                 395                 400

Val Gly His Asp Thr Phe Thr Lys Val Lys Pro Ser Ala Ala Ser Ile
```

```
                405                 410                 415
Asp Ala Ala Lys Lys Ala Gly Val Asn Asn Gly Asn Pro Leu Asp Ala
            420                 425                 430

Val Gln Gln
        435
```

(2) INFORMATION FOR SEQ ID NO: 6:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 40..1284

(xi) SEQUENCE DESCRIPTION: SEQ ID NO: 6:

```
AAGCTTGCAT GCAAATTCTA TTTCAAGGAG ACAGTCATA ATG AAA TAC CTA TTG         54
                                            Met Lys Tyr Leu Leu
                                              1               5

CCT ACG GCA GCC GCT GGA TTG TTA TTA CTC GCT GCC CAA CCA GCG ATG       102
Pro Thr Ala Ala Ala Gly Leu Leu Leu Leu Ala Ala Gln Pro Ala Met
                    10                  15                  20

GCC CAG GTG CAG CTG CAG CAG CCT GGG GCT GAG CTT GTG AAG CCT GGG       150
Ala Gln Val Gln Leu Gln Gln Pro Gly Ala Glu Leu Val Lys Pro Gly
                25                  30                  35

GCT TCA GTG AAG CTG TCC TGC AAG GCT TCT GGC TAC ACC TTC ACC AGC       198
Ala Ser Val Lys Leu Ser Cys Lys Ala Ser Gly Tyr Thr Phe Thr Ser
        40                  45                  50

TAC TGG ATG CAC TGG GTG AAG CAG AGG CCT GGA CGA GGC CTT GAG TGG       246
Tyr Trp Met His Trp Val Lys Gln Arg Pro Gly Arg Gly Leu Glu Trp
 55                  60                  65

ATT GGA AGG ATT GAT CCT AAT AGT GGT GGT ACT AAG TAC AAT GAG AAG       294
Ile Gly Arg Ile Asp Pro Asn Ser Gly Gly Thr Lys Tyr Asn Glu Lys
 70                  75                  80                  85

TTC AAG AGC AAG GCC ACA CTG ACT GTA GAC AAA CCC TCC AGC ACA GCC       342
Phe Lys Ser Lys Ala Thr Leu Thr Val Asp Lys Pro Ser Ser Thr Ala
                90                  95                  100

TAC ATG CAG CTC AGC AGC CTG ACA TCT GAG GAC TCT GCG GTC TAT TAT       390
Tyr Met Gln Leu Ser Ser Leu Thr Ser Glu Asp Ser Ala Val Tyr Tyr
                105                 110                 115

TGT GCA AGA TAC GAT TAC TAC GGT AGT AGC TAC TTT GAC TAC TGG GGC       438
Cys Ala Arg Tyr Asp Tyr Tyr Gly Ser Ser Tyr Phe Asp Tyr Trp Gly
        120                 125                 130

CAA GGG ACC ACG GTC ACC GTC TCC TCA GGT GGA GGC GGT TCA GGC GGA       486
Gln Gly Thr Thr Val Thr Val Ser Ser Gly Gly Gly Gly Ser Gly Gly
    135                 140                 145

GGT GGC TCT GGC GGT GGC GGA TCC CAG GCT GTT GTG ACT CAG GAA TCT       534
Gly Gly Ser Gly Gly Gly Gly Ser Gln Ala Val Val Thr Gln Glu Ser
150                 155                 160                 165

GCA CTC ACC ACA TCA CCT GGT GAA ACA GTC ACA CTC ACT TGT CGC TCA       582
Ala Leu Thr Thr Ser Pro Gly Glu Thr Val Thr Leu Thr Cys Arg Ser
                170                 175                 180

AGT ACT GGG GCT GTT ACA ACT AGT AAC TAT GCC AAC TGG GTC CAA GAA       630
Ser Thr Gly Ala Val Thr Thr Ser Asn Tyr Ala Asn Trp Val Gln Glu
                185                 190                 195

AAA CCA GAT CAT TTA TTC ACT GGT CTA ATA GGT GGT ACC AAC AAC CGA       678
```

```
                                                                -continued

Lys Pro Asp His Leu Phe Thr Gly Leu Ile Gly Gly Thr Asn Asn Arg
        200                 205                 210

GCT CCA GGT GTT CCT GCC AGA TTC TCA GGC TCC CTG ATT GGA GAC AAG    726
Ala Pro Gly Val Pro Ala Arg Phe Ser Gly Ser Leu Ile Gly Asp Lys
215                 220                 225

GCT GCC CTC ACC ATC ACA GGG GCA CAG ACT GAG GAT GAG GCA ATA TAT    774
Ala Ala Leu Thr Ile Thr Gly Ala Gln Thr Glu Asp Glu Ala Ile Tyr
230                 235                 240                 245

TTC TGT GCT CTA TGG TAC AGC AAC CAC TGG GTG TTC GGT GGA GGA ACC    822
Phe Cys Ala Leu Trp Tyr Ser Asn His Trp Val Phe Gly Gly Gly Thr
                250                 255                 260

AAA CTG ACT GTC CTA GGT CTC GAG GCA CCT GCT GCC GCA CCT GCA GAC    870
Lys Leu Thr Val Leu Gly Leu Glu Ala Pro Ala Ala Ala Pro Ala Asp
                265                 270                 275

CCG TCC AAG GAC TCC AAA GCT CAG GTT TCT GCA GCC GAA GCT GGT ATC    918
Pro Ser Lys Asp Ser Lys Ala Gln Val Ser Ala Ala Glu Ala Gly Ile
            280                 285                 290

ACT GGC ACC TGG TAT AAC CAA CTG GGG TCG ACT TTC ATT GTG ACC GCT    966
Thr Gly Thr Trp Tyr Asn Gln Leu Gly Ser Thr Phe Ile Val Thr Ala
        295                 300                 305

GGT GCG GAC GGA GCT CTG ACT GGC ACC TAC GAA TCT GCG GTT GGT AAC   1014
Gly Ala Asp Gly Ala Leu Thr Gly Thr Tyr Glu Ser Ala Val Gly Asn
310                 315                 320                 325

GCA GAA TCC CGC TAC GTA CTG ACT GGC CGT TAT GAC TCT GCA CCT GCC   1062
Ala Glu Ser Arg Tyr Val Leu Thr Gly Arg Tyr Asp Ser Ala Pro Ala
                330                 335                 340

ACC GAT GGC TCT GGT ACC GCT CTG GGC TGG ACT GTG GCT TGG AAA AAC   1110
Thr Asp Gly Ser Gly Thr Ala Leu Gly Trp Thr Val Ala Trp Lys Asn
                345                 350                 355

AAC TAT CGT AAT GCG CAC AGC GCC ACT ACG TGG TCT GGC CAA TAC GTT   1158
Asn Tyr Arg Asn Ala His Ser Ala Thr Thr Trp Ser Gly Gln Tyr Val
            360                 365                 370

GGC GGT GCT GAG GCT CGT ATC AAC ACT CAG TGG CTG TTA ACA TCC GGC   1206
Gly Gly Ala Glu Ala Arg Ile Asn Thr Gln Trp Leu Leu Thr Ser Gly
        375                 380                 385

ACT ACC GAA GCG AAT GCA TGG AAA TCG ACA CTA GTA GGT CAT GAC ACC   1254
Thr Thr Glu Ala Asn Ala Trp Lys Ser Thr Leu Val Gly His Asp Thr
390                 395                 400                 405

TTT ACC AAA GTT AAG CCT TCT GCT GCT AGC TAATAAGAAT TC             1296
Phe Thr Lys Val Lys Pro Ser Ala Ala Ser
                410                 415

(2) INFORMATION FOR SEQ ID NO: 7:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO: 7:

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Pro Gly Ala Glu
                20                  25                  30

Leu Val Lys Pro Gly Ala Ser Val Lys Leu Ser Cys Lys Ala Ser Gly
            35                  40                  45

Tyr Thr Phe Thr Ser Tyr Trp Met His Trp Val Lys Gln Arg Pro Gly
        50                  55                  60

Arg Gly Leu Glu Trp Ile Gly Arg Ile Asp Pro Asn Ser Gly Gly Thr
```

```
              65                  70                  75                  80
Lys Tyr Asn Glu Lys Phe Lys Ser Lys Ala Thr Leu Thr Val Asp Lys
                    85                  90                  95

Pro Ser Ser Thr Ala Tyr Met Gln Leu Ser Ser Leu Thr Ser Glu Asp
                100                 105                 110

Ser Ala Val Tyr Tyr Cys Ala Arg Tyr Asp Tyr Tyr Gly Ser Ser Tyr
                115                 120                 125

Phe Asp Tyr Trp Gly Gln Gly Thr Thr Val Thr Val Ser Ser Gly Gly
            130                 135                 140

Gly Gly Ser Gly Gly Gly Gly Ser Gly Gly Gly Gly Ser Gln Ala Val
145                 150                 155                 160

Val Thr Gln Glu Ser Ala Leu Thr Thr Ser Pro Gly Glu Thr Val Thr
                165                 170                 175

Leu Thr Cys Arg Ser Ser Thr Gly Ala Val Thr Thr Ser Asn Tyr Ala
                180                 185                 190

Asn Trp Val Gln Glu Lys Pro Asp His Leu Phe Thr Gly Leu Ile Gly
                195                 200                 205

Gly Thr Asn Asn Arg Ala Pro Gly Val Pro Ala Arg Phe Ser Gly Ser
210                 215                 220

Leu Ile Gly Asp Lys Ala Ala Leu Thr Ile Thr Gly Ala Gln Thr Glu
225                 230                 235                 240

Asp Glu Ala Ile Tyr Phe Cys Ala Leu Trp Tyr Ser Asn His Trp Val
                245                 250                 255

Phe Gly Gly Gly Thr Lys Leu Thr Val Leu Gly Leu Glu Ala Pro Ala
                260                 265                 270

Ala Ala Pro Ala Asp Pro Ser Lys Asp Ser Lys Ala Gln Val Ser Ala
            275                 280                 285

Ala Glu Ala Gly Ile Thr Gly Thr Trp Tyr Asn Gln Leu Gly Ser Thr
290                 295                 300

Phe Ile Val Thr Ala Gly Ala Asp Gly Ala Leu Thr Gly Thr Tyr Glu
305                 310                 315                 320

Ser Ala Val Gly Asn Ala Glu Ser Arg Tyr Val Leu Thr Gly Arg Tyr
                325                 330                 335

Asp Ser Ala Pro Ala Thr Asp Gly Ser Gly Thr Ala Leu Gly Trp Thr
                340                 345                 350

Val Ala Trp Lys Asn Asn Tyr Arg Asn Ala His Ser Ala Thr Thr Trp
            355                 360                 365

Ser Gly Gln Tyr Val Gly Gly Ala Glu Ala Arg Ile Asn Thr Gln Trp
370                 375                 380

Leu Leu Thr Ser Gly Thr Thr Glu Ala Asn Ala Trp Lys Ser Thr Leu
385                 390                 395                 400

Val Gly His Asp Thr Phe Thr Lys Val Lys Pro Ser Ala Ala Ser
                405                 410                 415

(2) INFORMATION FOR SEQ ID NO: 8:

(i) SEQUENCE CHARACTERISTICS:
        (A) LENGTH: 1257 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
```

(B) LOCATION: 40..1245

(xi) SEQUENCE DESCRIPTION: SEQ ID NO: 8:

```
AAGCTTGCAT GCAAATTCTA TTTCAAGGAG ACAGTCATA ATG AAA TAC CTA TTG         54
                                            Met Lys Tyr Leu Leu
                                             1               5

CCT ACG GCA GCC GCT GGA TTG TTA TTA CTC GCT GCC CAA CCA GCG ATG        102
Pro Thr Ala Ala Ala Gly Leu Leu Leu Leu Ala Ala Gln Pro Ala Met
                 10                  15                  20

GCC CAG GTG CAG CTG CAG CAG CCT GGG GCT GAG CTT GTG AAG CCT GGG        150
Ala Gln Val Gln Leu Gln Gln Pro Gly Ala Glu Leu Val Lys Pro Gly
                 25                  30                  35

GCT TCA GTG AAG CTG TCC TGC AAG GCT TCT GGC TAC ACC TTC ACC AGC        198
Ala Ser Val Lys Leu Ser Cys Lys Ala Ser Gly Tyr Thr Phe Thr Ser
         40                  45                  50

TAC TGG ATG CAC TGG GTG AAG CAG AGG CCT GGA CGA GGC CTT GAG TGG        246
Tyr Trp Met His Trp Val Lys Gln Arg Pro Gly Arg Gly Leu Glu Trp
     55                  60                  65

ATT GGA AGG ATT GAT CCT AAT AGT GGT GGT ACT AAG TAC AAT GAG AAG        294
Ile Gly Arg Ile Asp Pro Asn Ser Gly Gly Thr Lys Tyr Asn Glu Lys
 70                  75                  80                  85

TTC AAG AGC AAG GCC ACA CTG ACT GTA GAC AAA CCC TCC AGC ACA GCC        342
Phe Lys Ser Lys Ala Thr Leu Thr Val Asp Lys Pro Ser Ser Thr Ala
                 90                  95                 100

TAC ATG CAG CTC AGC AGC CTG ACA TCT GAG GAC TCT GCG GTC TAT TAT        390
Tyr Met Gln Leu Ser Ser Leu Thr Ser Glu Asp Ser Ala Val Tyr Tyr
                105                 110                 115

TGT GCA AGA TAC GAT TAC TAC GGT AGT AGC TAC TTT GAC TAC TGG GGC        438
Cys Ala Arg Tyr Asp Tyr Tyr Gly Ser Ser Tyr Phe Asp Tyr Trp Gly
                120                 125                 130

CAA GGG ACC ACG GTC ACC GTC TCC TCA GGT GGA GGC GGT TCA GGC GGA        486
Gln Gly Thr Thr Val Thr Val Ser Ser Gly Gly Gly Gly Ser Gly Gly
135                 140                 145

GGT GGC TCT GGC GGT GGC GGA TCC CAG GCT GTT GTG ACT CAG GAA TCT        534
Gly Gly Ser Gly Gly Gly Gly Ser Gln Ala Val Val Thr Gln Glu Ser
150                 155                 160                 165

GCA CTC ACC ACA TCA CCT GGT GAA ACA GTC ACA CTC ACT TGT CGC TCA        582
Ala Leu Thr Thr Ser Pro Gly Glu Thr Val Thr Leu Thr Cys Arg Ser
                170                 175                 180

AGT ACT GGG GCT GTT ACA ACT AGT AAC TAT GCC AAC TGG GTC CAA GAA        630
Ser Thr Gly Ala Val Thr Thr Ser Asn Tyr Ala Asn Trp Val Gln Glu
                185                 190                 195

AAA CCA GAT CAT TTA TTC ACT GGT CTA ATA GGT GGT ACC AAC AAC CGA        678
Lys Pro Asp His Leu Phe Thr Gly Leu Ile Gly Gly Thr Asn Asn Arg
                200                 205                 210

GCT CCA GGT GTT CCT GCC AGA TTC TCA GGC TCC CTG ATT GGA GAC AAG        726
Ala Pro Gly Val Pro Ala Arg Phe Ser Gly Ser Leu Ile Gly Asp Lys
215                 220                 225

GCT GCC CTC ACC ATC ACA GGG GCA CAG ACT GAG GAT GAG GCA ATA TAT        774
Ala Ala Leu Thr Ile Thr Gly Ala Gln Thr Glu Asp Glu Ala Ile Tyr
230                 235                 240                 245

TTC TGT GCT CTA TGG TAC AGC AAC CAC TGG GTG TTC GGT GGA GGA ACC        822
Phe Cys Ala Leu Trp Tyr Ser Asn His Trp Val Phe Gly Gly Gly Thr
                250                 255                 260

AAA CTG ACT GTC CTA GGT CTC GAG GCA CCT GCT GCC GCA CCT GCC GAA        870
Lys Leu Thr Val Leu Gly Leu Glu Ala Pro Ala Ala Ala Pro Ala Glu
                265                 270                 275

GCT GGT ATC ACT GGC ACC TGG TAT AAC CAA CTG GGG TCG ACT TTC ATT        918
Ala Gly Ile Thr Gly Thr Trp Tyr Asn Gln Leu Gly Ser Thr Phe Ile
                280                 285                 290
```

```
GTG ACC GCT GGT GCG GAC GGA GCT CTG ACT GGC ACC TAC GAA TCT GCG        966
Val Thr Ala Gly Ala Asp Gly Ala Leu Thr Gly Thr Tyr Glu Ser Ala
    295                 300                 305

GTT GGT AAC GCA GAA TCC CGC TAC GTA CTG ACT GGC CGT TAT GAC TCT       1014
Val Gly Asn Ala Glu Ser Arg Tyr Val Leu Thr Gly Arg Tyr Asp Ser
310                 315                 320                 325

GCA CCT GCC ACC GAT GGC TCT GGT ACC GCT CTG GGC TGG ACT GTG GCT       1062
Ala Pro Ala Thr Asp Gly Ser Gly Thr Ala Leu Gly Trp Thr Val Ala
                330                 335                 340

TGG AAA AAC AAC TAT CGT AAT GCG CAC AGC GCC ACT ACG TGG TCT GGC       1110
Trp Lys Asn Asn Tyr Arg Asn Ala His Ser Ala Thr Thr Trp Ser Gly
            345                 350                 355

CAA TAC GTT GGC GGT GCT GAG GCT CGT ATC AAC ACT CAG TGG CTG TTA       1158
Gln Tyr Val Gly Gly Ala Glu Ala Arg Ile Asn Thr Gln Trp Leu Leu
        360                 365                 370

ACA TCC GGC ACT ACC GAA GCG AAT GCA TGG AAA TCG ACA CTA GTA GGT       1206
Thr Ser Gly Thr Thr Glu Ala Asn Ala Trp Lys Ser Thr Leu Val Gly
    375                 380                 385

CAT GAC ACC TTT ACC AAA GTT AAG CCT TCT GCT GCT AGC TAATAAGAAT        1255
His Asp Thr Phe Thr Lys Val Lys Pro Ser Ala Ala Ser
390                 395                 400

TC                                                                    1257

(2) INFORMATION FOR SEQ ID NO: 9:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO: 9:

Met Lys Tyr Leu Leu Pro Thr Ala Ala Gly Leu Leu Leu Leu Ala
1               5                   10                  15

Ala Gln Pro Ala Met Ala Gln Val Gln Leu Gln Gln Pro Gly Ala Glu
                20                  25                  30

Leu Val Lys Pro Gly Ala Ser Val Lys Leu Ser Cys Lys Ala Ser Gly
            35                  40                  45

Tyr Thr Phe Thr Ser Tyr Trp Met His Trp Val Lys Gln Arg Pro Gly
        50                  55                  60

Arg Gly Leu Glu Trp Ile Gly Arg Ile Asp Pro Asn Ser Gly Gly Thr
65                  70                  75                  80

Lys Tyr Asn Glu Lys Phe Lys Ser Lys Ala Thr Leu Thr Val Asp Lys
                85                  90                  95

Pro Ser Ser Thr Ala Tyr Met Gln Leu Ser Ser Leu Thr Ser Glu Asp
                100                 105                 110

Ser Ala Val Tyr Tyr Cys Ala Arg Tyr Asp Tyr Tyr Gly Ser Ser Tyr
            115                 120                 125

Phe Asp Tyr Trp Gly Gln Gly Thr Thr Val Thr Val Ser Ser Gly Gly
        130                 135                 140

Gly Gly Ser Gly Gly Gly Gly Ser Gly Gly Gly Gly Ser Gln Ala Val
145                 150                 155                 160

Val Thr Gln Glu Ser Ala Leu Thr Thr Ser Pro Gly Glu Thr Val Thr
                165                 170                 175

Leu Thr Cys Arg Ser Ser Thr Gly Ala Val Thr Thr Ser Asn Tyr Ala
            180                 185                 190

Asn Trp Val Gln Glu Lys Pro Asp His Leu Phe Thr Gly Leu Ile Gly
        195                 200                 205
```

```
Gly Thr Asn Asn Arg Ala Pro Gly Val Pro Ala Arg Phe Ser Gly Ser
    210                 215                 220

Leu Ile Gly Asp Lys Ala Ala Leu Thr Ile Thr Gly Ala Gln Thr Glu
225                 230                 235                 240

Asp Glu Ala Ile Tyr Phe Cys Ala Leu Trp Tyr Ser Asn His Trp Val
                245                 250                 255

Phe Gly Gly Gly Thr Lys Leu Thr Val Leu Gly Leu Glu Ala Pro Ala
            260                 265                 270

Ala Ala Pro Ala Glu Ala Gly Ile Thr Gly Thr Trp Tyr Asn Gln Leu
        275                 280                 285

Gly Ser Thr Phe Ile Val Thr Ala Gly Ala Asp Gly Ala Leu Thr Gly
    290                 295                 300

Thr Tyr Glu Ser Ala Val Gly Asn Ala Glu Ser Arg Tyr Val Leu Thr
305                 310                 315                 320

Gly Arg Tyr Asp Ser Ala Pro Ala Thr Asp Gly Ser Gly Thr Ala Leu
                325                 330                 335

Gly Trp Thr Val Ala Trp Lys Asn Asn Tyr Arg Asn Ala His Ser Ala
            340                 345                 350

Thr Thr Trp Ser Gly Gln Tyr Val Gly Gly Ala Glu Ala Arg Ile Asn
        355                 360                 365

Thr Gln Trp Leu Leu Thr Ser Gly Thr Thr Glu Ala Asn Ala Trp Lys
    370                 375                 380

Ser Thr Leu Val Gly His Asp Thr Phe Thr Lys Val Lys Pro Ser Ala
385                 390                 395                 400

Ala Ser
```

(2) INFORMATION FOR SEQ ID NO: 10:

(i) SEQUENCE CHARACTERISTICS:
        (A) LENGTH: 1259 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 10:

```
AAGCTTGCAT GCAAATTCTA TTTCAAGGAG ACAGTCATAA TGAAATACCT ATTGCCTACG      60

GCAGCCGCTG GATTGTTATT ACTCGCTGCC CAACCAGCGA TGGCCCAGGT GCAGCTGCAG     120

CAGCCTGGGG CTGAGCTTGT GAAGCCTGGG GCTTCAGTGA AGCTGTCCTG CAAGGCTTCT    180

GGCTACACCT TCACCAGCTA CTGGATGCAC TGGGTGAAGC AGAGGCCTGG ACGAGGCCTT    240

GAGTGGATTG GAAGGATTGA TCCTAATAGT GGTGGTACTA AGTACAATGA AAAGTTCAAG    300

AGCAAGGCCA CACTGACTGT AGACAAACCC TCCAGCACAG CCTACATGCA GCTCAGCAGC    360

CTGACATCTG AGGACTCTGC GGTCTATTAT TGTGCAAGAT ACGATTACTA CGGTAGTAGC    420

TACTTTGACT ACTGGGGCCA AGGGACCACG GTCACCGTCT CCTCAGGTGG AGGCGGTTCA    480

GGCGGAGGTG GCTCTGGCGG TGGCGGATCC CAGGCTGTTG TGACTCAGGA ATCTGCACTC    540

ACCACATCAC CTGGTGAAAC AGTCACACTC ACTTGTCGCT CAAGTACTGG GGCTGTTACA    600

ACTAGTAACT ATGCCAACTG GGTCCAAGAA AAACCAGATC ATTTATTCAC TGGTCTAATA    660

GGTGGTACCA CAACCGAGC TCCAGGTGTT CCTGCCAGAT TCTCAGGCTC CCTGATTGGA     720

GACAAGGCTG CCCTCACCAT CACAGGGGCA CAGACTGAGG ATGAGGCAAT ATATTTCTGT    780
```

```
GCTCTATGGT ACAGCAACCA CTGGGTGTTC GGTGGAGGAA CCAAACTGAC TGTCCTAGGT        840

CTCGAGATCA AGCGCAAGGA ATCTGCAGCT GCCAAGTTCG AGCGGCAGCA CATGGACTCT        900

GGCAACTCCC CCAGCAGCAG CTCCAACTAC TGCAACCTGA TGATGTGCTG CCGAAGATGA        960

CCCAGGGGAA ATGCAAGCCA GTGAACACCT TTGTGCATGA GTCCCTGGCC GATGTTAAGG       1020

CCGTGTGCTC CCAGAAGAAA GTCACTTGCA AGAATGGGCA GACCAACTGC TACCAGAGCA       1080

AATCCACCAT GCGCATCACA GACTGCCGCG AGACTGGCAG CTCCAAGTAC CCCAACTGCG       1140

CCTACAAGAC CACCCAGGTG GAGAAACACA TCATAGTGGC TTGTGGCGGT AAACCGTCCG       1200

TGCCAGTCCA CTTCGATGCT TCAGTGTAGA TCTCCACCTG AGGCCAGAAC AGTGAATTC        1259
```

(2) INFORMATION FOR SEQ ID NO: 11:

(i) SEQUENCE CHARACTERISTICS:
        (A) LENGTH: 1235 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 11:

```
AAGCTTGCAT GCAAATTCTA TTTCAAGGAG ACAGTCATAA TGAAATACCT ATTGCCTACG         60

GCAGCCGCTG GATTGTTATT ACTCGCTGCC CAACCAGCGA TGGCCCAGGT GCAGGAGTCA        120

GGACCTGGCC TGGTGGCGCC CTCACAGAGC CTGTCCATCA CATGCACTGT CTCAGGGTTC        180

TCATTAACCA GTTATGGTGT AAGCTGGGTT CGCCAGCCTC AAGAAAGGG TCTGGAGTGG         240

CTGGGAGTAA TATGGGAAGA CGGGAGCACA AATTATCATT CACGTCTCAT ATCCAGACTG        300

AGCATCAACA AGGATAACTC CAAGAGCCAA GTTTTCTTAA AACTGAACAG TCTGCAAACT        360

GATGACACAG CCACGTACTA CTGTGCCAAA CCCCACTACG GTAGCAGCAA CGTGGGGGCT        420

ATGGAATACT GGGGTCAAGG AACCTCGGTC ACCGTCTCCT CAGGTGGAGG CGGTTCAGGC        480

GGAGGTGGCT CTGGCGGTGG CGGATCGGAC ATCGAGCTCA CCCAGTCTCC AGCCTCCCTA        540

ACTGCATCTG TGGGAGAAAC TGTCACCATC ACCTGTCGAG CAAGTGAAAA TATTTACAGT        600

TATGTAGCAT GGTATCAGCA GAAACAGGGA AAATCTCCTC AGTTCCTGGT CTATAATGCA        660

AAATCCTTAG CAGAGGGTGT GCCATCAAGG TTCAGTGGCA GTGGATCAGG CACACAGTTT        720

TCTCTGAAGA TCAACAGCCT GCAGCCTGAA AATTTTGGGA ATTATTACTG TCAACATCAT        780

TATGTTAGTC CGTGGACGTT CGGTGGAGGC ACCAAGCTCG AGATCAAGCG CAAGGAATCT        840

GCAGCTGCCA AGTTCGAGCG GCAGCACATG GACTCTGGCA ACTCCCCCAG CAGCAGCTCC        900

AACTACTGCA ACCTGATGAT GTGCTGCCGA AGATGACCCA GGGGAAATGC AAGCCAGTGA        960

ACACCTTTGT GCATGAGTCC CTGGCCGATG TTAAGGCCGT GTGCTCCCAG AAGAAAGTCA       1020

CTTGCAAGAA TGGGCAGACC AACTGCTACC AGAGCAAATC CACCATGCGC ATCACAGACT       1080

GCCGCGAGAC TGGCAGCTCC AAGTACCCCA ACTGCGCCTA CAAGACCACC CAGGTGGAGA       1140

AACACATCAT AGTGGCTTGT GGCGGTAAAC CGTCCGTGCC AGTCCACTTC GATGCTTCAG       1200

TGTAGATCTC CACCTGAGGC CAGAACAGTG AATTC                                  1235
```

(2) INFORMATION FOR SEQ ID NO: 12:

(i) SEQUENCE CHARACTERISTICS:
        (A) LENGTH: 1226 base pairs
        (B) TYPE: nucleic acid
        (C) STRANDEDNESS: single

```
            (D) TOPOLOGY: linear (ii) MOLECULE TYPE: cDNA (iii) HYPOTHETICAL: NO (xi) SEQUENCE DESCRIPTION: SEQ ID NO: 12:

AAGCTTGCAT GCAAATTCTA TTTCAAGGAG ACAGTCATAA TGAAATACCT ATTGCCTACG     60

GCAGCCGCTG GATTGTTATT ACTCGCTGCC CAACCAGCGA TGGCCCAGGT GCAGCTGCAG    120

GAGTCAGGAC CTGGCCTGGT GGCGCCCTCA CAGACGCTGT CCATCACATG CACCGTCTCA    180

GGGTTCTCAT TAACCGGCTA TGGTGTAAAC TGGGTTCGCC AGCCTCCAGG AAAGGGTCTG    240

GAGTGGCTGG GAATGATTTG GGGTGATGGA ACACAGACT ATAATTCAGC TCTCAAATCC     300

AGACTGAGCA TCAGCAAGGA CAACTCCAAG AGCCAAGTTT TCTTAAAAAT GAACAGTCTG    360

CACACTGATG ACACAGCCAG GTACTACTGT GCCAGAGAGA GAGATTATAG CTTGACTAC     420

TGGGGCCAAG GCACCACGGT CACCGTCTCC TCAGGTGGAG GCGGTTCAGG CGGAGGTGGC    480

TCTGGCGGTG GCGGATCGGA CATCGTCATG ACTCAGTCTC CAGCCTCCCT TTCTGCGTCT    540

GTGGGAGAAA CTGTCACCAT CACATGTCGA GCAAGTGGGA ATATTCACAA TTATTTAGCA    600

TGGTATCAGC AGAAACAGGG AAAATCTCCT CAGCTCCTGG TCTATTATAC AACAACCTTA    660

GCAGATGGTG TGCCATCAAG GTTCAGTGGC AGTGGATCAG GAACACAATA TTCTCTCAAG    720

ATCAACAGCC TGCAGCCTGA AGATTTTGGG AGTTATTACT GTCAACATTT TTGGAGTACT    780

CCTCGGACGT TCGGTGGAGG CACCAAGCTC GAGATCAAGC GCAAGGAATC TGCAGCTGCC    840

AAGTTCGAGC GGCAGCACAT GGACTCTGGC AACTCCCCCA GCAGCAGCTC CAACTACTGC    900

AACCTGATGA TGTGCTGCCG AAGATGACCC AGGGGAAATG CAAGCCAGTG AACACCTTTG    960

TGCATGAGTC CCTGGCCGAT GTTAAGGCCG TGTGCTCCCA GAAGAAAGTC ACTTGCAAGA   1020

ATGGGCAGAC CAACTGCTAC CAGAGCAAAT CCACCATGCG CATCACAGAC TGCCGCGAGA   1080

CTGGCAGCTC CAAGTACCCC AACTGCGCCT ACAAGACCAC CCAGGTGGAG AAACACATCA   1140

TAGTGGCTTG TGGCGGTAAA CCGTCCGTGC CAGTCCACTT CGATGCTTCA GTGTAGATCT   1200

CCACCTGAGG CCAGAACAGT GAATTC                                        1226

(2) INFORMATION FOR SEQ ID NO: 13:

(i) SEQUENCE CHARACTERISTICS:
         (A) LENGTH: 1648 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (xi) SEQUENCE DESCRIPTION: SEQ ID NO: 13:

AAGCTTGCAT GCAAATTCTA TTTCAAGGAG ACAGTCATAA TGAAATACCT ATTGCCTACG     60

GCAGCCGCTG GATTGTTATT ACTCGCTGCC CAACCAGCGA TGGCCCAGGT GCAGCTGCAG    120

CAGCCTGGGG CTGAGCTTGT GAAGCCTGGG GCTTCAGTGA AGCTGTCCTG CAAGGCTTCT    180

GGCTACACCT TCACCAGCTA CTGGATGCAC TGGGTGAAGC AGAGGCCTGG ACGAGGCCTT    240

GAGTGGATTG GAAGGATTGA TCCTAATAGT GGTGGTACTA AGTACAATGA AAAGTTCAAG    300

AGCAAGGCCA CACTGACTGT AGACAAACCC TCCAGCACAG CCTACATGCA GCTCAGCAGC    360

CTGACATCTG AGGACTCTGC GGTCTATTAT TGTGCAAGAT ACGATTACTA CGGTAGTAGC    420

TACTTTGACT ACTGGGGCCA AGGGACCACG GTCACCGTCT CCTCAGGTGG AGGCGGTTCA    480
```

| | |
|---|---|
| GGCGGAGGTG GCTCTGGCGG TGGCGGATCC CAGGCTGTTG TGACTCAGGA ATCTGCACTC | 540 |
| ACCACATCAC CTGGTGAAAC AGTCACACTC ACTTGTCGCT CAAGTACTGG GGCTGTTACA | 600 |
| ACTAGTAACT ATGCCAACTG GGTCCAAGAA AAACCAGATC ATTTATTCAC TGGTCTAATA | 660 |
| GGTGGTACCA ACAACCGAGC TCCAGGTGTT CCTGCCAGAT TCTCAGGCTC CCTGATTGGA | 720 |
| GACAAGGCTG CCCTCACCAT CACAGGGGCA CAGACTGAGG ATGAGGCAAT ATATTTCTGT | 780 |
| GCTCTATGGT ACAGCAACCA CTGGGTGTTC GGTGGAGGAA CCAAACTGAC TGTCCTAGGT | 840 |
| CTCGAGATTA AACGTATGCT TAAGATCGCT GCTTTCAACA TACGTACCTT CGGTGAATCT | 900 |
| AAAATGTCTA ACGCTACGCT AGCATCTTAC ATCGTACGCA TCGTACGCCG TTACGATATC | 960 |
| GTTCTGATCC AGGAAGTTCG CGACTCTCAC CTGGTTGCAG TTGGTAAACT TCTAGACTAC | 1020 |
| CTGAACCAGG ACGACCCGAA CACCTACCAC TACGTTGTTT CTGAACCCCT CGGGCGTAAC | 1080 |
| TCTTACAAAG AACGGTACCT GTTCCTGTTC CGTCCGAACA AAGTTTCAGT ACTGGATACC | 1140 |
| TACCAGTACG ACGACGGATG CGAATCTTGC GGTAACGACT CTTTCTCCCG GAACCGGCT | 1200 |
| GTTGTTAAAT TCTCGAGCCA CTCTACCAAG GTTAAAGAGT TCGCTATCGT TGCTCTGCAC | 1260 |
| AGCGCGCCGT CTGACGCTGT TGCTGAAATC AACTCTCTGT ACGACGTTTA CCTGGACGTT | 1320 |
| CAGCAGAAAT GGCACCTGAA CGACGTCATG CTGATGGGTG ACTTCAACGC TGACTGCTCT | 1380 |
| TATGTAACCT CTTCTCAGTG GTCATCGATT CGTCTGCGCA CCTCGTCGAC CTTCCAGTGG | 1440 |
| CTGATCCCGG ACTCCGCTGA CACCACCGCT ACTAGTACCA ACTGCGCTTA CGACCGTATC | 1500 |
| GTTGTTGCTG GATCCCTGCT GCAGTCTTCT GTTGTACCGG GTAGCGCGGC CCCGTTCGAC | 1560 |
| TTCCAGGCTG CATATGGTCT TTCGAACGAA ATGGCGCTGG CCATCTCTGA TCACTACCCG | 1620 |
| GTTGAGGTAA CCCTGACCTA ATTCTAGA | 1648 |

(2) INFORMATION FOR SEQ ID NO: 14:

(i) SEQUENCE CHARACTERISTICS:
        (A) LENGTH: 1624 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 14:

| | |
|---|---|
| AAGCTTGCAT GCAAATTCTA TTTCAAGGAG ACAGTCATAA TGAAATACCT ATTGCCTACG | 60 |
| GCAGCCGCTG GATTGTTATT ACTCGCTGCC CAACCAGCGA TGGCCCAGGT GCAGGAGTCA | 120 |
| GGACCTGGCC TGGTGGCGCC CTCACAGAGC CTGTCCATCA CATGCACTGT CTCAGGGTTC | 180 |
| TCATTAACCA GTTATGGTGT AAGCTGGGTT CGCCAGCCTC CAAGAAAGGG TCTGGAGTGG | 240 |
| CTGGGAGTAA TATGGGAAGA CGGGAGCACA AATTATCATT CACGTCTCAT ATCCAGACTG | 300 |
| AGCATCAACA AGGATAACTC CAAGAGCCAA GTTTTCTTAA AACTGAACAG TCTGCAAACT | 360 |
| GATGACACAG CCACGTACTA CTGTGCCAAA CCCCACTACG GTAGCAGCAA CGTGGGGGCT | 420 |
| ATGGAATACT GGGGTCAAGG AACCTCGGTC ACCGTCTCCT CAGGTGGAGG CGGTTCAGGC | 480 |
| GGAGGTGGCT CTGGCGGTGG CGGATCGGAC ATCGAGCTCA CCCAGTCTCC AGCCTCCCTA | 540 |
| ACTGCATCTG TGGGAGAAAC TGTCACCATC ACCTGTCGAG CAAGTGAAAA TATTTACAGT | 600 |
| TATGTAGCAT GGTATCAGCA GAAACAGGGA AAATCTCCTC AGTTCCTGGT CTATAATGCA | 660 |
| AAATCCTTAG CAGAGGGTGT GCCATCAAGG TTCAGTGGCA GTGGATCAGG CACACAGTTT | 720 |

```
TCTCTGAAGA TCAACAGCCT GCAGCCTGAA AATTTTGGGA ATTATTACTG TCAACATCAT      780

TATGTTAGTC CGTGGACGTT CGGTGGAGGC ACCAAGCTCG AGATTAAACG TATGCTTAAG      840

ATCGCTGCTT TCAACATACG TACCTTCGGT GAATCTAAAA TGTCTAACGC TACGCTAGCA      900

TCTTACATCG TACGCATCGT ACGCCGTTAC GATATCGTTC TGATCCAGGA AGTTCGCGAC      960

TCTCACCTGG TTGCAGTTGG TAAACTTCTA GACTACCTGA ACCAGGACGA CCCGAACACC     1020

TACCACTACG TTGTTTCTGA ACCCCTCGGG CGTAACTCTT ACAAAGAACG GTACCTGTTC     1080

CTGTTCCGTC CGAACAAAGT TTCAGTACTG GATACCTACC AGTACGACGA CGGATGCGAA     1140

TCTTGCGGTA ACGACTCTTT CTCCCGGGAA CCGGCTGTTG TTAAATTCTC GAGCCACTCT     1200

ACCAAGGTTA AAGAGTTCGC TATCGTTGCT CTGCACAGCG CGCCGTCTGA CGCTGTTGCT     1260

GAAATCAACT CTCTGTACGA CGTTTACCTG GACGTTCAGC AGAAATGGCA CCTGAACGAC     1320

GTCATGCTGA TGGGTGACTT CAACGCTGAC TGCTCTTATG TAACCTCTTC TCAGTGGTCA     1380

TCGATTCGTC TGCGCACCTC GTCGACCTTC CAGTGGCTGA TCCCGGACTC CGCTGACACC     1440

ACCGCTACTA GTACCAACTG CGCTTACGAC CGTATCGTTG TTGCTGGATC CCTGCTGCAG     1500

TCTTCTGTTG TACCGGGTAG CGCGGCCCCG TTCGACTTCC AGGCTGCATA TGGTCTTTCG     1560

AACGAAATGG CGCTGGCCAT CTCTGATCAC TACCCGGTTG AGGTAACCCT GACCTAATTC     1620

TAGA                                                                 1624

(2) INFORMATION FOR SEQ ID NO: 15:

(i) SEQUENCE CHARACTERISTICS:
        (A) LENGTH: 1615 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 15:

AAGCTTGCAT GCAAATTCTA TTTCAAGGAG ACAGTCATAA TGAAATACCT ATTGCCTACG       60

GCAGCCGCTG GATTGTTATT ACTCGCTGCC CAACCAGCGA TGGCCCAGGT GCAGCTGCAG      120

GAGTCAGGAC CTGGCCTGGT GGCGCCCTCA CAGACGCTGT CCATCACATG CACCGTCTCA      180

GGGTTCTCAT TAACCGGCTA TGGTGTAAAC TGGGTTCGCC AGCCTCCAGG AAAGGGTCTG      240

GAGTGGCTGG GAATGATTTG GGGTGATGGA AACACAGACT ATAATTCAGC TCTCAAATCC      300

AGACTGAGCA TCAGCAAGGA CAACTCCAAG AGCCAAGTTT TCTTAAAAAT GAACAGTCTG      360

CACACTGATG ACACAGCCAG GTACTACTGT GCCAGAGAGA GAGATTATAG GCTTGACTAC      420

TGGGGCCAAG GCACCACGGT CACCGTCTCC TCAGGTGGAG GCGGTTCAGG CGGAGGTGGC      480

TCTGGCGGTG GCGGATCGGA CATCGTCATG ACTCAGTCTC CAGCCTCCCT TTCTGCGTCT      540

GTGGGAGAAA CTGTCACCAT CACATGTCGA GCAAGTGGGA ATATTCACAA TTATTTAGCA      600

TGGTATCAGC AGAAACAGGG AAAATCTCCT CAGCTCCTGG TCTATTATAC AACAACCTTA      660

GCAGATGGTG TGCCATCAAG GTTCAGTGGC AGTGGATCAG GAACACAATA TTCTCTCAAG      720

ATCAACAGCC TGCAGCCTGA AGATTTTGGG AGTTATTACT GTCAACATTT TTGGAGTACT      780

CCTCGGACGT TCGGTGGAGG CACCAAGCTC GAGATTAAAC GTATGCTTAA GATCGCTGCT      840

TTCAACATAC GTACCTTCGG TGAATCTAAA ATGTCTAACG CTACGCTAGC ATCTTACATC      900

GTACGCATCG TACGCCGTTA CGATATCGTT CTGATCCAGG AAGTTCGCGA CTCTCACCTG      960

GTTGCAGTTG GTAAACTTCT AGACTACCTG AACCAGGACG ACCCGAACAC CTACCACTAC     1020
```

```
GTTGTTTCTG AACCCCTCGG GCGTAACTCT TACAAAGAAC GGTACCTGTT CCTGTTCCGT    1080

CCGAACAAAG TTTCAGTACT GGATACCTAC CAGTACGACG ACGGATGCGA ATCTTGCGGT    1140

AACGACTCTT TCTCCCGGGA ACCGGCTGTT GTTAAATTCT CGAGCCACTC TACCAAGGTT    1200

AAAGAGTTCG CTATCGTTGC TCTGCACAGC GCGCCGTCTG ACGCTGTTGC TGAAATCAAC    1260

TCTCTGTACG ACGTTTACCT GGACGTTCAG CAGAAATGGC ACCTGAACGA CGTCATGCTG    1320

ATGGGTGACT TCAACGCTGA CTGCTCTTAT GTAACCTCTT CTCAGTGGTC ATCGATTCGT    1380

CTGCGCACCT CGTCGACCTT CCAGTGGCTG ATCCCGGACT CCGCTGACAC CACCGCTACT    1440

AGTACCAACT GCGCTTACGA CCGTATCGTT GTTGCTGGAT CCCTGCTGCA GTCTTCTGTT    1500

GTACCGGGTA GCGCGGCCCC GTTCGACTTC CAGGCTGCAT ATGGTCTTTC GAACGAAATG    1560

GCGCTGGCCA TCTCTGATCA CTACCCGGTT GAGGTAACCC TGACCTAATT CTAGA        1615
```

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 16:

Gly Gly Gly Ser
1

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 17:

CAGGTGCAGC TGCAGGAGTC AGGACC                                          26

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 18:

GGATCCGACA TCGAGCTCAC TCAGTCTCCA                                      30

(2) INFORMATION FOR SEQ ID NO: 19:

(i) SEQUENCE CHARACTERISTICS:
        (A) LENGTH: 36 base pairs
        (B) TYPE: nucleic acid
        (C) STRANDEDNESS: single (D) TOPOLOGY: linear (ii) MOLECULE TYPE: cDNA (iii) HYPOTHETICAL: NO (xi) SEQUENCE DESCRIPTION: SEQ ID NO: 19:

AAGCTTGGAT CCCAGGCTGT TGTGACTCAG GAATCT                                            36

(2) INFORMATION FOR SEQ ID NO: 20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 20:

CCAAACTGAC TGTCCTAGGT CTCGAGTAAT AAGAATTCAT GC                                      42

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 21:

CAGGTCCAAC TGCAGCAGCC TGG                                                          23

(2) INFORMATION FOR SEQ ID NO: 22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 22:

GGGGCCAAGG GACCACGGTC ACCGTCTCCT CA                                                32

(2) INFORMATION FOR SEQ ID NO: 23:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 23:

Ala Pro Ala Ala Ala Pro Ala
1               5

(2) INFORMATION FOR SEQ ID NO: 24:

(i) SEQUENCE CHARACTERISTICS:
        (A) LENGTH: 1259 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 24:

```
ATGAAATACC TATTGCCTAC GGCAGCCGCT GGATTGTTAT TACTCGCTGC CCAACCAGCG      60
ATGGCCCAGC TGCAGGAGTC AGGACCTGGC CTGGTGGCGC CCTCACAGAG CCTGTCCATC     120
ACATGCACTG TCTCAGGGTT CTCATTAACC AGTTATGGTG TAAGCTGGGT TCGCCAGCCT     180
CCAAGAAAGG GTCTGGAGTG GCTGGGAGTA ATATGGGAAG ACGGGAGCAC AAATTATCAT     240
TCACGTCTCA TATCCAGACT GAGCATCAAC AAGGATAACT CCAAGAGCCA AGTTTTCTTA     300
AAACTGAACA GTCTGCAAAC TGATGACACA GCCACGTACT ACTGTGCCAA ACCCCACTAC     360
GGTAGCAGCA ACGTGGGGGC TATGGAATAC TGGGGTCAAG GAACCTCGGT CACCGTCTCC     420
TCAGGTGGAG GCGGTTCAGG CGGAGGTGGC TCTGGCGGTG GCGGATCGGA CATCGAGCTC     480
ACCCAGTCTC CAGCCTCCCT AACTGCATCT GTGGGAGAAA CTGTCACCAT CACCTGTCGA     540
GCAAGTGAAA ATATTTACAG TTATGTAGCA TGGTATCAGC AGAAACAGGG AAAATCTCCT     600
CAGTTCCTGG TCTATAATGC AAAATCCTTA GCAGAGGGTG TGCCATCAAG GTTCAGTGGC     660
AGTGGATCAG GCACACAGTT TTCTCTGAAG ATCAACAGCC TGCAGCCTGA AGATTTTGGG     720
AATTATTACT GTCAACATCA TTATGTTAGT CCGTGGACGT TCGGTGGAGG CACCAAGCTC     780
GAGATCAAGC GCTCTAGCCT CGAAGGTGGG TGCGCTGGTA ATAGAGTCAG AAGATCAGTC     840
GGAAGCAGCC TGTCTTGCGG TGGTCTCGAC GTCGAGATCA AGCGCAAGGA ATCTGCAGCT     900
GCCAAGTTCG AGCGGCAGCA CATGGACTCT GGCAACTCCC CCAGCAGCAG CTCCAACTAC     960
TGCAACCTGA TGATGTGCTG CCGAAGATGA CCCAGGGGAA ATGCAAGCCA GTGAACACCT    1020
TTGTGCATGA GTCCCTGGCC GATGTTAAGG CCGTGTGCTC CCAGAAGAAA GTCACTTGCA    1080
AGAATGGGCA GACCAACTGC TACCAGAGCA AATCCACCAT GCGCATCACA GACTGCCGCG    1140
AGACTGGCAG CTCCAAGTAC CCCAACTGCG CCTACAAGAC CACCCAGGTG GAGAAACACA    1200
TCATAGTGGC TTGTGGCGGT AAACCGTCCG TGCCAGTCCA CTTCGATGCT TCAGTGTAG    1259
```

(2) INFORMATION FOR SEQ ID NO: 25:

(i) SEQUENCE CHARACTERISTICS:
        (A) LENGTH: 1178 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 25:

```
ATGAAATACC TATTGCCTAC GGCAGCCGCT GGATTGTTAT TACTCGCTGC CCAACCAGCG      60
ATGGCCCAGC TGCAGGAGTC AGGACCTGGC CTGGTGGCGC CCTCACAGAG CCTGTCCATC     120
ACATGCACTG TCTCAGGGTT CTCATTAACC AGTTATGGTG TAAGCTGGGT TCGCCAGCCT     180
CCAAGAAAGG GTCTGGAGTG GCTGGGAGTA ATATGGGAAG ACGGGAGCAC AAATTATCAT     240
TCACGTCTCA TATCCAGACT GAGCATCAAC AAGGATAACT CCAAGAGCCA AGTTTTCTTA     300
```

```
AAACTGAACA GTCTGCAAAC TGATGACACA GCCACGTACT ACTGTGCCAA ACCCCACTAC        360

GGTAGCAGCA ACGTGGGGGC TATGGAATAC TGGGGTCAAG GAACCTCGGT CACCGTCTCC        420

TCAGGTGGAG GCGGTTCAGG CGGAGGTGGC TCTGGCGGTG GCGGATCGGA CATCGAGCTC        480

ACCCAGTCTC CAGCCTCCCT AACTGCATCT GTGGGAGAAA CTGTCACCAT CACCTGTCGA        540

GCAAGTGAAA ATATTTACAG TTATGTAGCA TGGTATCAGC AGAAACAGGG AAAATCTCCT        600

CAGTTCCTGG TCTATAATGC AAAATCCTTA GCAGAGGGTG TGCCATCAAG GTTCAGTGGC        660

AGTGGATCAG GCACACAGTT TTCTCTGAAG ATCAACAGCC TGCAGCCTGA AGATTTTGGG        720

AATTATTACT GTCAACATCA TTATGTTAGT CCGTGGACGT TCGGTGGAGG CACCAAGCTC        780

GAGATCAAGC GCAAGGAATC TGCAGCTGCC AAGTTCGAGC GGCAGCACAT GGACTCTGGC        840

AACTCCCCCA GCAGCAGCTC CAACTACTGC AACCTGATGA TGTGCTGCCG AAGATGACCC        900

AGGGGAAATG CAAGCCAGTG AACACCTTTG TGCATGAGTC CCTGGCCGAT GTTAAGGCCG        960

TGTGCTCCCA GAAGAAAGTC ACTTGCAAGA ATGGGCAGAC CAACTGCTAC CAGAGCAAAT       1020

CCACCATGCG CATCACAGAC TGCCGCGAGA CTGGCAGCTC CAAGTACCCC AACTGCGCCT       1080

ACAAGACCAC CCAGGTGGAG AAACACATCA TAGTGGCTTG TGGCGGTAAA CCGTCCGTGC       1140

CAGTCCACTT CGATGCTTCA GTGAAGGACG AACTGTAA                              1178

(2) INFORMATION FOR SEQ ID NO: 26:

(i) SEQUENCE CHARACTERISTICS:
        (A) LENGTH: 1295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 26:

ATGAAATACC TATTGCCTAC GGCAGCCGCT GGATTGTTAT TACTCGCTGC CCAACCAGCG         60

ATGGCCCAGC TGCAGGAGTC AGGACCTGGC CTGGTGGCGC CCTCACAGAG CCTGTCCATC        120

ACATGCACTG TCTCAGGGTT CTCATTAACC AGTTATGGTG TAAGCTGGGT TCGCCAGCCT        180

CCAAGAAAGG GTCTGGAGTG GCTGGGAGTA ATATGGGAAG ACGGGAGCAC AAATTATCAT        240

TCACGTCTCA TATCCAGACT GAGCATCAAC AAGGATAACT CCAAGAGCCA AGTTTTCTTA        300

AAACTGAACA GTCTGCAAAC TGATGACACA GCCACGTACT ACTGTGCCAA ACCCCACTAC        360

GGTAGCAGCA ACGTGGGGGC TATGGAATAC TGGGGTCAAG GAACCTCGGT CACCGTCTCC        420

TCAGGTGGAG GCGGTTCAGG CGGAGGTGGC TCTGGCGGTG GCGGATCGGA CATCGAGCTC        480

ACCCAGTCTC CAGCCTCCCT AACTGCATCT GTGGGAGAAA CTGTCACCAT CACCTGTCGA        540

GCAAGTGAAA ATATTTACAG TTATGTAGCA TGGTATCAGC AGAAACAGGG AAAATCTCCT        600

CAGTTCCTGG TCTATAATGC AAAATCCTTA GCAGAGGGTG TGCCATCAAG GTTCAGTGGC        660

AGTGGATCAG GCACACAGTT TTCTCTGAAG ATCAACAGCC TGCAGCCTGA AGATTTTGGG        720

AATTATTACT GTCAACATCA TTATGTTAGT CCGTGGACGT TCGGTGGAGG CACCAAGCTC        780

GAGATCAAGC GCTCTAGCCT CGAAGGTGGG TGCGCTGGTA ATAGAGTCAG AAGATCAGTC        840

GGAAGCAGCC TGTCTTGCGG TGGTCTCGAC GTCGAGATCA AGGCACCTGC TGCCTCCCCG        900

GCAGACGCTA AGGAATCTGC AGCTGCCAAG TTCGAGCGGC AGCACATGGA CTCTGGCAAC        960

TCCCCCAGCA GCAGCTCCAA CTACTGCAAC CTGATGATGT GCTGCCGAAG ATGACCCAGG       1020
```

```
GGAAATGCAA GCCAGTGAAC ACCTTTGTGC ATGAGTCCCT GGCCGATGTT AAGGCCGTGT      1080

GCTCCCAGAA GAAAGTCACT TGCAAGAATG GGCAGACCAA CTGCTACCAG AGCAAATCCA      1140

CCATGCGCAT CACAGACTGC CGCGAGACTG GCAGCTCCAA GTACCCCAAC TGCGCCTACA      1200

AGACCACCCA GGTGGAGAAA CACATCATAG TGGCTTGTGG CGGTAAACCG TCCGTGCCAG      1260

TCCACTTCGA TGCTTCAGTG AAGGACGAAC TGTAA                                 1295

(2) INFORMATION FOR SEQ ID NO: 27:

(i) SEQUENCE CHARACTERISTICS:
        (A) LENGTH: 1202 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 27:

ATGAAATACC TATTGCCTAC GGCAGCCGCT GGATTGTTAT TACTCGCTGC CCAACCAGCG         60

ATGGCCCAGC TGCAGGAGTC AGGACCTGGC CTGGTGGCGC CCTCACAGAG CCTGTCCATC        120

ACATGCACTG TCTCAGGGTT CTCATTAACC AGTTATGGTG TAAGCTGGGT TCGCCAGCCT        180

CCAAGAAAGG GTCTGGAGTG GCTGGGAGTA ATATGGGAAG ACGGGAGCAC AAATTATCAT        240

TCACGTCTCA TATCCAGACT GAGCATCAAC AAGGATAACT CCAAGAGCCA AGTTTTCTTA        300

AAACTGAACA GTCTGCAAAC TGATGACACA GCCACGTACT ACTGTGCCAA ACCCCACTAC        360

GGTAGCAGCA ACGTGGGGGC TATGGAATAC TGGGGTCAAG GAACCTCGGT CACCGTCTCC        420

TCAGGTGGAG GCGGTTCAGG CGGAGGTGGC TCTGGCGGTG GCGGATCGGA CATCGAGCTC        480

ACCCAGTCTC CAGCCTCCCT AACTGCATCT GTGGGAGAAA CTGTCACCAT CACCTGTCGA        540

GCAAGTGAAA ATATTTACAG TTATGTAGCA TGGTATCAGC AGAAACAGGG AAAATCTCCT        600

CAGTTCCTGG TCTATAATGC AAAATCCTTA GCAGAGGGTG TGCCATCAAG GTTCAGTGGC        660

AGTGGATCAG GCACACAGTT TTCTCTGAAG ATCAACAGCC TGCAGCCTGA AGATTTTGGG        720

AATTATTACT GTCAACATCA TTATGTTAGT CCGTGGACGT TCGGTGGAGG CACCAAGCTC        780

GAGATCAAGG CACCTGCTGC CTCCCCGGCA GACGCTAAGG AATCTGCAGC TGCCAAGTTC        840

GAGCGGCAGC ACATGGACTC TGGCAACTCC CCCAGCAGCA GCTCCAACTA CTGCAACCTG        900

ATGATGTGCT GCCGAAGATG ACCCAGGGGA AATGCAAGCC AGTGAACACC TTTGTGCATG        960

AGTCCCTGGC CGATGTTAAG GCCGTGTGCT CCCAGAAGAA AGTCACTTGC AAGAATGGGC       1020

AGACCAACTG CTACCAGAGC AAATCCACCA TGCGCATCAC AGACTGCCGC GAGACTGGCA       1080

GCTCCAAGTA CCCCAACTGC GCCTACAAGA CCACCCAGGT GGAGAAACAC ATCATAGTGG       1140

CTTGTGGCGG TAAACCGTCC GTGCCAGTCC ACTTCGATGC TTCAGTGAAG GACGAACTGT       1200

AA                                                                     1202

(2) INFORMATION FOR SEQ ID NO: 28:

(i) SEQUENCE CHARACTERISTICS:
        (A) LENGTH: 1178 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

(xi) SEQUENCE DESCRIPTION: SEQ ID NO: 28:

```
ATGAAATACC TATTGCCTAC GGCAGCCGCT GGATTGTTAT TACTCGCTGC CCAACCAGCG      60

ATGGCCCAGC TGCAGGAGTC AGGACCTGGC CTGGTGGCGC CCTCACAGAG CCTGTCCATC     120

ACATGCACTG TCTCAGGGTT CTCATTAACC AGTTATGGTG TAAGCTGGGT TCGCCAGCCT     180

CCAAGAAAGG GTCTGGAGTG GCTGGGAGTA ATATGGAAG ACGGGAGCAC AAATTATCAT      240

TCACGTCTCA TATCCAGACT GAGCATCAAC AAGGATAACT CCAAGAGCCA AGTTTTCTTA     300

AAACTGAACA GTCTGCAAAC TGATGACACA GCCACGTACT ACTGTGCCAA ACCCCACTAC     360

GGTAGCAGCA ACGTGGGGGC TATGGAATAC TGGGGTCAAG GAACCTCGGT CACCGTCTCC     420

TCAGGTGGAG GCGGTTCAGG CGGAGGTGGC TCTGGCGGTG GCGGATCGGA CATCGAGCTC     480

ACCCAGTCTC CAGCCTCCCT AACTGCATCT GTGGGAGAAA CTGTCACCAT CACCTGTCGA     540

GCAAGTGAAA ATATTTACAG TTATGTAGCA TGGTATCAGC AGAAACAGGG AAGATCTCCT     600

CAGTTCCTGG TCTATAATGC AAAATCCTTA GCAGAGGGTG TGCCATCAAG GTTCAGTGGC     660

AGTGGATCAG GCACACAGTT TTCTCTGAAG ATCAACAGCC TGCAGCCTGA AAATTTTGGG     720

AATTATTACT GTCAACATCA TTATGTTAGT CCGTGGACGT TCGGTGGAGG CACCAAGCTC     780

GAGATCAAGC GCAAGGAATC TGCAGCTGCC AAGTTCGAGC GGCAGCACAT GGACTCTGGC     840

AACTCCCCCA GCAGCAGCTC CAACTACTGC AACCTGATGA TGTGCTGCCG AAGATGACCC     900

AGGGGAAATG CAAGCCAGTG AACACCTTTG TGCATGAGTC CCTGGCCGAT GTTAAGGCCG     960

TGTGCTCCCA GAAGAAAGTC ACTTGCAAGA ATGGGCAGAC CAACTGCTAC CAGAGCAAAT    1020

CCACCATGCG CATCACAGAC TGCCGCGAGA CTGGCAGCTC CAAGTACCCC AACTGCGCCT    1080

ACAAGACCAC CCAGGTGGAG AAACACATCA TAGTGGCTTG TGGCGGTAAA CCGTCCGTGC    1140

CAGTCCACTT CGATGCTTCA GTGAAGGACG AACTGTAA                           1178
```

(2) INFORMATION FOR SEQ ID NO: 29:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 29:

Lys Asp Glu Leu